United States Patent
West et al.

(10) Patent No.: US 12,421,513 B2
(45) Date of Patent: *Sep. 23, 2025

(54) COMPOSITIONS AND METHODS FOR INDUCED TISSUE REGENERATION IN MAMMALIAN SPECIES

(71) Applicant: Reverse Bioengineering, Inc., Alameda, CA (US)

(72) Inventors: Michael D. West, Mill Valley, CA (US); Karen Chapman, Mill Valley, CA (US); Hal Sternberg, Berkeley, CA (US)

(73) Assignee: Reverse BioEngineering, Inc., Alameda, CA (US)

( * ) Notice: Subject to any disclaimer, the term of this patent is extended or adjusted under 35 U.S.C. 154(b) by 75 days.

This patent is subject to a terminal disclaimer.

(21) Appl. No.: 17/177,747

(22) Filed: Feb. 17, 2021

(65) Prior Publication Data

US 2022/0112492 A1    Apr. 14, 2022

Related U.S. Application Data

(62) Division of application No. 14/896,664, filed as application No. PCT/US2014/040601 on Jun. 3, 2014, now Pat. No. 10,961,531.

(60) Provisional application No. 61/831,421, filed on Jun. 5, 2013.

(51) Int. Cl.
*C12N 15/113* (2010.01)
*A61K 31/00* (2006.01)
*A61K 31/715* (2006.01)
*C07K 16/18* (2006.01)

(52) U.S. Cl.
CPC ............ *C12N 15/113* (2013.01); *A61K 31/00* (2013.01); *A61K 31/715* (2013.01); *C07K 16/18* (2013.01); *C12N 2310/14* (2013.01)

(58) Field of Classification Search
None
See application file for complete search history.

(56) References Cited

U.S. PATENT DOCUMENTS

| | | |
|---|---|---|
| 5,030,015 A | 7/1991 | Baker et al. |
| 5,489,508 A | 2/1996 | West et al. |
| 5,639,613 A | 6/1997 | Shay et al. |
| 5,686,306 A | 11/1997 | West et al. |
| 5,843,780 A | 12/1998 | Thomson |
| 5,922,601 A | 7/1999 | Baetscher et al. |
| 6,200,806 B1 | 3/2001 | Thomson |
| 6,248,934 B1 | 6/2001 | Tessier-Lavigne et al. |
| 6,280,718 B1 | 8/2001 | Kaufman et al. |
| 6,333,313 B1 | 12/2001 | Copland, III et al. |
| 6,465,493 B1 | 10/2002 | Burgess et al. |
| 6,602,711 B1 | 8/2003 | Thomson et al. |
| 6,667,176 B1 | 12/2003 | Funk et al. |
| 6,685,911 B1 | 2/2004 | Zitvogel et al. |
| 6,887,706 B2 | 5/2005 | Zhang et al. |
| 7,176,023 B2 | 2/2007 | Kaufman et al. |
| 7,217,569 B2 | 5/2007 | Thomson |
| 7,253,334 B2 | 8/2007 | Collas et al. |
| 7,417,041 B2 | 8/2008 | Blumberg et al. |
| 7,582,479 B2 | 9/2009 | Thomson |
| 7,585,622 B1 | 9/2009 | Cech et al. |
| 7,625,573 B2 | 12/2009 | Zitvogel et al. |
| 7,736,895 B2 | 6/2010 | Collas et al. |
| 7,928,069 B2 | 4/2011 | Prestwich et al. |
| 7,951,591 B2 | 5/2011 | Robl et al. |
| 7,981,871 B2 | 7/2011 | Prestwich et al. |
| 8,021,847 B2 | 9/2011 | Pietrzkowski |
| 8,058,065 B2 | 11/2011 | Yamanaka et al. |
| 8,090,542 B2 | 1/2012 | Khvorova et al. |
| 8,236,774 B2 | 8/2012 | Cech et al. |
| 8,247,384 B2 | 8/2012 | Green et al. |
| 8,324,184 B2 | 12/2012 | Prestwich et al. |
| 8,476,017 B2 | 7/2013 | Pietrzkowski |
| 8,685,386 B2 | 4/2014 | West et al. |
| 9,175,263 B2 | 11/2015 | Larocca et al. |
| 10,227,561 B2 | 3/2019 | Larocca et al. |
| 10,240,127 B2 | 3/2019 | Larocca et al. |
| 10,688,136 B2 | 6/2020 | Quarta et al. |
| 10,716,591 B2 | 7/2020 | Anderson et al. |
| 10,961,531 B2 | 3/2021 | West et al. |
| 11,078,462 B2 | 8/2021 | Yang et al. |
| 2001/0039316 A1 | 11/2001 | Campbell et al. |
| 2002/0001842 A1 | 1/2002 | Chapman |
| 2002/0051762 A1 | 5/2002 | Rafii et al. |
| 2002/0069484 A1 | 6/2002 | Creel |
| 2002/0142397 A1 | 10/2002 | Collas et al. |
| 2003/0046722 A1 | 3/2003 | Collas et al. |
| 2003/0129745 A1 | 7/2003 | Robl et al. |
| 2003/0149277 A1 | 8/2003 | Gaster et al. |
| 2003/0161817 A1 | 8/2003 | Young et al. |
| 2003/0166633 A1 | 9/2003 | Gaster et al. |
| 2003/0180268 A1 | 9/2003 | Atala |

(Continued)

FOREIGN PATENT DOCUMENTS

| | | |
|---|---|---|
| CN | 102105789 A | 6/2011 |
| CN | 104114693 A | 10/2014 |

(Continued)

OTHER PUBLICATIONS

West et al. Regenerative Medicine 14(9), 867-886 (Year: 2019).*

(Continued)

*Primary Examiner* — Brian Whiteman
(74) *Attorney, Agent, or Firm* — McCarter & English, LLP; Jonathan M. Sparks

(57) ABSTRACT

Aspects of the present invention include methods and compositions related to the modulation of molecules regulating the regenerative potential of cells and tissues in the embryonic state and the loss thereof in later fetal and adult stages of development. Said methods and compositions have uses in research in stem cell biology and in increasing regenerative potential in fetal and adult tissues otherwise incapable of regeneration.

12 Claims, 17 Drawing Sheets

(56) References Cited

U.S. PATENT DOCUMENTS

| | | |
|---|---|---|
| 2003/0232430 A1 | 12/2003 | Cibelli et al. |
| 2004/0001807 A1 | 1/2004 | Edelberg et al. |
| 2004/0039198 A1 | 2/2004 | Bender et al. |
| 2004/0063745 A1 | 4/2004 | Gellibert et al. |
| 2004/0152738 A1 | 8/2004 | Gaster et al. |
| 2004/0199935 A1 | 10/2004 | Chapman |
| 2004/0219563 A1 | 11/2004 | West et al. |
| 2004/0220230 A1 | 11/2004 | Gaster et al. |
| 2004/0228847 A1 | 11/2004 | Goldschmidt-Clermont et al. |
| 2004/0247567 A1* | 12/2004 | Gurtner ............ A61K 48/0075 424/93.2 |
| 2004/0266842 A1 | 12/2004 | Gaster et al. |
| 2005/0014258 A1 | 1/2005 | Collas et al. |
| 2005/0014938 A1 | 1/2005 | Gaster et al. |
| 2005/0165011 A1 | 7/2005 | Gellibert et al. |
| 2005/0250727 A1 | 11/2005 | Tasken et al. |
| 2006/0003446 A1 | 1/2006 | Keller et al. |
| 2006/0014147 A1 | 1/2006 | Golz |
| 2006/0171930 A1 | 8/2006 | Seyda et al. |
| 2006/0212952 A1 | 9/2006 | Collas et al. |
| 2007/0072901 A1 | 3/2007 | Washio |
| 2007/0116684 A1 | 5/2007 | Atala et al. |
| 2007/0128174 A1* | 6/2007 | Kleinsek ............ A61P 9/10 435/325 |
| 2007/0154428 A1 | 7/2007 | Sato et al. |
| 2007/0154474 A1 | 7/2007 | Soppet et al. |
| 2007/0155013 A1 | 7/2007 | Akaike et al. |
| 2008/0070303 A1 | 3/2008 | West et al. |
| 2008/0233610 A1 | 9/2008 | Thomson |
| 2009/0047263 A1 | 2/2009 | Yamanaka |
| 2009/0104159 A1 | 4/2009 | Prosper et al. |
| 2009/0148423 A1 | 6/2009 | Sumitran-Holgersson |
| 2009/0220450 A1 | 9/2009 | Green et al. |
| 2009/0269314 A1 | 10/2009 | Keller et al. |
| 2010/0003757 A1 | 1/2010 | Mack |
| 2010/0055678 A1 | 3/2010 | Jaatinen et al. |
| 2010/0111914 A1 | 5/2010 | Zhang et al. |
| 2010/0158872 A1 | 6/2010 | Keller et al. |
| 2010/0166713 A1 | 7/2010 | Dalton et al. |
| 2010/0167404 A1 | 7/2010 | West et al. |
| 2010/0183620 A1 | 7/2010 | Bhawe et al. |
| 2010/0184033 A1 | 7/2010 | West et al. |
| 2010/0203021 A1 | 8/2010 | Goumans et al. |
| 2010/0255580 A1 | 10/2010 | Rezania |
| 2010/0267135 A1 | 10/2010 | Sakurada et al. |
| 2010/0330063 A1 | 12/2010 | Weinstein |
| 2011/0014620 A1 | 1/2011 | Basilico et al. |
| 2011/0038791 A1* | 2/2011 | Ford ............ A61K 45/06 514/19.5 |
| 2011/0064701 A1 | 3/2011 | Young et al. |
| 2011/0104133 A1 | 5/2011 | Tseng et al. |
| 2011/0143441 A1 | 6/2011 | West et al. |
| 2011/0218143 A1 | 9/2011 | Kaushal et al. |
| 2011/0223669 A1 | 9/2011 | Yamanaka et al. |
| 2011/0312881 A1 | 12/2011 | Silverman et al. |
| 2012/0060232 A1 | 3/2012 | Stan |
| 2012/0093885 A1 | 4/2012 | Sahoo et al. |
| 2012/0148546 A1 | 6/2012 | Dar-Oaknin et al. |
| 2012/0171171 A1 | 7/2012 | West et al. |
| 2012/0295347 A1 | 11/2012 | Kessler |
| 2012/0301443 A1 | 11/2012 | Raffi et al. |
| 2012/0321671 A1 | 12/2012 | Boyden et al. |
| 2013/0015622 A1 | 1/2013 | Hata |
| 2013/0115609 A1 | 5/2013 | Ho |
| 2013/0115673 A1 | 5/2013 | West et al. |
| 2013/0196865 A1 | 8/2013 | Hochedlinger et al. |
| 2013/0202564 A1 | 8/2013 | Han et al. |
| 2013/0236961 A1 | 9/2013 | Amit et al. |
| 2014/0010801 A1 | 1/2014 | Niedernhofer et al. |
| 2014/0178988 A1 | 6/2014 | West et al. |
| 2014/0178994 A1 | 6/2014 | West et al. |
| 2014/0234964 A1 | 8/2014 | West et al. |
| 2014/0349396 A1 | 11/2014 | West et al. |
| 2015/0017718 A1 | 1/2015 | Nakatsuji et al. |
| 2015/0079110 A1 | 3/2015 | Burns et al. |
| 2015/0202234 A1 | 7/2015 | Gillette et al. |
| 2015/0232808 A1 | 8/2015 | West et al. |
| 2015/0275177 A1 | 10/2015 | West et al. |
| 2016/0002597 A1 | 1/2016 | Sinden et al. |
| 2016/0108368 A1 | 4/2016 | Larocca et al. |
| 2016/0193252 A1 | 7/2016 | Hicks et al. |
| 2016/0305933 A1 | 10/2016 | Shigemoto |
| 2016/0369237 A1 | 12/2016 | West et al. |
| 2017/0108503 A1 | 4/2017 | Klass et al. |
| 2017/0146529 A1 | 5/2017 | Nagrath et al. |
| 2017/0239320 A1* | 8/2017 | Conboy ............ G01N 33/502 |
| 2018/0170982 A1 | 6/2018 | West et al. |
| 2018/0273906 A1 | 9/2018 | Ashraf |
| 2018/0280443 A1 | 10/2018 | Glicksman et al. |
| 2019/0151372 A1 | 5/2019 | Larocca et al. |
| 2019/0175691 A1 | 6/2019 | West et al. |
| 2019/0218511 A1 | 7/2019 | Larocca et al. |
| 2019/0241873 A1 | 8/2019 | Larocca et al. |
| 2020/0157505 A1 | 5/2020 | West et al. |
| 2022/0088137 A1 | 3/2022 | West et al. |
| 2022/0088138 A1 | 3/2022 | West et al. |
| 2022/0090078 A1 | 3/2022 | West et al. |
| 2022/0098554 A1 | 3/2022 | Yang et al. |
| 2022/0160833 A1 | 5/2022 | West et al. |
| 2022/0401494 A1 | 12/2022 | Larocca et al. |
| 2022/0403341 A1 | 12/2022 | Larocca et al. |
| 2023/0093399 A1 | 3/2023 | West et al. |

FOREIGN PATENT DOCUMENTS

| | | |
|---|---|---|
| CN | 104350146 A | 2/2015 |
| CN | 105435244 A | 3/2016 |
| EP | 1001806 A1 | 5/2000 |
| EP | 1523990 A1 | 4/2005 |
| EP | 1860180 A1 | 11/2007 |
| EP | 2254586 A1 | 12/2010 |
| EP | 2496711 A2 | 9/2012 |
| EP | 3387112 A1 | 10/2018 |
| EP | 3463391 A1 | 4/2019 |
| JP | 2013-151437 A | 8/2013 |
| JP | 2016-518393 A | 6/2016 |
| JP | 2019-517538 A | 6/2019 |
| WO | WO-1998/30679 A1 | 7/1998 |
| WO | WO-1999/03499 A1 | 1/1999 |
| WO | WO-1999/20741 A1 | 4/1999 |
| WO | WO-2001/00650 A1 | 1/2001 |
| WO | WO-2001/30978 A1 | 5/2001 |
| WO | WO-2001/51616 A2 | 7/2001 |
| WO | WO-2003/046141 A2 | 6/2003 |
| WO | WO-2003/074654 A2 | 9/2003 |
| WO | WO-2003/076603 A2 | 9/2003 |
| WO | WO-2005/068610 A1 | 7/2005 |
| WO | WO-2005/121369 A2 | 12/2005 |
| WO | WO-2006/054262 A2 | 5/2006 |
| WO | WO-2006/130504 A2 | 12/2006 |
| WO | WO-2007/019398 A1 | 2/2007 |
| WO | WO-2007/047894 A2 | 4/2007 |
| WO | WO-2007/058671 A1 | 5/2007 |
| WO | WO-2007/062198 A1 | 5/2007 |
| WO | WO-2008/089448 A2 | 7/2008 |
| WO | WO-2008/148938 A1 | 12/2008 |
| WO | WO-2009/052211 A1 | 4/2009 |
| WO | WO-2009/105044 A1 | 8/2009 |
| WO | WO-2010/021993 A1 | 2/2010 |
| WO | WO-2011/053257 A2 | 5/2011 |
| WO | WO-2011/150105 A2 | 12/2011 |
| WO | WO-2012/020308 A2 | 2/2012 |
| WO | WO-2012/065065 A1 | 5/2012 |
| WO | WO-2012/125471 A1 | 9/2012 |
| WO | 2012/147470 | 11/2012 |
| WO | WO-2013/003595 A1 | 1/2013 |
| WO | WO-2013/014691 A1 | 1/2013 |
| WO | WO-2013/036969 A1 | 3/2013 |
| WO | 2013/082268 A1 | 6/2013 |
| WO | WO-2013/084000 A2 | 6/2013 |
| WO | WO-2013/150303 A1 | 10/2013 |
| WO | WO-2013/172793 A1 | 11/2013 |
| WO | WO-2014/013258 A1 | 1/2014 |
| WO | WO-2014/022852 A1 | 2/2014 |

(56) References Cited

FOREIGN PATENT DOCUMENTS

| WO | WO-2014/028493 A2 | 2/2014 |
|---|---|---|
| WO | WO-2014/091373 A1 | 6/2014 |
| WO | WO-2014/125276 A1 | 8/2014 |
| WO | WO-2014/125277 A1 | 8/2014 |
| WO | WO-2014/197421 A1 | 12/2014 |
| WO | WO-2015/052526 A1 | 4/2015 |
| WO | WO-2015/052527 A1 | 4/2015 |
| WO | 2017/100313 A1 | 6/2017 |
| WO | WO-2017/214342 A1 | 12/2017 |
| WO | WO-2019/178296 A1 | 9/2019 |
| WO | WO-2019/209892 A1 | 10/2019 |
| WO | WO-2020/069373 A1 | 4/2020 |

OTHER PUBLICATIONS

Elabd et al. Nature Communications 5: 4082, pp. 1-11 (Year: 2014).*
Chiche et al., Injury-Induced Senescence Enables In Vivo Reprogramming in Skeletal Muscle. Cell Stem Cell. Mar. 2, 2017;20(3):407-414.e4.
Ghaedi et al., Human Pluripotent Stem Cells (iPSC) Generation, Culture, and Differentiation to Lung Progenitor Cells. Methods Mol Biol. 2019;1576:55-92.
Kidder et al., Examination of transcriptional networks reveals an important role for TCFAP2C, SMARCA4, and EOMES in trophoblast stem cell maintenance. Genome Res. Apr. 2010;20(4):458-72.
Ofenbauer et al., Strategies for in vivo reprogramming. Curr Opin Cell Biol. Dec. 2019;61:9-15.
Richardson et al., Endothelial progenitor cells: quo vadis? J Mol Cell Cardiol. Feb. 2011;50(2):266-72.
Takahashi et al., Induction of pluripotent stem cells from mouse embryonic and adult fibroblast cultures by defined factors. Cell. Aug. 25, 2006;126(4):663-76.
Abad et al., Reprogramming in vivo produces teratomas and iPS cells with totipotency features. Nature. 2013;502(7471):340-345.
Ahfeldt et al., Programming human pluripotent stem cells into white and brown adipocytes. Nat Cell Biol. Jan. 15, 2012;14(2):209-19.
Alle et al., A single short reprogramming early in life improves fitness and increases lifespan in old age. bioRxiv, https://doi.org/10.1101/2021.05.13.443979. 56 pages, May 14, 2021.
Amieux et al., Cyclic nucleotides converge on brown adipose tissue differentiation. Sci Signal. Jan. 12, 2010;3(104):pe2. 3 pages.
Ancey et al., Secretion of IL-6, IL-11 and LIF by human cardiomyocytes in primary culture. Cytokine. May 21, 2002;18(4):199-205.
Armulik et al., Pericytes regulate the blood-brain barrier. Nature. Nov. 25, 2010;468(7323):557-61.
Armulik et al., Pericytes: developmental, physiological, and pathological perspectives, problems, and promises. Dev Cell. Aug. 16, 2011;21(2):193-215.
Bai et al., BMP4 regulates vascular progenitor development in human embryonic stem cells through a Smad-dependent pathway. J Cell Biochem. Feb. 1, 2010;109(2):363-74.
Beranger et al., In vitro brown and "brite"/"beige" adipogenesis: human cellular models and molecular aspects. Biochim Biophys Acta. May 2013;1831(5):905-14.
Bergers et al., The role of pericytes in blood-vessel formation and maintenance. Neuro Oncol. Oct. 2005;7(4):452-64.
Beyret et al., Elixir of Life: Thwarting Aging With Regenerative Reprogramming. Circ Res. Jan. 5, 2018;122(1):128-141.
Bian et al., Extracellular vesicles derived from human bone marrow mesenchymal stem cells promote angiogenesis in a rat myocardial infarction model. J Mol Med (Berl). Apr. 2014;92(4):387-97.
Bignone et al., Identification of human embryonic progenitor cell targeting peptides using phage display. PLoS One. 2013;8(3):e58200. 12 pages.
Birbrair et al., Role of pericytes in skeletal muscle regeneration and fat accumulation. Stem Cells Dev. Aug. 15, 2013;22(16):2298-314.
Birbrair et al., Type-2 pericytes participate in normal and tumoral angiogenesis. Am J Physiol Cell Physiol. Jul. 1, 2014;307(1):C25-38.
Blanpain et al., Stem cells assessed. Nat Rev Mol Cell Biol. Jun. 8, 2012;13(7):471-6.
Blocki et al., Not all MSCs can act as pericytes: functional in vitro assays to distinguish pericytes from other mesenchymal stem cells in angiogenesis. Stem Cells Dev. Sep. 1, 2013;22(17):2347-55.
Bloom et al., Disodium (R,R)-5-[2-[[2-(3-chlorophenyl)-2-hydroxyethyl]-amino] propyl]-1,3-benzodioxole-2,2-dicarboxylate (CL 316,243). A potent beta-adrenergic agonist virtually specific for beta 3 receptors. A promising antidiabetic and antiobesity agent. J Med Chem. Aug. 7, 1992;35(16):3081-4.
Blum et al., The tumorigenicity of diploid and aneuploid human pluripotent stem cells. Cell Cycle. Dec. 2009;8(23):3822-30.
Bodnar et al., Extension of life-span by introduction of telomerase into normal human cells. Science. 1998;279(5349):349-352.
Bogos et al., VEGFR-3-positive circulating lymphatic/vascular endothelial progenitor cell level is associated with poor prognosis in human small cell lung cancer. Clin Cancer Res. Mar. 1, 2009;15(5):1741-6.
Bongso et al., Improved quality of human embryos when co-cultured with human ampullary cells. Hum Reprod. Aug. 1989;4(6):706-13.
Bongso et al., Isolation and culture of inner cell mass cells from human blastocysts. Hum Reprod. Nov. 1994;9(11):2110-7.
Bruno et al., Mesenchymal stem cell-derived microvesicles protect against acute tubular injury. J Am Soc Nephrol. May 2009;20(5):1053-67.
Camussi et al., Exosomes/microvesicles as a mechanism of cell-to-cell communication. Kidney Int. Nov. 2010;78(9):838-48.
Cannon et al., Brown adipose tissue: function and physiological significance. Physiol Rev. Jan. 2004;84(1):277-359.
Cannon et al., Cultures of adipose precursor cells from brown adipose tissue and of clonal brown-adipocyte-like cell lines. Methods Mol Biol. 2001;155:213-24.
Carmeliet, Angiogenesis in life, disease and medicine. Nature. Dec. 15, 2005;438(7070):932-6.
Chakritbudsabong et al., Exogenous LIN28 Is Required for the Maintenance of Self-Renewal and Pluripotency in Presumptive Porcine-Induced Pluripotent Stem Cells. Front Cell Dev Biol. Jul. 20, 2021;9:709286, 16 pages.
Cheema et al., Regulation and guidance of cell behavior for tissue regeneration via the siRNA mechanism. Wound Repair Regen. May-Jun. 2007;15(3):286-95.
Chen et al., A model of focal ischemic stroke in the rat: reproducible extensive cortical infarction. Stroke. Jul.-Aug. 1986;17(4):738-43.
Chen et al., Advances in the developmental origin of brown adipocyte. Chinese Bulletin of Life Sciences. Jul. 2013;25(7):661-668.
Chen et al., Enabling a robust scalable manufacturing process for therapeutic exosomes through oncogenic immortalization of human ESC-derived MSCs. J Transl Med. Apr. 25, 2011;9:47. 10 pages.
Chen et al., Human myocardial pericytes: multipotent mesodermal precursors exhibiting cardiac specificity. Stem Cells. Feb. 2015;33(2):557-73.
Chen et al., Human pericytes for ischemic heart repair. Stem Cells. Feb. 2013;31(2):305-16.
Chiavellini et al., Aging and rejuvenation—a modular epigenome model. Aging (Albany NY). Feb. 24, 2021;13(4):4734-4746.
Chuang et al., The fission yeast homologue of Orc4p binds to replication origin DNA via multiple AT-hooks. Proc Natl Acad Sci U S A. 1999;96(6):2656-2661.
Chung et al., Human embryonic stem cell lines generated without embryo destruction. Cell Stem Cell. Feb. 7, 2008;2(2):113-7.
Cibelli et al., Transgenic bovine chimeric offspring produced from somatic cell-derived stem-like cells. Nat Biotechnol. Jul. 1998;16(7):642-6.
Climent et al., TGFbeta Triggers miR-143/145 Transfer From Smooth Muscle Cells to Endothelial Cells, Thereby Modulating Vessel Stabilization. Circ Res. May 22, 2015;116(11):1753-64.
Cohen et al., Turning straw into gold: directing cell fate for regenerative medicine. Nat Rev Genet. Apr. 2011;12(4):243-52.

(56) References Cited

OTHER PUBLICATIONS

Conley et al., BMPs regulate differentiation of a putative visceral endoderm layer within human embryonic stem-cell-derived embryoid bodies. Biochem Cell Biol. Feb. 2007;85(1):121-32.
Cooper et al., Modulation of PGC-1 coactivator pathways in brown fat differentiation through LRP130. J Biol Chem. Nov. 14, 2008;283(46):31960-7.
Corselli et al., Identification of perivascular mesenchymal stromal/stem cells by flow cytometry. Cytometry A. Aug. 2013;83(8):714-20.
Costa et al., The hESC line Envy expresses high levels of GFP in all differentiated progeny. Nat Methods. Apr. 2005;2(4):259-60.
Costa et al., The hESC line Envy expresses high levels of GFP in all differentiated progeny. Nat Methods. Apr. 2005;2(4):259-60. Advance online publication.
Crisan et al., A perivascular origin for mesenchymal stem cells in multiple human organs. Cell Stem Cell. Sep. 11, 2008;3(3):301-13.
Crook et al., The generation of six clinical-grade human embryonic stem cell lines. Cell Stem Cell. Nov. 2007;1(5):490-4.
Cruz et al., Extracellular Vesicles: Decoding a New Language for Cellular Communication in Early Embryonic Development. Front Cell Dev Biol. Aug. 28, 2018;6:94.
Dai et al., MicroRNA-223-3p inhibits the angiogenesis of ischemic cardiac microvascular endothelial cells via affecting RPS6KB1/hif-1a signal pathway. PLoS One. Oct. 14, 2014;9(10):e108468. 14 pages.
Daneman et al., Pericytes are required for blood-brain barrier integrity during embryogenesis. Nature. Nov. 25, 2010;468(7323):562-6.
Dar et al., Multipotent vasculogenic pericytes from human pluripotent stem cells promote recovery of murine ischemic limb. Circulation. Jan. 3, 2012;125(1):87-99.
De Souza Batista et al., Omentin plasma levels and gene expression are decreased in obesity. Diabetes. Jun. 2007;56(6):1655-61.
Dechesne et al., Stem Cells from Human Adipose Tissue: A New Tool for Pharmacological Studies and for Clinical Applications. Adipose Stem Cells and Regenerative Medicine. Y.-G. Illouz (Ed.), Springer-Verlag Berlin Heidelberg. Chapter 12, pp. 121-132, (2011).
Deregibus et al., Endothelial progenitor cell derived microvesicles activate an angiogenic program in endothelial cells by a horizontal transfer of mRNA. Blood. Oct. 1, 2007;110(7):2440-8.
Desandro et al., Associations and interactions between bare lymphocyte syndrome factors. Mol Cell Biol. Sep. 2000;20(17):6587-99.
Dore-Duffy et al., Morphology and properties of pericytes. Methods Mol Biol. 2011;686:49-68.
Dubois et al., SIRPA is a specific cell-surface marker for isolating cardiomyocytes derived from human pluripotent stem cells. Nat Biotechnol. Oct. 23, 2011;29(11):1011-8.
Durick et al., Hunting with traps: genome-wide strategies for gene discovery and functional analysis. Genome Res. Nov. 1999;9(11):1019-25.
Díez et al., Endothelial progenitor cells undergo an endothelial-to-mesenchymal transition-like process mediated by TGFbetaRI. Cardiovasc Res. Dec. 1, 2010;88(3):502-11.
Elabd et al., Human multipotent adipose-derived stem cells differentiate into functional brown adipocytes. Stem Cells. Nov. 2009;27(11):2753-60.
Elali et al., The role of pericytes in neurovascular unit remodeling in brain disorders. Int J Mol Sci. Apr. 16, 2014;15(4):6453-74.
Espandar et al., Adipose-derived stem cells on hyaluronic acid-derived scaffold: a new horizon in bioengineered cornea. Arch Ophthalmol. Feb. 2012;130(2):202-8.
Fedorenko et al., Mechanism of fatty-acid-dependent UCP1 uncoupling in brown fat mitochondria. Cell. Oct. 12, 2012;151(2):400-13.
Ferrari et al., Transforming growth factor-beta 1 (TGF-beta1) induces angiogenesis through vascular endothelial growth factor (VEGF)-mediated apoptosis. J Cell Physiol. May 2009;219(2):449-58.
Fish et al., miR-126 regulates angiogenic signaling and vascular integrity. Dev Cell. Aug. 2008;15(2):272-84.

Follenzi et al., Gene transfer by lentiviral vectors is limited by nuclear translocation and rescued by HIV-1 pol sequences. Nat Genet. Jun. 2000;25(2):217-22.
Forte et al., MicroRNA-mediated transformation by the Kaposi's sarcoma-associated herpesvirus Kaposin locus. J Virol. Feb. 2015;89(4):2333-41.
Francavilla et al., Transient GFER knockdown in vivo impairs liver regeneration after partial hepatectomy. Int J Biochem Cell Biol. Aug. 2014;53:343-51.
French et al., What is a Conservative Substitution? J Mol Evol. 1983;19:171-175.
Fu et al., Endothelial cell O-glycan deficiency causes blood/lymphatic misconnections and consequent fatty liver disease in mice. J Clin Invest. Nov. 2008;118(11):3725-37.
Funk et al., Evaluating the genomic and sequence integrity of human ES cell lines; comparison to normal genomes. Stem Cell Res. Mar. 2012;8(2):154-64.
Gao et al., Endothelial progenitor cells control the angiogenic switch in mouse lung metastasis. Science. Jan. 11, 2008;319(5860):195-8.
Garbuzova-Davis et al., Blood-CNS Barrier Impairment in ALS patients versus an animal model. Front Cell Neurosci. Feb. 3, 2014;8:21. 10 pages.
Garcia et al., Glucose Starvation in Cardiomyocytes Enhances Exosome Secretion and Promotes Angiogenesis in Endothelial Cells. PLoS One. Sep. 22, 2015;10(9):e0138849. 23 pages.
Gardner et al., Culture and transfer of human blastocysts increases implantation rates and reduces the need for multiple embryo transfers. Fertil Steril. Jan. 1998;69(1):84-8.
Gehling et al., In vitro differentiation of endothelial cells from AC133-positive progenitor cells. Blood. May 15, 2000;95(10):3106-12.
GeneCards, ADIPOQ Gene. Retrieved online at: https://www.genecards.org/cgi-bin/carddisp.p?gene=ADIPOQ#protein_expression. 27 pages, 1996-2021.
George et al., Isolation of human platelet membrane microparticles from plasma and serum. Blood. Oct. 1982;60(4):834-40.
Gill et al., Multi-omic rejuvenation of human cells by maturation phase transient reprogramming. bioRxiv, https://doi.org/10.1101/2021.01.15.426786. 25 pages, Jan. 17, 2021.
Goldman et al., A boost of BMP4 accelerates the commitment of human embryonic stem cells to the endothelial lineage. Stem Cells. Aug. 2009;27(8):1750-9.
Golozoubova et al., Only UCP1 can mediate adaptive nonshivering thermogenesis in the cold. Faseb J. Sep. 2001;15(11):2048-50.
Goumans et al., TGF-beta signaling in vascular biology and dysfunction. Cell Res. Jan. 2009;19(1):116-27.
Greenwood-Goodwin et al., A novel lineage restricted, pericyte-like cell line isolated from human embryonic stem cells. Sci Rep. Apr. 25, 2016;6:24403, 10 pages.
Grigolo et al., Transplantation of chondrocytes seeded on a hyaluronan derivative (hyaff-11) into cartilage defects in rabbits. Biomaterials. Sep. 2001;22(17):2417-24.
Grützkau et al., Small but mighty: how the MACS-technology based on nanosized superparamagnetic particles has helped to analyze the immune system within the last 20 years. Cytometry A. Jul. 2010;77(7):643-7.
Guduric-Fuchs et al., Selective extracellular vesicle-mediated export of an overlapping set of microRNAs from multiple cell types. BMC Genomics. Aug. 1, 2012;13:357. 14 pages.
Haflidadóttir et al., Upregulation of miR-96 enhances cellular proliferation of prostate cancer cells through FOXO1. PLoS One. Aug. 12, 2013;8(8):e72400. 11 pages.
Han et al., Induced pluripotent stem cells: emerging techniques for nuclear reprogramming. Antioxid Redox Signal. Oct. 1, 2011;15(7):1799-820.
Harms et al., Brown and beige fat: development, function and therapeutic potential. Nat Med. Oct. 2013;19(10):1252-63.
Hassan et al., Encapsulation and 3D culture of human adipose-derived stem cells in an in-situ crosslinked hybrid hydrogel composed of PEG-based hyperbranched copolymer and hyaluronic acid. Stem Cell Res Ther. Mar. 21, 2013;4(2):32. 11 pages.

(56) References Cited

OTHER PUBLICATIONS

Hedman et al., Isolation of the pericellular matrix of human fibroblast cultures. J Cell Biol. Apr. 1979;81(1):83-91.
Hemmrich et al., Implantation of preadipocyte-loaded hyaluronic acid-based scaffolds into nude mice to evaluate potential for soft tissue engineering. Biomaterials. Dec. 2005;26(34):7025-37.
Heo et al., Spontaneous differentiation of mouse embryonic stem cells in vitro: characterization by global gene expression profiles. Biochem Biophys Res Commun. Jul. 15, 2005;332(4):1061-9.
Herrera et al., Human liver stem cell-derived microvesicles accelerate hepatic regeneration in hepatectomized rats. J Cell Mol Med. Jun. 2010; 14(6B):1605-18.
Ho et al., Synthetic protein transduction domains: enhanced transduction potential in vitro and in vivo. Cancer Res. Jan. 15, 2001;61(2):474-7.
Honda et al., Cartilage formation by cultured chondrocytes in a new scaffold made of poly(L-lactide-epsilon-caprolactone) sponge. J Oral Maxillofac Surg. Jul. 2000;58(7):767-75.
Horvath, DNA methylation age of human tissues and cell types. Genome Biol. 2013;14(10):R115, 20 pages.
Huber et al., Haemangioblast commitment is initiated in the primitive streak of the mouse embryo. Nature. Dec. 2, 2004;432(7017):625-30.
Hynes et al., Micropatterning of 3D Microenvironments for Living Biosensor Applications. Biosensors (Basel). Mar. 2014;4(1):28-44.
Hölig et al., Novel RGD lipopeptides for the targeting of liposomes to integrin-expressing endothelial and melanoma cells. Protein Eng Des Sel. May 2004;17(5):433-41.
Hüttemann et al., Mice deleted for heart-type cytochrome c oxidase subunit 7a1 develop dilated cardiomyopathy. Mitochondrion. Mar. 2012;12(2):294-304.
Ibrahim et al., Exosomes as critical agents of cardiac regeneration triggered by cell therapy. Stem Cell Reports. May 8, 2014;2(5):606-19.
Inman et al., SB-431542 is a potent and specific inhibitor of transforming growth factor-beta superfamily type I activin receptor-like kinase (ALK) receptors ALK4, ALK5, and ALK7. Mol Pharmacol. Jul. 2002;62(1):65-74.
Jackson et al., Recognizing and avoiding siRNA off-target effects for target identification and therapeutic application. Nat Rev Drug Discov. Jan. 2010;9(1):57-67.
Jaiswal et al., Long-term multiple color imaging of live cells using quantum dot bioconjugates. Nat Biotechnol. Jan. 2003;21(1):47-51.
Jakob et al., Role of microRNAs in stem/progenitor cells and cardiovascular repair. Cardiovasc Res. Mar. 15, 2012;93(4):614-22.
James et al., An abundant perivascular source of stem cells for bone tissue engineering. Stem Cells Transl Med. Sep. 2012;1(9):673-84.
James et al., Contribution of human embryonic stem cells to mouse blastocysts. Dev Biol. Jul. 1, 2006;295(1):90-102.
James et al., Expansion and maintenance of human embryonic stem cell-derived endothelial cells by TGFbeta inhibition is Id1 dependent. Nat Biotechnol. Feb. 2010;28(2):161-6.
Jankovic et al., Id1 restrains myeloid commitment, maintaining the self-renewal capacity of hematopoietic stem cells. Proc Natl Acad Sci U S A. Jan. 23, 2007;104(4):1260-5.
Jeong et al., Nanovesicles engineered from ES cells for enhanced cell proliferation. Biomaterials. Nov. 2014;35(34):9302-10.
Jun-Hao et al., Lin28 and let-7 in the Metabolic Physiology of Aging. Trends Endocrinol Metab. Mar. 2016;27(3):132-141.
Kaczkowski et al., Transcriptome Analysis of Recurrently Deregulated Genes across Multiple Cancers Identifies New Pan-Cancer Biomarkers. Cancer Res. 2016;76(2):216-226.
Kane et al., Derivation of endothelial cells from human embryonic stem cells by directed differentiation: analysis of microRNA and angiogenesis in vitro and in vivo. Arterioscler Thromb Vasc Biol. Jul. 2010;30(7):1389-97.
Kane et al., Epigenetic changes during aging and their reprogramming potential. Crit Rev Biochem Mol Biol. Feb. 2019;54(1):61-83.
Kang et al., A self-enabling TGFbeta response coupled to stress signaling: Smad engages stress response factor ATF3 for Id1 repression in epithelial cells. Mol Cell. Apr. 2003;11(4):915-26.
Karamanlidis et al., C/EBPbeta reprograms white 3T3-L1 preadipocytes to a Brown adipocyte pattern of gene expression. J Biol Chem. Aug. 24, 2007;282(34):24660-9.
Kashyap et al., Regulation of stem cell pluripotency and differentiation involves a mutual regulatory circuit of the NANOG, OCT4, and SOX2 pluripotency transcription factors with polycomb repressive complexes and stem cell microRNAs. Stem Cells Dev. Sep. 2009;18(7):1093-108.
Kawamoto et al., Role of progenitor endothelial cells in cardiovascular disease and upcoming therapies. Catheter Cardiovasc Interv. Oct. 1, 2007;70(4):477-84.
Kawasaki et al., Vascular Repair by Tissue-Resident Endothelial Progenitor Cells in Endotoxin-Induced Lung Injury. Am J Respir Cell Mol Biol. Oct. 2015;53(4):500-12.
Kazantzis et al., PAZ6 cells constitute a representative model for human brown pre-adipocytes. Front Endocrinol (Lausanne). Feb. 2, 2012;3:13.
Keller et al., Exosomes: from biogenesis and secretion to biological function. Immunol Lett. Nov. 15, 2006;107(2):102-8.
Kelly et al., Signaling hierarchy regulating human endothelial cell development. Arterioscler Thromb Vasc Biol. May 2009;29(5):718-24.
Khakoo et al., Endothelial progenitor cells. Annu Rev Med. 2005;56:79-101.
Kim et al., Extracellular membrane vesicles from tumor cells promote angiogenesis via sphingomyelin. Cancer Res. Nov. 1, 2002;62(21):6312-7.
Kim et al., Specific association of human telomerase activity with immortal cells and cancer. Science. 1994;266(5193):2011-2015.
King et al., Hypoxic enhancement of exosome release by breast cancer cells. BMC Cancer. Sep. 24, 2012;12:421. 10 pages.
Korchagin, Neoplastic Diseases Reviews, Stem Cells. CancerLink.ru. 26 pages, (2011).
Krosl et al., In vitro expansion of hematopoietic stem cells by recombinant TAT-HOXB4 protein. Nat Med. Nov. 2003;9(11):1428-32.
Kucharzewska et al., Exosomes reflect the hypoxic status of glioma cells and mediate hypoxia-dependent activation of vascular cells during tumor development. PNAS. Apr. 30, 2013;110(18):7312-7317.
Lai et al., Animal models of diabetic retinopathy: summary and comparison. J Diabetes Res. 2013;2013:106594. 29 pages.
Laine et al., MicroRNAs miR-96, miR-124, and miR-199a regulate gene expression in human bone marrow-derived mesenchymal stem cells. J Cell Biochem. Aug. 2012;113(8):2687-95.
Lanza et al., Extension of cell life-span and telomere length in animals cloned from senescent somatic cells. Science. 2000;288(5466):665-669.
Lanza et al., Human therapeutic cloning. Nat Med. Sep. 1999;5(9):975-7.
Laping et al., Inhibition of transforming growth factor (TGF)-beta1-induced extracellular matrix with a novel inhibitor of the TGF-beta type I receptor kinase activity: SB-431542. Mol Pharmacol. Jul. 2002;62(1):58-64.
Laposa, Stem cells for drug screening. J Cardiovasc Pharmacol. Sep. 2011;58(3):240-5.
Le Grand et al., Six1 regulates stem cell repair potential and self-renewal during skeletal muscle regeneration. J Cell Biol. Sep. 3, 2012;198(5):815-32.
Ledford, Reversal of biological clock restores vision in old mice. Nature. Dec. 2020;588(7837):209.
Lee et al., Deletion of heart-type cytochrome c oxidase subunit 7a1 impairs skeletal muscle angiogenesis and oxidative phosphorylation. J Physiol. Oct. 15, 2012;590(20):5231-43.
Lee et al., Exosomes mediate the cytoprotective action of mesenchymal stromal cells on hypoxia-induced pulmonary hypertension. Circulation. Nov. 27, 2012;126(22):2601-11.
Lee et al., HLA-E is a major ligand for the natural killer inhibitory receptor CD94/NKG2A. Proc Natl Acad Sci U S A. Apr. 28, 1998;95(9):5199-204.

(56) References Cited

OTHER PUBLICATIONS

Levenberg et al., Endothelial cells derived from human embryonic stem cells. Proc Natl Acad Sci U S A. Apr. 2, 2002;99(7):4391-6.

Levenberg et al., Endothelial potential of human embryonic stem cells. Blood. Aug. 1, 2007;110(3):806-14.

Li et al., Comparison of reporter gene and iron particle labeling for tracking fate of human embryonic stem cells and differentiated endothelial cells in living subjects. Stem Cells. Apr. 2008;26(4):864-73.

Limbourg et al., Evaluation of postnatal arteriogenesis and angiogenesis in a mouse model of hind-limb ischemia. Nat Protoc. 2009;4(12):1737-48.

Lin et al., Quantum dot imaging for embryonic stem cells. BMC Biotechnol. Oct. 9, 2007;7:67. 10 pages.

Lin et al., Unregulated miR-96 induces cell proliferation in human breast cancer by downregulating transcriptional factor FOXO3a. PLoS One. Dec. 23, 2010;5(12):e15797. 10 pages.

Liu et al., CD31: beyond a marker for endothelial cells. Cardiovasc Res. Apr. 1, 2012;94(1):3-5.

Liu et al., MiR-106b and MiR-15b modulate apoptosis and angiogenesis in myocardial infarction. Cell Physiol Biochem. 2012;29(5-6):851-62.

Lopatina et al., Platelet-derived growth factor regulates the secretion of extracellular vesicles by adipose mesenchymal stem cells and enhances their angiogenic potential. Cell Commun Signal. Apr. 11, 2014;12:26. 12 pages.

Lu et al., Generation of functional hemangioblasts from human embryonic stem cells. Nat Methods. Jun. 2007;4(6):501-9.

Lu et al., Reprogramming to recover youthful epigenetic information and restore vision. Nature. Dec. 2020;588(7836):124-129.

Lu et al., Reversal of ageing- and injury-induced vision loss by Tet-dependent epigenetic reprogramming. bioRxiv, retrieved nline at: https://www.biorxiv.org/content/10.1101/710210v1.full.pdf. 51 pages, Jul. 31, 2019.

Lu et al., Targeting of embryonic stem cells by peptide-conjugated quantum dots. PLoS One. Aug. 1, 2010;5(8):e12075. 10 pages.

Lyden et al., Impaired recruitment of bone-marrow-derived endothelial and hematopoietic precursor cells blocks tumor angiogenesis and growth. Nat Med. Nov. 2001;7(11):1194-201.

Mali et al., Improved efficiency and pace of generating induced pluripotent stem cells from human adult and fetal fibroblasts. Stem Cells. Aug. 2008;26(8):1998-2005.

Marion et al., Common Telomere Changes during In Vivo Reprogramming and Early Stages of Tumorigenesis. Stem Cell Reports. 2017;8(2):460-475.

Martinez et al., Shed membrane microparticles from circulating and vascular cells in regulating vascular function. Am J Physiol Heart Circ Physiol. Mar. 2005;288(3):H1004-9.

Martinez-Redondo et al., Tailored chromatin modulation to promote tissue regeneration. Semin Cell Dev Biol. Jan. 2020;97:3-15, pre-publication edition.

Menendez et al., Metabolic control of cancer cell stemness: Lessons from iPS cells. Cell Cycle. 2015;14(24):3801-11.

Molek et al., Peptide phage display as a tool for drug discovery: targeting membrane receptors. Molecules. Jan. 21, 2011;16(1):857-87.

Mosteiro et al., Tissue damage and senescence provide critical signals for cellular reprogramming in vivo. Science. Nov. 25, 2016;354(6315):aaf4445, 12 pages.

Nakagawa et al., Reprogramming of somatic cells to pluripotency. Adv Exp Med Biol. 2010;695:215-24.

Nakashiba et al., Netrin-G1: a novel glycosyl phosphatidylinositol-linked mammalian netrin that is functionally divergent from classical netrins. J Neurosci. Sep. 1, 2000;20(17):6540-50.

Naldini et al., In vivo gene delivery and stable transduction of nondividing cells by a lentiviral vector. Science. Apr. 12, 1996;272(5259):263-7.

Nedergaard et al., PPARgamma in the control of brown adipocyte differentiation. Biochim Biophys Acta. May 30, 2005;1740(2):293-304.

Nelson et al., Induced pluripotent stem cells: advances to applications. Stem Cells Cloning. Jan. 1, 2010;3:29-37.

Nguyen et al., Lin28 and let-7 in cell metabolism and cancer. Transl Pediatr. Jan. 2015;4(1):4-11.

Nicoli et al., MicroRNA-mediated integration of haemodynamics and Vegf signalling during angiogenesis. Nature. Apr. 22, 2010;464(7292):1196-200.

Niemelä et al., Molecular identification of PAL-E, a widely used endothelial-cell marker. Blood. Nov. 15, 2005;106(10):3405-9.

Nishio et al., Production of functional classical brown adipocytes from human pluripotent stem cells using specific hemopoietin cocktail without gene transfer. Cell Metab. Sep. 5, 2012;16(3):394-406.

Nonaka et al., Development of stabilin2+ endothelial cells from mouse embryonic stem cells by inhibition of TGFbeta/activin signaling. Biochem Biophys Res Commun. Oct. 17, 2008;375(2):256-60.

Nourse et al., VEGF induces differentiation of functional endothelium from human embryonic stem cells: implications for tissue engineering. Arterioscler Thromb Vasc Biol. Jan. 2010;30(1):80-9.

Nowakowski et al., Genetic engineering of stem cells for enhanced therapy. Acta Neurobiol Exp (Wars). 2013;73(1):1-18.

Ocampo et al., In Vivo Amelioration of Age-Associated Hallmarks by Partial Reprogramming. Cell. 2016; 167(7):1719-1733.e12.

Odaka, Localization of mesenchymal cells in adult mouse thymus: their abnormal distribution in mice with disorganization of thymic medullary epithelium. J Histochem Cytochem. Apr. 2009;57(4):373-82.

Ohno et al., PPAR agonists induce a white-to-brown fat conversion through stabilization of PRDM16 protein. Cell Metab. Mar. 7, 2012;15(3):395-404.

Ohshima et al., Let-7 microRNA family is selectively secreted into the extracellular environment via exosomes in a metastatic gastric cancer cell line. PLoS One. Oct. 2010 8;5(10):e13247. 10 pages.

Olova et al., Partial reprogramming induces a steady decline in epigenetic age before loss of somatic identity. Aging Cell. 2019;18(1):e12877, 7 pages.

Ong et al., Cross talk of combined gene and cell therapy in ischemic heart disease: role of exosomal microRNA transfer. Circulation. Sep. 9, 2014;130(11 Suppl 1):S60-9.

Orlova et al., Functionality of endothelial cells and pericytes from human pluripotent stem cells demonstrated in cultured vascular plexus and zebrafish xenografts. Arterioscler Thromb Vasc Biol. Jan. 2014;34(1):177-86.

Pankratz et al., MicroRNA-155 Exerts Cell-Specific Antiangiogenic but Proarteriogenic Effects During Adaptive Neovascularization. Circulation. May 5, 2015;131(18):1575-89.

Parisi et al., Identification of RNA-binding proteins that partner with Lin28a to regulate Dnmt3a expression. Sci Rep. Jan. 27, 2021;11(1):2345, 13 pages.

Patel et al., Poly(ethylene glycol) hydrogel system supports preadipocyte viability, adhesion, and proliferation. Tissue Eng. Sep.-Oct. 2005;11(9-10):1498-505.

Peichev et al., Expression of VEGFR-2 and AC133 by circulating human CD34(+) cells identifies a population of functional endothelial precursors. Blood. Feb. 1, 2000;95(3):952-8.

Perka et al., Joint cartilage repair with transplantation of embryonic chondrocytes embedded in collagen-fibrin matrices. Clin Exp Rheumatol. Jan.-Feb. 2000;18(1):13-22.

Prestwich et al., The translational imperative: making cell therapy simple and effective. Acta Biomater. Dec. 2012;8(12):4200-7.

Rafii et al., Cancer. A few to flip the angiogenic switch. Science. Jan. 11, 2008;319(5860):163-4.

Ragni et al., Adipogenic potential in human mesenchymal stem cells strictly depends on adult or foetal tissue harvest. Int J Biochem Cell Biol. Nov. 2013;45(11):2456-66.

Ramskold et al., An abundance of ubiquitously expressed genes revealed by tissue transcriptome sequence data. PLoS Comput Biol. 2009;5(12):e1000598, 11 pages.

Rando et al., Aging, rejuvenation, and epigenetic reprogramming: resetting the aging clock. Cell. Jan. 20, 2012;148(1-2):46-57.

(56) References Cited

OTHER PUBLICATIONS

Rasmussen et al., TNFerade Biologic: preclinical toxicology of a novel adenovector with a radiation-inducible promoter, carrying the human tumor necrosis factor alpha gene. Cancer Gene Ther. Nov. 2002;9(11):951-7.
Religa et al., Presence of bone marrow-derived circulating progenitor endothelial cells in the newly formed lymphatic vessels. Blood. Dec. 15, 2005;106(13):4184-90.
Reubinoff et al., Embryonic stem cell lines from human blastocysts: somatic differentiation in vitro. Nat Biotechnol. Apr. 2000;18(4):399-404.
Rhie et al., Implantation of Cultured Preadipocyte Using Chitosan/Alginate Sponge. Key Engineering Materials. 2007;342-343;349-352.
Riolobos et al., HLA engineering of human pluripotent stem cells. Mol Ther. Jun. 2013;21(6):1232-41.
Romer-Seibert et al., The RNA-binding protein LIN28 controls progenitor and neuronal cell fate during postnatal neurogenesis. FASEB J. Mar. 2019;33(3):3291-3303, pre-publication edition.
Rong et al., A scalable approach to prevent teratoma formation of human embryonic stem cells. J Biol Chem. Sep. 21, 2012;287(39):32338-45.
Rong et al., An effective approach to prevent immune rejection of human ESC-derived allografts. Cell Stem Cell. Jan. 2, 2014;14(1):121-30.
Rosensteel et al., COL1A1 oligodeoxynucleotides decoy: biochemical and morphologic effects in an acute wound repair model. Exp Mol Pathol. Dec. 2010;89(3):307-13.
Rosler et al., Long-term culture of human embryonic stem cells in feeder-free conditions. Dev Dyn. Feb. 2004;229(2):259-74.
Rossig et al., Histone deacetylase activity is essential for the expression of HoxA9 and for endothelial commitment of progenitor cells. J Exp Med. Jun. 6, 2005;201(11):1825-35.
Roth et al., Telomerase levels control the lifespan of human T lymphocytes. Blood. 2003;102(3):849-857.
Roux et al., Partial reprogramming restores youthful gene expression through transient suppression of cell identity. bioRxiv. https://doi.org/10.1101/2021.05.21.444556. 29 pages, May 23, 2021.
Rudert et al., Bioartificial Cartilage. Cells Tissues Organs. 2000;167:95-105.
Ruzinova et al., Id proteins in development, cell cycle and cancer. Trends Cell Biol. Aug. 2003;13(8):410-8.
Sagare et al., Pericyte loss influences Alzheimer-like neurodegeneration in mice. Nat Commun. 2013;4:2932. 14 pages.
Sahoo et al., Exosomes from human CD34(+) stem cells mediate their proangiogenic paracrine activity. Circ Res. Sep. 16, 2011;109(7):724-8.
Salven et al., VEGFR-3 and CD133 identify a population of CD34+ lymphatic/vascular endothelial precursor cells. Blood. Jan. 1, 2003;101(1):168-72.
Sarkar et al., Transient non-integrative expression of nuclear reprogramming factors promotes multifaceted amelioration of aging in human cells. Nat Commun. Mar. 24, 2020;11(1):1545, 12 pages.
Schnerch et al., Distinguishing between mouse and human pluripotent stem cell regulation: the best laid plans of mice and men. Stem Cells. Mar. 31, 2010;28(3):419-30.
Schniedermann et al., Mouse lung contains endothelial progenitors with high capacity to form blood and lymphatic vessels. BMC Cell Biology. 2010;11(50):1-13.
Schulz et al., Identification of inducible brown adipocyte progenitors residing in skeletal muscle and white fat. Proc Natl Acad Sci U S A. Jan. 4, 2011;108(1):143-8.
Schwarze et al., In vivo protein transduction: intracellular delivery of biologically active proteins, compounds and DNA. Trends Pharmacol Sci. Feb. 2000;21(2):45-8.
Scott et al., Current methods of adipogenic differentiation of mesenchymal stem cells. Stem Cells Dev. Oct. 2011;20(10):1793-804.
Seale et al., PRDM16 controls a brown fat/skeletal muscle switch. Nature. Aug. 21, 2008;454(7207):961-7.
Seandel et al., Generation of a functional and durable vascular niche by the adenoviral E4ORF1 gene. Proc Natl Acad Sci U S A. Dec. 9, 2008;105(49):19288-93.
Semo et al., The 106b~25 microRNA cluster is essential for neovascularization after hindlimb ischaemia in mice. Eur Heart J. Dec. 1, 2014;35(45):3212-23.
Shah et al., Labeling of mesenchymal stem cells by bioconjugated quantum dots. Nano Lett. Oct. 2007;7(10):3071-9.
Shehzad et al., Adiponectin: regulation of its production and its role in human diseases. Hormones (Athens). Jan.-Mar. 2012;11(1):8-20.
Shyh-Chang et al., Lin28 enhances tissue repair by reprogramming cellular metabolism. Cell. 2013;155(4):778-792.
Slotkin et al., In vivo quantum dot labeling of mammalian stem and progenitor cells. Dev Dyn. Dec. 2007;236(12):3393-401.
Sobrino et al., The increase of circulating endothelial progenitor cells after acute ischemic stroke is associated with good outcome. Stroke. Oct. 2007;38(10):2759-64.
Solter et al., Immunosurgery of mouse blastocyst. Proc Natl Acad Sci U S A. Dec. 1975;72(12):5099-102.
Sone et al., Pathway for differentiation of human embryonic stem cells to vascular cell components and their potential for vascular regeneration. Arterioscler Thromb Vasc Biol. Oct. 2007;27(10):2127-34.
Song et al., Modeling disease in human ESCs using an efficient BAC-based homologous recombination system. Cell Stem Cell. Jan. 8, 2010;6(1):80-9.
Spear et al., Isolation, characterization, and recovery of small peptide phage display epitopes selected against viable malignant glioma cells. Cancer Gene Ther. Jul. 2001;8(7):506-11.
Spinetti et al., MicroRNA-15a and microRNA-16 impair human circulating proangiogenic cell functions and are increased in the proangiogenic cells and serum of patients with critical limb ischemia. Circ Res. Jan. 18, 2013;112(2):335-46.
Sternberg et al., A human embryonic stem cell-derived clonal progenitor cell line with chondrogenic potential and markers of craniofacial mesenchyme. Regen Med. Jul. 2012;7(4):481-501.
Sternberg et al., Human Embryonic Stem Cell-derived Clonal Brown Adipocyte Progenitors. BioTime, Inc. Poster Presentation. 1 page.
Stojkovic et al., An autogeneic feeder cell system that efficiently supports growth of undifferentiated human embryonic stem cells. Stem Cells. Mar. 2005;23(3):306-14.
Suva et al., Epigenetic reprogramming in cancer. Science. Mar. 29, 2013;339(6127):1567-70.
Suzuki et al., BMPs promote proliferation and migration of endothelial cells via stimulation of VEGF-A/VEGFR2 and angiopoietin-1/Tie2 signalling. J Biochem. Feb. 2008;143(2):199-206.
Suárez et al., MicroRNAs as novel regulators of angiogenesis. Circ Res. Feb. 27, 2009;104(4):442-54.
Svensson et al., Gene expression in human brown adipose tissue. Int J Mol Med. Feb. 2011;27(2):227-32.
Tadokoro et al., Exosomes derived from hypoxic leukemia cells enhance tube formation in endothelial cells. J Biol Chem. Nov. 29, 2013;288(48):34343-51.
Takahashi et al., Induction of pluripotent stem cells from adult human fibroblasts by defined factors. Cell. Nov. 30, 2007;131(5):861-72.
Tchkonia et al., Fat depot origin affects adipogenesis in primary cultured and cloned human preadipocytes. Am J Physiol Regul Integr Comp Physiol. May 2002;282(5):R1286-96.
Tchkonia et al., Identification of depot-specific human fat cell progenitors through distinct expression profiles and development gene patterns. Am J Physiol Endocrinol Metab. 2007;292:E298-E307.
Teesalu et al., Mapping of vascular ZIP codes by phage display. Methods Enzymol. 2012;503:35-56.
Thery et al., Isolation and characterization of exosomes from cell culture supernatants and biological fluids. Curr Protoc Cell Biol. Apr. 2006;Chapter 3:Unit 3.22.1-3.22.29.
Thomson et al., Embryonic stem cell lines derived from human blastocysts. Science. Nov. 6, 1998;282(5391):1145-7.
Thomson et al., Isolation of a primate embryonic stem cell line. Proc Natl Acad Sci U S A. Aug. 15, 1995;92(17):7844-8.

(56) References Cited

OTHER PUBLICATIONS

Thomson et al., Primate embryonic stem cells. Curr Top Dev Biol. 1998;38:133-65.
Thumser et al., Fatty acid binding proteins: tissue-specific functions in health and disease. Curr Opin Clin Nutr Metab Care. Mar. 2014;17(2): 124-9.
Tiscornia et al., Diseases in a dish: modeling human genetic disorders using induced pluripotent cells. Nat Med. Dec. 2011;17(12):1570-6.
Tsialikas et al., LIN28: roles and regulation in development and beyond. Development. Jul. 15, 2015;142(14):2397-404.
Tsuchida et al., Inhibitors of the TGF-beta superfamily and their clinical applications. Mini Rev Med Chem. Nov. 2006;6(11):1255-61.
Vadla, lin-28 controls the succession of cell fate choices via two distinct activities. PLoS Genet. 2012;8(3):e1002588, 11 pages.
Van Der Lans et al., Cold-activated brown adipose tissue in human adults: methodological issues. Am J Physiol Regul Integr Comp Physiol. Jul. 15, 2014;307(2):R103-13.
Vaziri et al., Spontaneous reversal of the developmental aging of normal human cells following transcriptional reprogramming. Regen Med. 2010;5(3):345-363.
Viswanathan et al., Lin28 promotes transformation and is associated with advanced human malignancies. Nat Genet. Jul. 2009;41(7):843-8.
Viswanathan et al., Lin28: A microRNA regulator with a macro role. Cell. Feb. 19, 2010;140(4):445-9.
Wagner et al., Replicative senescence of mesenchymal stem cells: a continuous and organized process. PLoS One. May 21, 2008;3(5):e2213. 12 pages.
Wang et al., Endothelial cells derived from human embryonic stem cells form durable blood vessels in vivo. Nat Biotechnol. Mar. 2007;25(3):317-8.
Wang et al., Lin28 Signaling Supports Mammalian PNS and CNS Axon Regeneration. Cell Rep. Sep. 4, 2018;24(10):2540-2552.
Wanjare et al., Defining differences among perivascular cells derived from human pluripotent stem cells. Stem Cell Reports. Apr. 17, 2014;2(5):561-75.
Watabe et al., TGF-beta receptor kinase inhibitor enhances growth and integrity of embryonic stem cell-derived endothelial cells. J Cell Biol. Dec. 22, 2003;163(6):1303-11.
Watabe et al., TGF-beta Signaling in Embryonic Stem Cell-Derived Endothelial Cells. Methods in Molecular Biology, vol. 330: Embryonic Stem Cell Protocols, 2nd Edition: vol. 2. K. Turksen (Ed.) Humana Press Inc., Totowa, NJ. Chapter 23, pp. 341-351, (2006).
Watt et al., Human endothelial stem/progenitor cells, angiogenic factors and vascular repair. J R Soc Interface. Dec. 6, 2010;7 Suppl 6:S731-51.
West et al., Clonal derivation of white and brown adipocyte progenitor cell lines from human pluripotent stem cells. Stem Cell Res Ther. Jan. 8, 2019;10(1):7, 18 pages.
West et al., The ACTCellerate initiative: large-scale combinatorial cloning of novel human embryonic stem cell derivatives. Regen Med. May 2008;3(3):287-308.
West et al., Use of deep neural network ensembles to identify embryonic-fetal transition markers: repression of COX7A1 in embryonic and cancer cells. Oncotarget. Dec. 28, 2017;9(8):7796-7811.
Wilbert et al., LIN28 binds messenger RNAs at GGAGA motifs and regulates splicing factor abundance. Mol Cell. Oct. 26, 2012;48(2):195-206.
Wilcock et al., Vascular amyloid alters astrocytic water and potassium channels in mouse models and humans with Alzheimer's disease. Neuroscience. Mar. 31, 2009;159(3):1055-69.
Winkler et al., Blood-spinal cord barrier breakdown and pericyte reductions in amyotrophic lateral sclerosis. Acta Neuropathol. Jan. 2013;125(1):111-20.
Wong et al., Pericytes, mesenchymal stem cells and their contributions to tissue repair. Pharmacol Ther. Jul. 2015;151:107-20.
Wu et al., Beige adipocytes are a distinct type of thermogenic fat cell in mouse and human. Cell. Jul. 20, 2012;150(2):366-76.
Wu et al., Molecular characterization, expression patterns and polymorphism analysis of porcine Six1 gene. Mol Biol Rep. Apr. 2011;38(4):2619-32.
Xin et al., Systemic administration of exosomes released from mesenchymal stromal cells promote functional recovery and neurovascular plasticity after stroke in rats. J Cereb Blood Flow Metab. Nov. 2013;33(11):1711-5.
Xu et al., BMP4 initiates human embryonic stem cell differentiation to trophoblast. Nat Biotechnol. Dec. 2002;20(12):1261-4.
Xu et al., Feeder-free growth of undifferentiated human embryonic stem cells. Nat Biotechnol. Oct. 2001;19(10):971-4.
Yamahara et al., Augmentation of neovascularization in hindlimb ischemia by combined transplantation of human embryonic stem cells-derived endothelial and mural cells. PLoS One. Feb. 27, 2008;3(2):e1666. 11 pages.
Yamamoto et al., Circulating adiponectin levels and risk of type 2 diabetes in the Japanese. Nutr Diabetes. Aug. 18, 2014;4:e130. 5 pages.
Yamashita et al., Flk1-positive cells derived from embryonic stem cells serve as vascular progenitors. Nature. Nov. 2, 2000;408(6808):92-6.
Yang et al., Human cardiovascular progenitor cells develop from a KDR+ embryonic-stem-cell-derived population. Nature. May 22, 2008;453(7194):524-8.
Yemisci et al., Pericyte contraction induced by oxidative-nitrative stress impairs capillary reflow despite successful opening of an occluded cerebral artery. Nat Med. Sep. 2009;15(9):1031-7.
Yingling et al., Development of TGF-beta signalling inhibitors for cancer therapy. Nat Rev Drug Discov. Dec. 2004;3(12):1011-22.
Yoder, Human endothelial progenitor cells. Cold Spring Harb Perspect Med. Jul. 2012;2(7):a006692, 14 pages.
Yu et al., Induced pluripotent stem cell lines derived from human somatic cells. Science. Dec. 21, 2007;318(5858):1917-20.
Yuan et al., Cell-surface marker signatures for the isolation of neural stem cells, glia and neurons derived from human pluripotent stem cells. PLoS One. Mar. 2, 2011;6(3):e17540. 16 pages.
Yuan et al., Exosomes Derived From Pericytes Improve Microcirculation and Protect Blood-Spinal Cord Barrier After Spinal Cord Injury in Mice. Front Neurosci. 2019;13:319, 14 pages.
Zaragoza et al., Animal models of cardiovascular diseases. J Biomed Biotechnol. 2011;2011:497841. 13 pages.
Zernecke et al., Delivery of microRNA-126 by apoptotic bodies induces CXCL12-dependent vascular protection. Sci Signal. Dec. 8, 2009;2(100):ra81.
Zhang et al., LIN28 Regulates Stem Cell Metabolism and Conversion to Primed Pluripotency. Cell Stem Cell. Jul. 7, 2016;19(1):66-80.
Zhang et al., Microvesicles derived from human umbilical cord mesenchymal stem cells stimulated by hypoxia promote angiogenesis both in vitro and in vivo. Stem Cells Dev. Dec. 10, 2012;21(18):3289-97.
Zhao et al., Isolation and initial application of a novel peptide that specifically recognizes the neural stem cells derived from rhesus monkey embryonic stem cells. J Biomol Screen. Jul. 2010;15(6):687-94.
Zhao et al., Novel peptide ligands that bind specifically to mouse embryonic stem cells. Peptides. Nov. 2010;31(11):2027-34.
Zhong et al., Association of serum omentin-1 levels with coronary artery disease. Acta Pharmacol Sin. Jul. 2011;32(7):873-8.
Zhu et al., The Lin28/let-7 axis regulates glucose metabolism. Cell. Sep. 30, 2011;147(1):81-94.
Zilberfarb et al., Human immortalized brown adipocytes express functional beta3-adrenoceptor coupled to lipolysis. J Cell Sci. Apr. 1997; 110 ( Pt 7):801-7.
Zou et al., Two functional microRNA-126s repress a novel target gene p21-activated kinase 1 to regulate vascular integrity in zebrafish. Circ Res. Jan. 21, 2011;108(2):201-9.
Zwaka et al., A germ cell origin of embryonic stem cells? Development. Jan. 2005;132(2):227-33.
International Search Report and Written Opinion for Application No. PCT/US2014/040601, dated Oct. 22, 2014, 8 pages.
Doeser et al., Reduction of Fibrosis and Scar Formation by Partial Reprogramming In Vivo. Stem Cells. Aug. 2018;36(8):1216-1225.

(56) References Cited

OTHER PUBLICATIONS

Yilmazer et al., In vivo reprogramming of adult somatic cells to pluripotency by overexpression of Yamanaka factors. J Vis Exp. Dec. 17, 2013;(82):e50837, 9 pages.
Yoshitsugu et al., Importance of the structuration of cells in the differentiation process of human induced pluripotent stem(hiPS) cells. Effect of the size of embryoid body on cardionyocyte differentiation of hiPS cells. The Chemical Times. 2016;241:12-16.
U.S. Appl. No. 14/625,621, filed Feb. 18, 2015, U.S. Pat. No. 11,078,462, Issued.
U.S. Appl. No. 14/748,215, filed Jun. 23, 2015, U.S. Pat. No. 10,240,127, Issued.
U.S. Appl. No. 16/270,295, filed Feb. 7, 2019, U.S. Pat. No. 11,274,281, Issued.
U.S. Appl. No. 17/592,200, filed Feb. 3, 2022, 2022-0403341, Published.
U.S. Appl. No. 16/211,690, filed Dec. 6, 2018, 2019-0175691, Published.
U.S. Appl. No. 17/543,020, filed Dec. 6, 2021, 2022-0088138, Published.
U.S. Appl. No. 17/542,997, filed Dec. 6, 2021, 2022-0088137, Published.
U.S. Appl. No. 14/896,664, filed Dec. 7, 2015, U.S. Pat. No. 10,961,531, Issued.
U.S. Appl. No. 13/519,473, filed Jun. 27, 2012, 2012-0301443, Published.
U.S. Appl. No. 13/477,002, filed May 21, 2012, 2012-0295347, Abandoned.
U.S. Appl. No. 14/625,621, U.S. Pat. No. 11,078,462, filed Feb. 18, 2015, 11,078,462, Issued.
U.S. Appl. No. 17/361,611, filed Jun. 29, 2021, 2022-0098554, Published.
U.S. Appl. No. 14/748,215, U.S. Pat. No. 10,240,127 filed Jun. 23, 2015, 10,240,127, Issued.
U.S. Appl. No. 16/270,295, U.S. Pat. No. 11,274,281 filed Feb. 7, 2019, 11,274,281, Issued.
U.S. Appl. No. 17/592,200, filed Feb. 3, 2022, 2022, 2022-0403341, Published.
U.S. Appl. No. 16/211,690, filed Dec. 6, 2018, 2019-0175691, Abandoned.
U.S. Appl. No. 17/543,020, filed Dec. 6, 2021, 2022-0088138, Abandoned.
U.S. Appl. No. 17/542,992, filed Dec. 6, 2021, 2022-0160833, Published.
U.S. Appl. No. 17/542,997, filed Dec. 6, 2021, 2022-0088137, Abandoned.
U.S. Appl. No. 14/896,664, filed Dec. 7, 2015, 10,961,531, Issued.
U.S. Appl. No. 17/543,018, filed Dec. 6, 2021, 2022-0090078, Published.
U.S. Appl. No. 14/554,019, filed Nov. 25, 2014, 2015-0275177, Abandoned.
U.S. Appl. No. 17/825,112, filed May 26, 2022, 2023-0093399, Published.
U.S. Appl. No. 15/994,302, filed May 31, 2018, 2020-0157505, Published.
U.S. Appl. No. 16/012,487, filed Jun. 19, 2018, 2019-0151372, Abandoned.
U.S. Appl. No. 17/592,184, filed Feb. 3, 2022, 2022-0401494, Published.
Ghosh et al., Vector Systems for Gene Therapy: A Comprehensive Literature Review of Progress and Biosafety Challenges. Appl Biosaf. Mar. 1, 2020;25(1):7-18.
Haghighi et al., bFGF-mediated pluripotency maintenance in human induced pluripotent stem cells is associated with NRAS-MAPK signaling. Cell Commun Signal. Dec. 5, 2018;16(1):96, 14 pages.

* cited by examiner

Figure 1 A. TR Inhibitor Genes Expressed in Fetal and Adult Cells

| Gene Symbol | Accession Number | Illumina Probe Number |
|---|---|---|
| COMT | NM_007310.1 | 6940243 |
| TRIM4 | NM_033091.1 | 2810674 |
| CAT | NM_001752.2 | 1770500 |
| PSMD5 | NM_005047.2 | 3060750 |
| SHMT1 | NM_004169.3 | 2690528 |
| LOC205251 | XR_017711.1 | 4180431 |
| ZNF280D | NM_001002843.1 | 1990280 |
| S100A6 | NM_014624.3 | 2810315 |
| MGMT | NM_002412.2 | 6480494 |
| ZNF280D | NM_001002844.1 | 770605 |
| DYNLT3 | NM_006520.1 | 7330044 |
| NAALADL1 | NM_005468.2 | 4120626 |
| COX7A1 | NM_001864.2 | 5390138 |
| TSPYL5 | NM_033512.2 | 770132 |
| IAH1 | NM_001039613.1 | 1300743 |
| C18orf56 | NM_001012716.1 | 1450682 |
| RPS7 | NM_001011.3 | 2690608 |
| FDPS | NM_002004.2 | 6900398 |
| ELOVL6 | NM_024090.1 | 7380181 |
| INSIG1 | NM_198336.1 | 1820332 |
| ACAT2 | NM_005891.2 | 7330753 |
| MAOA | NM_000240.2 | 6550528 |

B. TR Activator Genes Expressed in Embryonic Cells

| Gene Symbol | Accession Number | Illumina Probe Number |
|---|---|---|
| PCDHB2 | NM_018936.2 | 7570753 |
| PCDHB17 | NR_001280.1 | 3520719 |
| Nbla10527 | AB074162 | 6370228 |
| RAB3IP | NM_001024647.2 | 1410603 |
| DLX1 | NM_178120.4 | 3420672 |
| DRD1IP | NM_015722.2 | 940746 |
| FOXD1 | NM_004472.2 | 3870500 |
| LOC728755 | XM_001128377.2 | 5670280 |
| AFF3 | NM_001025108.1 | 650753 |
| F2RL2 | NM_004101.2 | 1980730 |
| MN1 | NM_002430.2 | 6480259 |
| CBCAQH03 5 | AV737317 | 1010082 |
| LOC791120 | NR_015357.1 | 4920706 |
| SIX1 | NM_005982.2 | 1450408 |
| OXTR | NM_000916.3 | 7050768 |
| WSB1 | NM_134264.2 | 7400372 |

COMPOSITIONS AND METHODS FOR INDUCED TISSUE REGENERATION IN MAMMALIAN SPECIES

This application is a divisional of U.S. application Ser. No. 14/896,664, filed on Dec. 7, 2015, which is a 371 of PCT Application No. PCT/US14/40601, filed Jun. 3, 2014, and claims the benefit of U.S. Provisional Application No. 61/831,421 filed on Jun. 5, 2013. The entire contents of the foregoing applications are expressly incorporated herein by reference in their entirety.

FIELD OF THE INVENTION

The field of the invention relates to the field of tissue regeneration and to the reprogramming of somatic cells such that they obtain the capacity to regenerate tissue.

BACKGROUND OF THE INVENTION

Advances in stem cell technology, such as the isolation and propagation in vitro of primordial stem (PS) cells, including embryonic stem cells ("ES" cells including human ES cells ("hES" cells)) and related primordial stem cells including but not limited to, iPS, EG, EC, ICM, epiblast, or ED cells (including human iPS, EG, EC, ICM, epiblast, or ED cells), constitute an important new area of medical research. PS cells have a demonstrated potential to be propagated in the undifferentiated state and then to be induced subsequently to differentiate into any and all of the cell types in the human body, including complex tissues. Many of these PS cells are naturally telomerase positive in the undifferentiated state, thereby allowing the cells to be expanded extensively and subsequently genetically modified and clonally expanded. The telomere length of many of these cells is comparable to that observed in sperm DNA (approximately 10-18 kb TRF length). Differentiated cells derived from these immortal lines begin to show repression of the expression of the catalytic component of telomerase (TERT) as they differentiate, but nonetheless still display a long initial telomere length providing the cells with a long replicative capacity compared to fetal or adult-derived tissue. This has led, for example, to the prediction that many diseases resulting from the dysfunction of cells may be amenable to treatment by the administration of hES-derived cells of various differentiated types (Thomson et al., *Science* 282:1145-1147 (1998)).

Nuclear transfer studies have demonstrated that it is possible to transform a somatic differentiated cell back to a PS cell-like state such as that of embryonic stem ("ES") cells (Cibelli et al., *Nature Biotech* 16:642-646 (1998)) or embryo-derived ("ED") cells. The development of technologies to reprogram somatic cells back to a totipotent ES cell-like state, such as by the transfer of the genome of the somatic cell to an enucleated oocyte and the subsequent culture of the reconstructed embryo to yield ES-like cells, often referred to as somatic cell nuclear transfer ("SCNT") or through analytical reprogramming technology wherein somatic cells are reprogrammed using transcriptional regulators (see PCT application Ser. No. PCT/US2006/030632 filed on Aug. 3, 2006 and titled "Improved Methods of Reprogramming Animal Somatic Cells", incorporated herein by reference) has been described. These methods offer potential methods to transplant primordial-derived somatic cells with a nuclear genotype of the patient (Lanza et al., *Nature Medicine* 5:975-977 (1999)). Potentially this technology could address the issue of transplant rejection.

In addition to SCNT and analytical reprogramming technologies, other techniques exist to address the problem of transplant rejection, including the use of gynogenesis and androgenesis (see U.S. application No. 60/161,987, filed Oct. 28, 1999; Ser. No. 09/697,297, filed Oct. 27, 2000; Ser. No. 09/995,659, filed Nov. 29, 2001; Ser. No. 10/374,512, filed Feb. 27, 2003; PCT application no. PCT/US00/29551, filed Oct. 27, 2000; the disclosures of which are incorporated by reference in their entirety). In the case of a type of gynogenesis designated parthenogenesis, pluripotent stem cells may be manufactured without antigens foreign to the gamete donor and therefore useful in manufacturing cells that can be transplanted without rejection. In addition, parthenogenic stem cell lines can be assembled into a bank of cell lines homozygous in the HLA region (or corresponding MHC region of nonhuman animals) to reduce the complexity of a stem cell bank in regard to HLA haplotypes.

In addition, cell lines or a bank of said cell lines can be produced that are hemizygous in the HLA region (or corresponding MHC region of nonhuman animals; see PCT application Ser. No. PCT/US2006/040985 filed Oct. 20, 2006 entitled "Totipotent, Nearly Totipotent or Pluripotent Mammalian Cells Homozygous or Hemizygous for One or More Histocompatibility Antigen Genes", incorporated herein by reference). A bank of hemizygous cell lines provides the advantage of not only reducing the complexity inherent in the normal mammalian MHC gene pool, but it also reduces the gene dosage of the antigens to reduce the expression of said antigens without eliminating their expression entirely, thereby not stimulating a natural killer response.

In regard to differentiating PS cells into desired cell types, the potential to clonally isolate lines of human embryonic progenitor cell lines provides a means to propagate novel highly purified cell lineages with a prenatal pattern of gene expression useful for regenerating tissues such as skin in a scarless manner. Such cell types have important applications in research, and for the manufacture of cell-based therapies (see PCT application Ser. No. PCT/US2006/013519 filed on Apr. 11, 2006 and titled "Novel Uses of Cells With Prenatal Patterns of Gene Expression"; U.S. patent application Ser. No. 11/604,047 filed on Nov. 21, 2006 and titled "Methods to Accelerate the Isolation of Novel Cell Strains from Pluripotent Stein Cells and Cells Obtained Thereby"; and U.S. patent application Ser. No. 12/504,630 filed on Jul. 16, 2009 and titled "Methods to Accelerate the Isolation of Novel Cell Strains from Pluripotent Stem Cells and Cells Obtained Thereby", each incorporated herein by reference). Nevertheless, there remains a need for improved methods to regenerate tissues in mammals wherein the administration of exogenous cells is not effective.

In contrast to mammalian species, some animal species show a profound innate capability for tissue regeneration (TR). In the case of metazoans such as planaria, sea stars, and some amphibian species such as axolotls, a profound regenerative potential exists within the animals such that many injuries that do not lead to the immediate death of the organism have the potential to be repaired by regeneration of the target tissue from the remaining cells of the tissue, typically in a scarless, or relatively scarless manner, even if the tissue is composed largely of post-mitotic cells such as those of the brain or heart muscle. The molecular mechanisms that allow such regeneration to occur in some animals while not in the normal mammalian species including humans are not currently known. The identification of such molecular mechanisms would facilitate the invention of novel methods for introducing the molecular mechanisms into cells and tissue in vivo, thereby causing an "induced tissue regeneration" (iTR) which could facilitate the repair of tissues afflicted with trauma or degenerative disease, including but not limited to age-related degenerative disease, as well as facilitate research in tissue regeneration. Contemplated are mammalian animal models in which the effects of iTR are studied in the context of tissue damage and regeneration, as well as transgenic mammalian animal models using diverse genetic backgrounds, including mutant genetic backgrounds that lead to diverse disease models in the animals into which methods of iTR can be applied to study the potential of iTR as a therapeutic strategy for said disease.

SUMMARY OF THE INVENTION

In certain embodiments the invention provides methods and compositions useful for enhancing the regeneration of tissue or organs in a subject or in vitro. In other embodiments the invention provides methods and compositions for inhibiting the regeneration of tissue or organs in a subject or in vitro.

In some embodiments the invention provides a method of enhancing tissue or organ regeneration in a subject comprising administering to the subject one or more of the genes or gene products chosen from PCDHB2, PCDHB17, Nbla10527, RAB3IP, DLX1, DRD11P, FOXD1, LOC728755, AFF3, F2RL2, MN1, CBCAQH03 5, LOC791120, SFX1, OXTR, and WSB1.

In other embodiments the invention provides a method of inhibiting tissue or organ regeneration in a subject comprising administering to the subject one or more agents that inhibits expression of one or more genes chosen from PCDHB2, PCDHB17, Nbla10527, RAB3IP, DLX1, DRD1 IP, FOXD1, LOC728755, AFF3, F2RL2, MN1, CBCAQH03 5, LOC791120, SIX1, OXTR, and WSB1.

In yet other embodiments the invention provides a method of inhibiting tissue or organ regeneration in a subject comprising administering to the subject one or more genes chosen from COMT, TRIM4, CAT, PSMD, SHMT, LOC205251, ZNF280D, S100A6, MGMT, ZNF280D, DYNLT3, NAALADL1, COX7A1, TSPYL5, IAH1, C18orf56, RPS7, FDPS, ELOVL6, INSIG1, ACAT2, and MAOA.

In still other embodiments the invention provides a method of enhancing tissue or organ regeneration in a subject comprising administering to a subject one or more agents that inhibit expression of one or more genes chosen from COMT, TRIM4, CAT, PSMD, SHMT, LOC205251, ZNF280D, S100A6, MGMT, ZNF280D, DYNLT3, NAALADL1, COX7A1, TSPYL5, IAH1, C18orf56, RPS7, FDPS, ELOVL6, INSIG1, ACAT2, and MAOA.

In certain embodiments the invention provides a method of inhibiting tissue or organ regeneration in a subject comprising administering to the subject a gene or gene product encoded by COX7A1.

In other embodiments the invention provides a method of enhancing tissue or organ regeneration in a subject comprising administering to the subject one or more agents that inhibit COX7A1.

In still other embodiments the invention provides a method of inhibiting tissue or organ regeneration in a subject comprising administering to the subject a gene or gene product encoded by COX7A1 and one more or genes chosen from COMT, TRIM4, CAT, PSMD, SHMT, LOC205251, ZNF280D, S100A6, MGMT, ZNF280D, DYNLT3, NAALADL1, TSPYL5, C18orf56, RPS7, FDPS, ELOVL6, INSIG1, ACAT2, and MAOA.

In yet other embodiments the invention provides a method of enhancing tissue or organ regeneration in a subject comprising administering to the subject one or more agents that inhibit COX7A1 and one or more agents that inhibit one or more genes or gene products chosen from COMT, TRIM4, CAT, PSMD, SHMT, LOC205251, ZNF280D, S100A6, MGMT, ZNF280D, DYNLT3, NAALADL1, TSPYL5, IAH1, C18orf56, RPS7, FDPS, ELOVL6, INSIG1, ACAT2, and MAOA.

In some embodiments the invention provides a method of enhancing tissue or organ regeneration in vitro comprising contacting a cell in vitro with one or more of the genes or gene products chosen from PCDHB2, PCDHB17, Nbla10527, RAB3IP, DLX1, DRD11P, FOXD1, LOC728755, AFF3, F2RL2, MN1, CBCAQH03 5, LOC791120, SIX1, OXTR, and WSB1.

In other embodiments the invention provides a method of inhibiting issue or organ regeneration in vitro comprising contacting a cell in vitro with one or more agents that inhibits expression of one or more genes chosen from PCDHB2, PCDHB17, Nbla10527, RAB3IP, DLX1, DRD1 IP, FOXD1, LOC728755, AFF3, F2RL2, MN1, CBCAQH03 5, LOC791120, SIX1, OXTR, and WSB1.

In yet other embodiments the invention provides a method of inhibiting tissue or organ regeneration in vitro comprising contacting a cell in vitro with one or more genes chosen from COMT, TRIM4, CAT, PSMD, SHMT, LOC205251, ZNF280D, S100A6, MGMT, ZNF280D, DYNLT3, NAALADL1, COX7A1, TSPYL5, IAH1, C18orf56, RPS7, FDPS, ELOVL6, INSIG1, ACAT2, and MAOA.

In still other embodiments the invention provides a method of enhancing tissue or organ regeneration in vitro comprising contacting a cell in vitro with one or more agents that inhibit expression of one or more genes chosen from COMT, TRIM4, CAT, PSMD, SHMT, LOC205251, ZNF280D, S100A6, MGMT, ZNF280D, DYNLT3, NAALADL1, COX7A1, TSPYL5, IAH1, C18orf56, RPS7, FDPS, ELOVL6, INSIG1, ACAT2, and MAOA.

In certain embodiments the invention provides a method of inhibiting tissue or organ regeneration in vitro comprising contacting a cell in vitro with a gene or gene product encoded by COX7A1.

In other embodiments the invention provides a method of enhancing tissue or organ regeneration in vitro comprising contacting a cell in vitro with one or more agents that inhibit COX7A1.

In still other embodiments the invention provides a method of inhibiting tissue or organ regeneration in vitro comprising contacting a cell in vitro with a gene or gene product encoded by COX7A1 and one more or genes chosen from COMT, TRIM4, CAT, PSMD, SHMT, LOC205251, ZNF280D, S100A6, MGMT, ZNF280D, DYNLT3, NAALADL1, TSPYL5, IAH1, C18orf56, RPS7, FDPS, ELOVL6, INSIG1, ACAT2, and MAOA.

In yet other embodiments the invention provides a method of enhancing tissue or organ regeneration in vitro comprising contacting a cell in vitro with one or more agents that inhibit COX7A1 and one or more agents that inhibit one or more genes or gene products chosen from COMT, TRIM4, CAT, PSMD, SHMT, LOC205251, ZNF280D, S100A6, MGMT, ZNF280D, DYNLT3, NAALADL1, TSPYL5, IAH1, C18orf56, RPS7, FDPS, ELOVL6, INSIG1, ACAT2, and MAOA. In some embodiments the invention provides a method of regenerating skin in a subject comprising administering an inhibitor of COX7A1 to a subject.

In further embodiments the invention provides a method of generating skin in a subject comprising administering a siRNA molecule that inhibits COX7A1 to the subject.

In yet further embodiments the invention provides a method of enhancing the generation skin in vitro comprising administering to a cell, such as an epithelial, cell a siRNA molecule that inhibits COX7A1 to the subject.

In other embodiments the invention provides a method of enhancing expression in a cell of one or more genes expressed in embryonic cells comprising contacting the cell with one or more agents that inhibit COX7A1.

In still other embodiments the invention provides a method of enhancing expression in a cell of one or more genes expressed in embryonic cells comprising contacting the cell with a siRNA that inhibits COX7A1.

In certain embodiments the invention provides a method of enhancing KRT17 expression in a cell comprising contacting the cell with one or more agents that inhibit COX7A1.

In further embodiments the invention provides a method of enhancing KRT17 expression in a cell comprising contacting the cell with a siRNA that inhibits COX7A1.

In certain embodiments the invention provides a method of inhibiting ACAT2 and COL1A1 expression in a cell comprising contacting the cell with one or more agents that inhibit COX7A1.

In further embodiments the invention provides a method of inhibiting ACAT2 and COL1A1 expression in a cell comprising contacting the cell with a siRNA that inhibits COX7A1.

In further embodiments the invention provides a method of treating cancer comprising administering to a subject the gene or gene product of COX7A1.

In some embodiments the invention provides a method of enhancing wound healing in a subject comprising administering to the subject one or more of the genes or gene products chosen from PCDHB2, PCDHB17, Nbla10527, RAB3IP, DLX1, DRD11P, FOXD1, LOC728755, AFF3, F2RL2, MN1, CBCAQH03 5, LOC791120, SIX1, OXTR, and WSB1.

In other embodiments the invention provides a method of inhibiting wound healing in a subject comprising administering to the subject one or more agents that inhibits expression of one or more genes chosen from PCDHB2, PCDHB17, Nbla10527, RAB3IP, DLX1, DRD11P, FOXD1, LOC728755, AFF3, F2RL2, MN1, CBCAQH03 5, LOC791120, SIX1, OXTR, and WSB1.

In yet other embodiments the invention provides a method of inhibiting wound healing in a subject comprising administering to the subject one or more genes chosen from COMT, TRIM4, CAT, PSMD, SHMT, LOC205251, ZNF280D, S100A6, MGMT, ZNF280D, DYNLT3, NAALADL1, COX7A1, TSPYL5, IAH1, C18orf56, RPS7, FDPS, ELOVL6, ACAT2, and MAOA.

In still other embodiments the invention provides a method of wound healing in a subject comprising administering to a subject one or more agents that inhibit expression of one or more genes chosen from COMT, TRIM4, CAT, PSMD, SHMT, LOC205251, ZNF280D, S100A6, MGMT, ZNF280D, DYNLT3, NAALADL1, COX7A1, TSPYL5, IAH1, C18orf56, RPS7, FDPS, ELOVL6, ENSIG1, ACAT2, and MAOA.

In certain embodiments the invention provides a method of inhibiting wound healing in a subject comprising administering to the subject a gene or gene product encoded by COX7A1.

In other embodiments the invention provides a method of enhancing wound healing in a subject comprising administering to the subject one or more agents that inhibit COX7A1.

In still other embodiments the invention provides a method of inhibiting wound healing in a subject comprising administering to the subject a gene or gene product encoded by COX7A1 and one more or genes chosen from COMT, TRIM4, CAT, PSMD, SHMT, LOC205251, ZNF280D, S100A6, MGMT, ZNF280D, DYNLT3, NAALADL1, TSPYL5, IAH1, C18orf56, RPS7, FDPS, ELOVL6, ENSIG1, ACAT2, and MAOA.

In yet other embodiments the invention provides a method of enhancing wound healing in a subject comprising administering to the subject one or more agents that inhibit COX7A1 and one or more agents that inhibit one or more genes or gene products chosen from COMT, TRIM4, CAT, PSMD, SHMT, LOC205251, ZNF280D, S100A6, MGMT, ZNF280D, DYNLT3, NAALADL1, TSPYL5, IAH1, C18orf56, RPS7, FDPS, ELOVL6, INSIG1, ACAT2, and MAOA.

In certain embodiments the invention provides a pharmaceutical composition comprising one or more genes or gene products encoded by genes disclosed in FIG. 1 and a suitable carrier.

In other embodiments the invention provides a pharmaceutical composition comprising a plurality of genes or gene products encoded by genes disclosed in FIG. 1 and a suitable carrier.

In further embodiments the invention provides a transgenic animal expressing one or more heterologous or xenogeneic genes chosen from PCDHB2, PCDHB17, Nbla10527, RAB3IP, DLX1, DRD11P, FOXD1, LOC728755, AFF3, F2RL2, MN1, CBCAQH03 5, LOC791120, SIX1, OXTR, WSB1, COMT, TRIM4, CAT, PSMD, SHMT, LOC205251, ZNF280D, S100A6, MGMT, ZNF280D, DYNLT3, NAALADL1, COX7A1, TSPYL5, IAH1, C18orf56, RPS7, FDPS, ELOVL6, INSIG1, ACAT2, and MAOA.

In still other embodiments the invention provides a kit comprising one or more genes or gene products expressed by the genes chosen from COMT, TRIM4, CAT, PSMD, SHMT, LOC205251, ZNF280D, S100A6, MGMT, ZNF280D, DYNLT3, NAALADL1, COX7A1, TSPYL5, IAH1, C18orf56, RPS7, FDPS, ELOVL6, INSIG1, ACAT2, and MAOA and at least one container.

In yet other embodiments the invention provides a kit comprising one or more genes or gene products expressed by the genes chosen from PCDHB2, PCDHB17, Nbla10527, RAB3IP, DLX1, DRD11P, FOXD1, LOC728755, AFF3, F2RL2, MN1, CBCAQH03 5, LOC791120, SIX1, OXTR, and WSB1 and at least one container.

BRIEF DESCRIPTION OF THE DRAWINGS

FIG. 1 TR inhibitory and TR activating genes identified by differential expression in hES-derived clonal embryonic progenitor cells compared to fetal and adult-derived somatic cells. (A) TR inhibitory genes expressed in fetal or adult-derived somatic cell types but expressed at lower levels or not expressed in clonal embryonic progenitor cells. (B) TR activating genes expressed in clonal embryonic progenitor cells but expressed at lower levels or not expressed in fetal or adult-derived somatic cell types.

Figure 2:
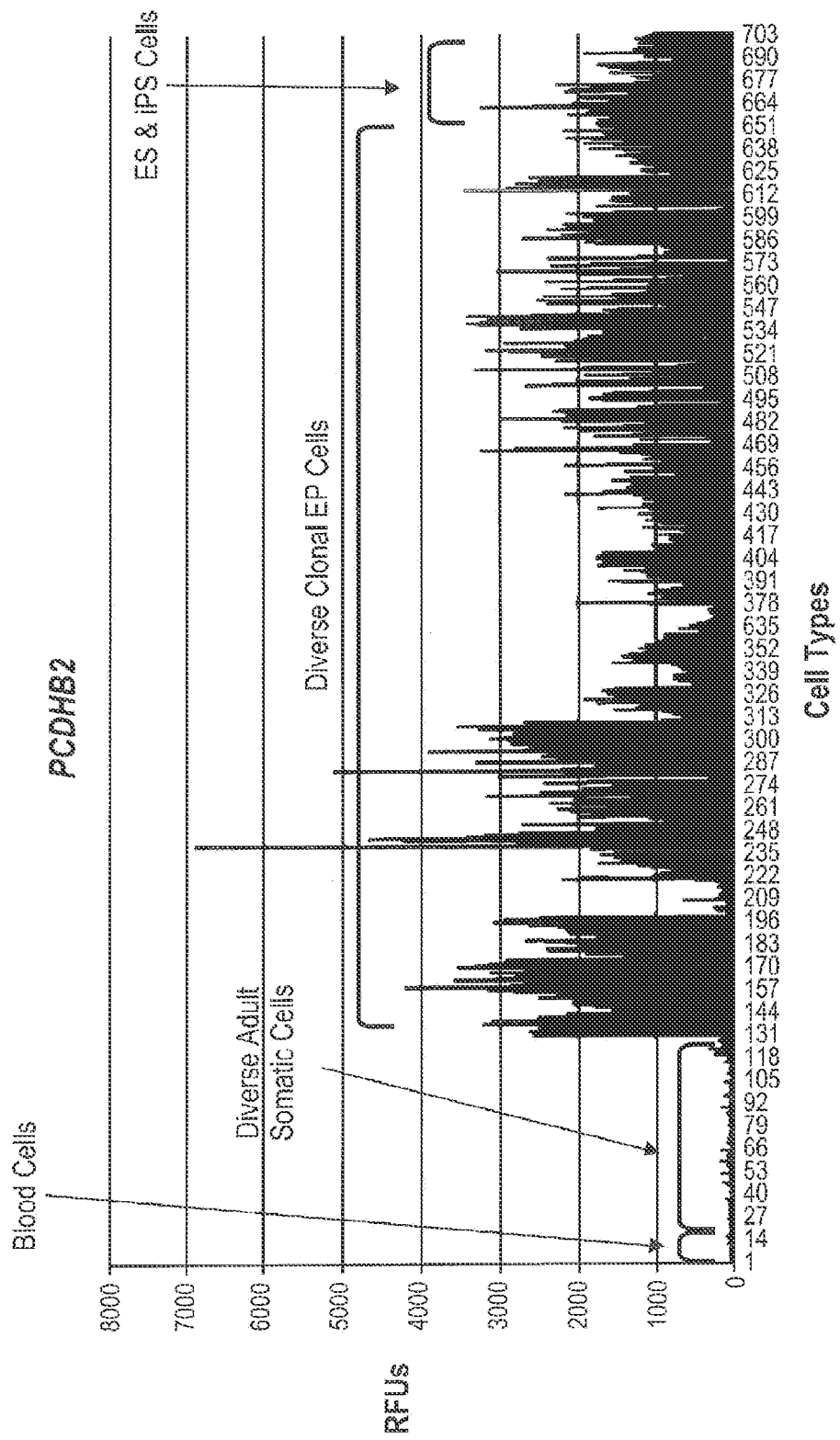
FIG. 2. RFU values for the gene PCDHB2 as determined by Illumina gene expression microarray analysis in diverse adult and embryonic cell types. From left to right are 14 diverse blood cell types, 115 diverse somatic cell types from all three germ layers, 545 diverse clonal embryonic progenitor (EP) cell lines, 12 hES cell lines and 17 human iPS cell lines.
Figure 3:
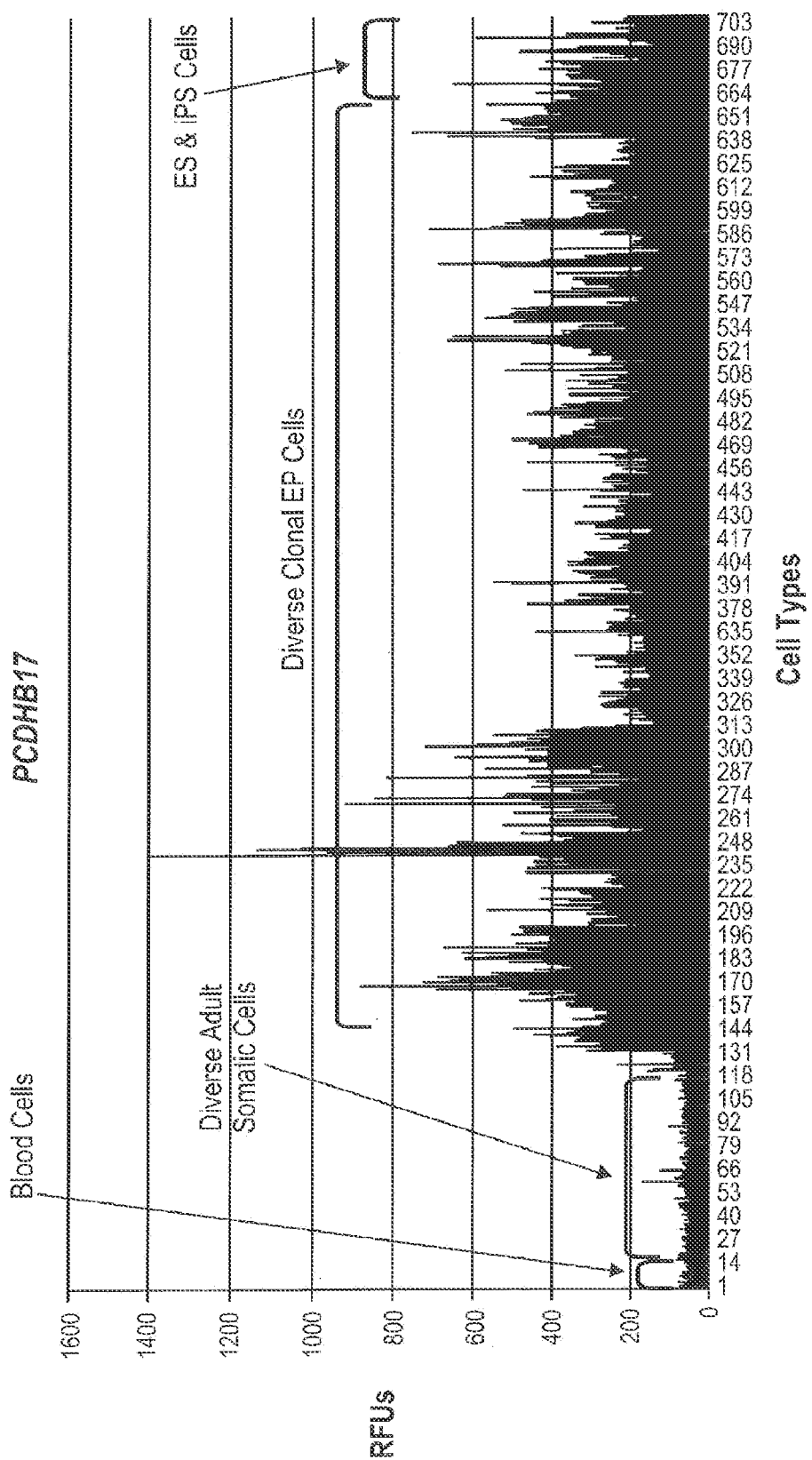

FIG. 3. RFU values for the gene PCDHB17 as determined by Illumina gene expression microarray analysis in diverse adult and embryonic cell types. From left to right are 14 diverse blood cell types, 115 diverse somatic cell types from all three germ layers, 545 diverse clonal EP cell lines, 12 hES cell lines and 17 human iPS cell lines.

Figure 4:
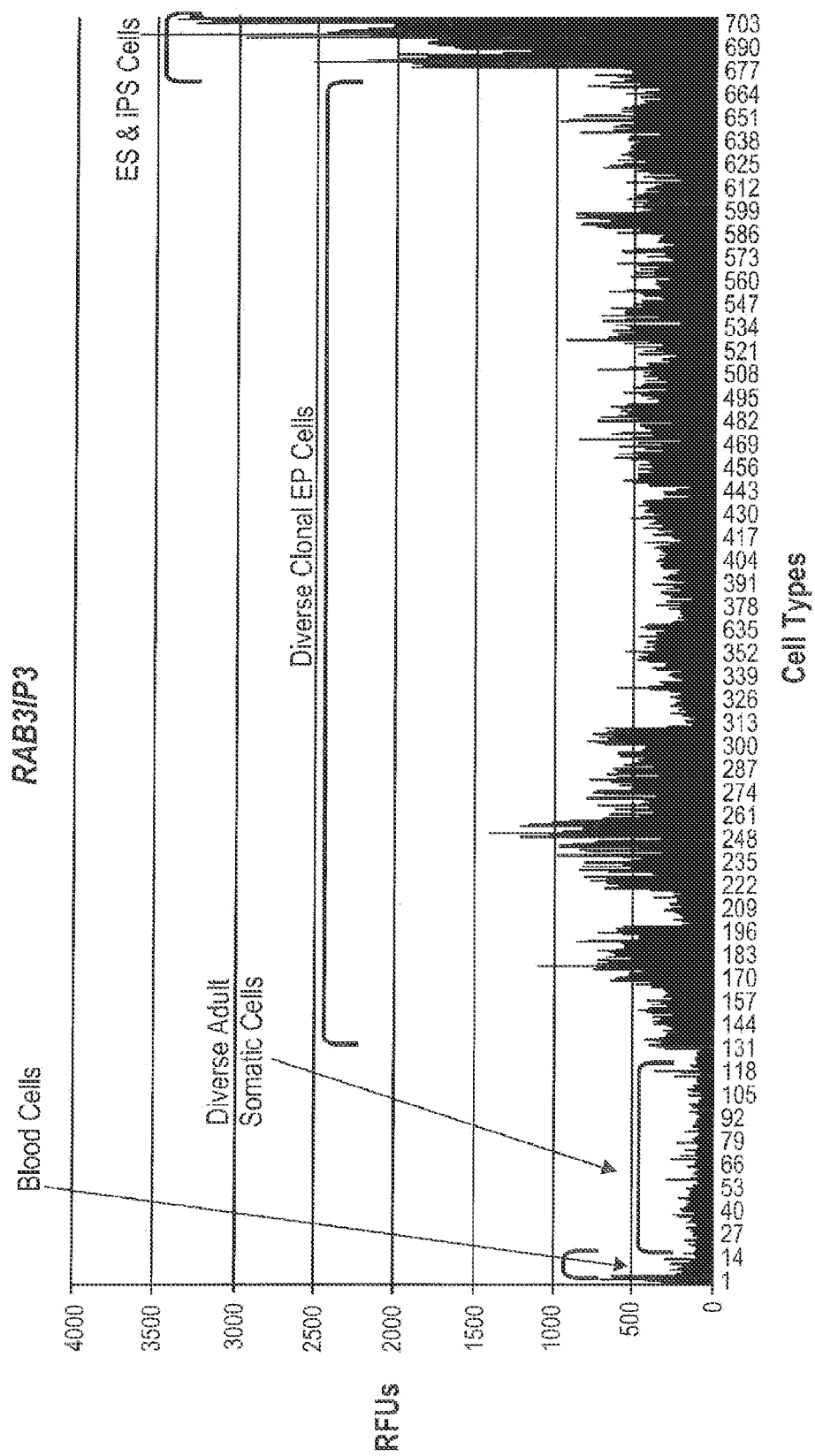

FIG. 4. RFU values for the gene RAB3IP as determined by Illumina gene expression microarray analysis in diverse adult and embryonic cell types. From left to right are 14 diverse blood cell types, 115 diverse somatic cell types from all three germ layers, 545 diverse clonal EP cell lines, 12 hES cell lines and 17 human iPS cell lines.

Figure 5:
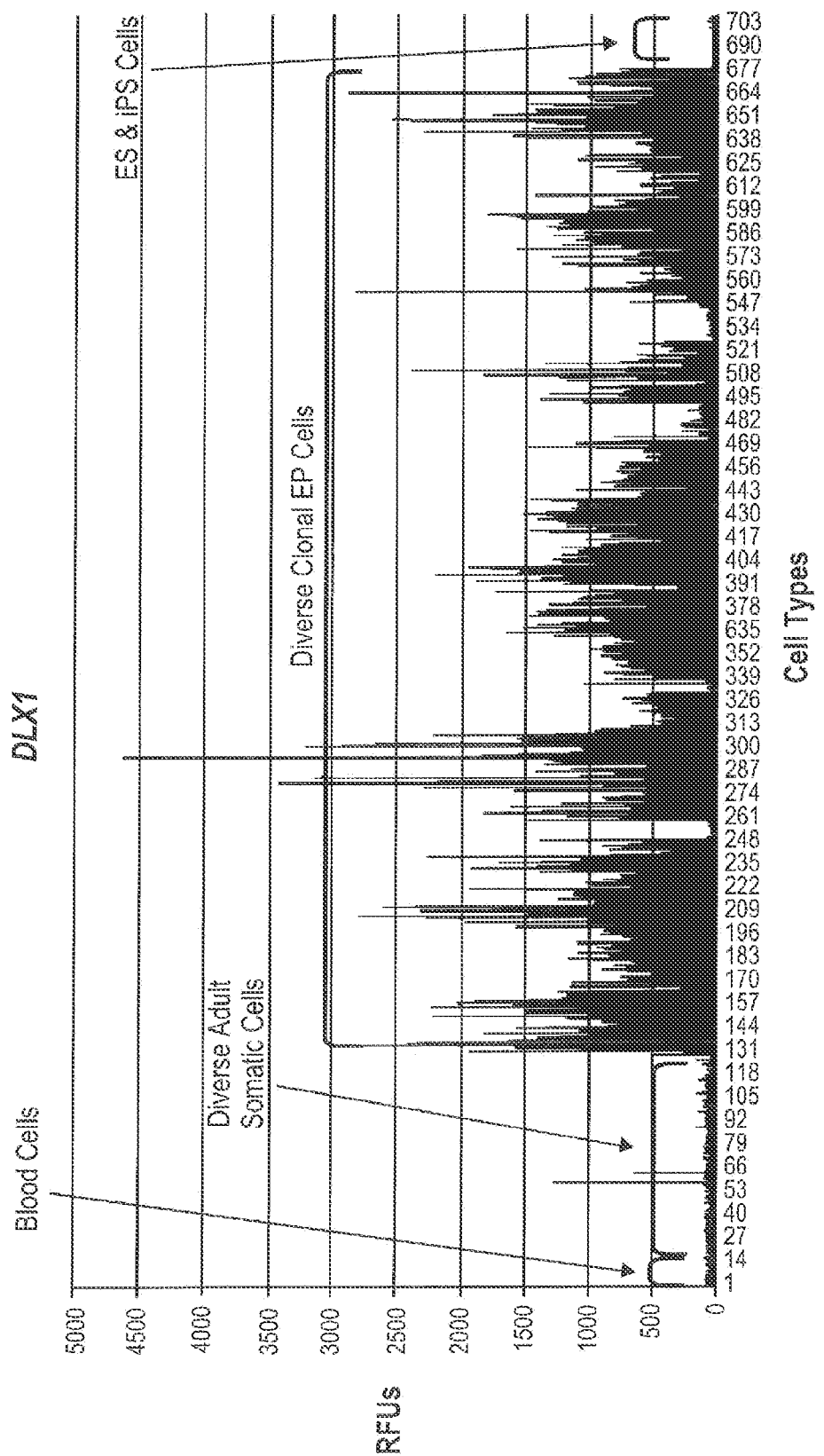

FIG. 5. RFU values for the gene DLX1 as determined by Illumina gene expression microarray analysis in diverse adult and embryonic cell types. From left to right are 14 diverse blood cell types, 115 diverse somatic cell types from all three germ layers, 545 diverse clonal EP cell lines, 12 hES cell lines and 17 human iPS cell lines.

Figure 6:
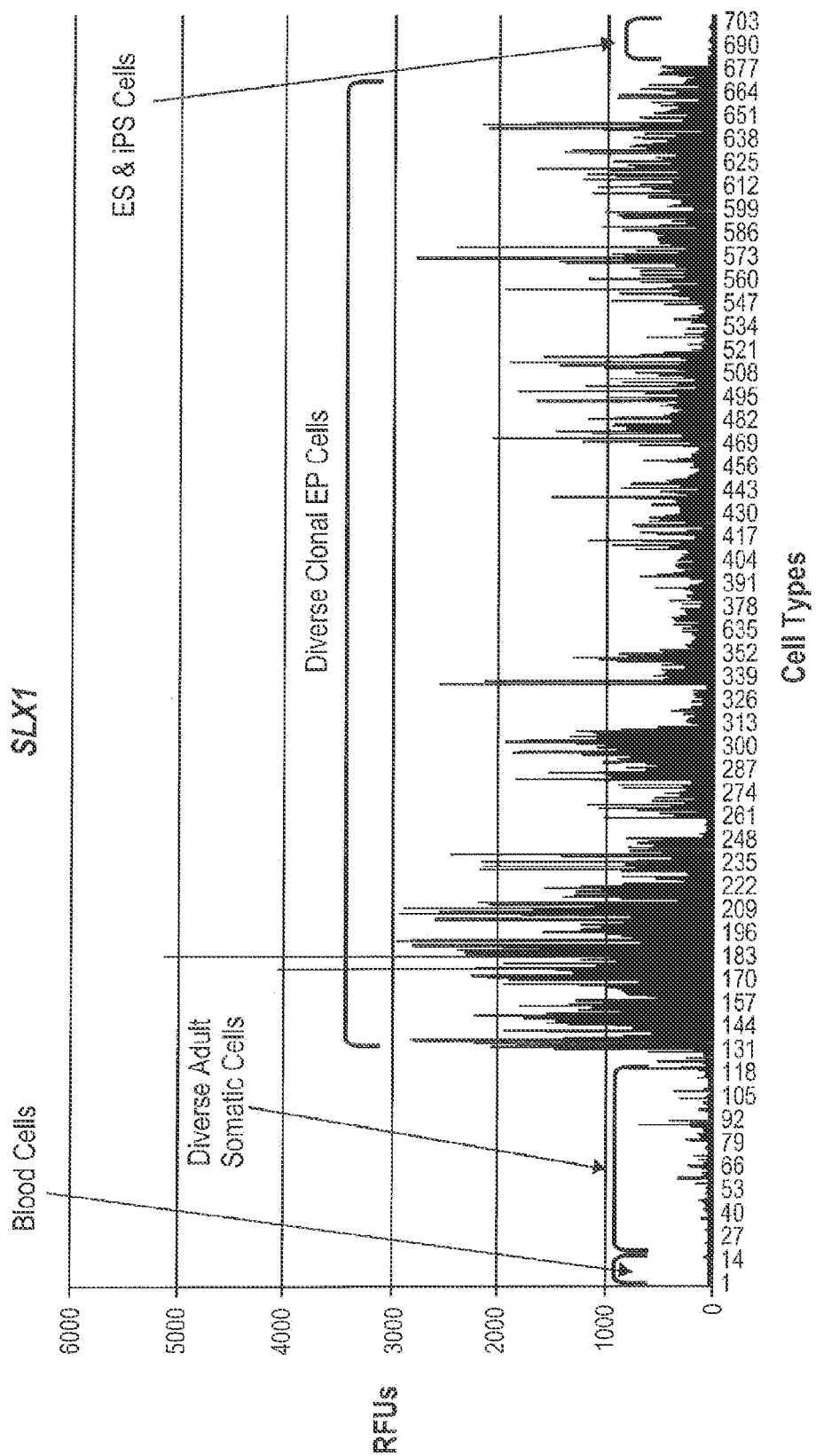

FIG. 6. RFU values for the gene SIX1 as determined by Illumina gene expression microarray analysis in diverse adult and embryonic cell types. From left to right are 14 diverse blood cell types, 115 diverse somatic cell types from all three germ layers, 545 diverse clonal EP cell lines, 12 hES cell lines and 17 human iPS cell lines.

Figure 7:
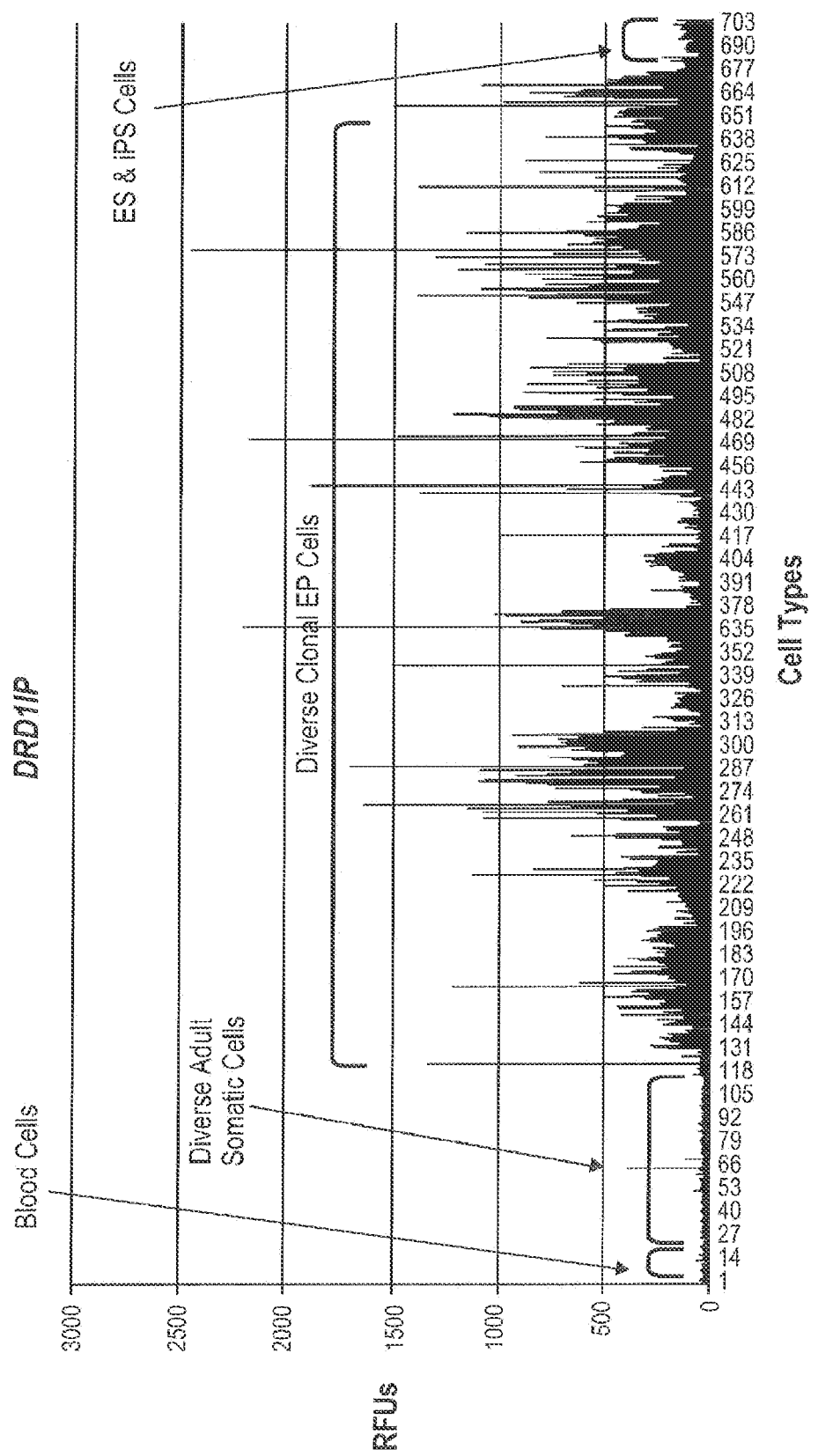

FIG. 7. RFU values for the gene DRDIIP as determined by Illumina gene expression microarray analysis in diverse adult and embryonic cell types. From left to right are 14 diverse blood cell types, 115 diverse somatic cell types from all three germ layers, 545 diverse clonal EP cell lines, 12 hES cell lines and 17 human iPS cell lines.

Figure 8:
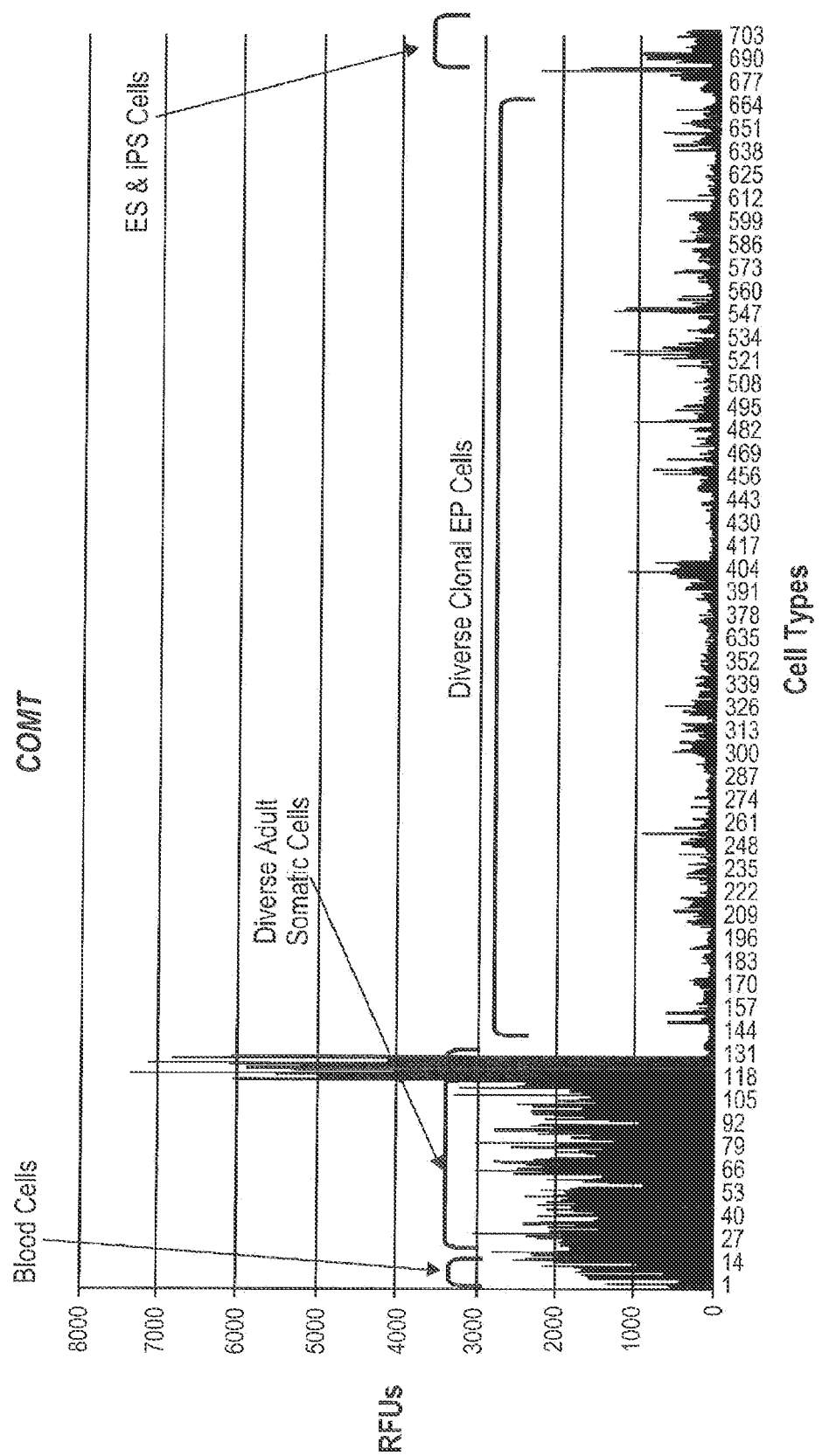

FIG. 8. RFU values for the gene COMT as determined by Illumina gene expression microarray analysis in diverse adult and embryonic cell types. From left to right are 14 diverse blood cell types, 115 diverse somatic cell types from all three germ layers, 545 diverse clonal EP cell lines, 12 hES cell lines and 17 human iPS cell lines.

Figure 9:
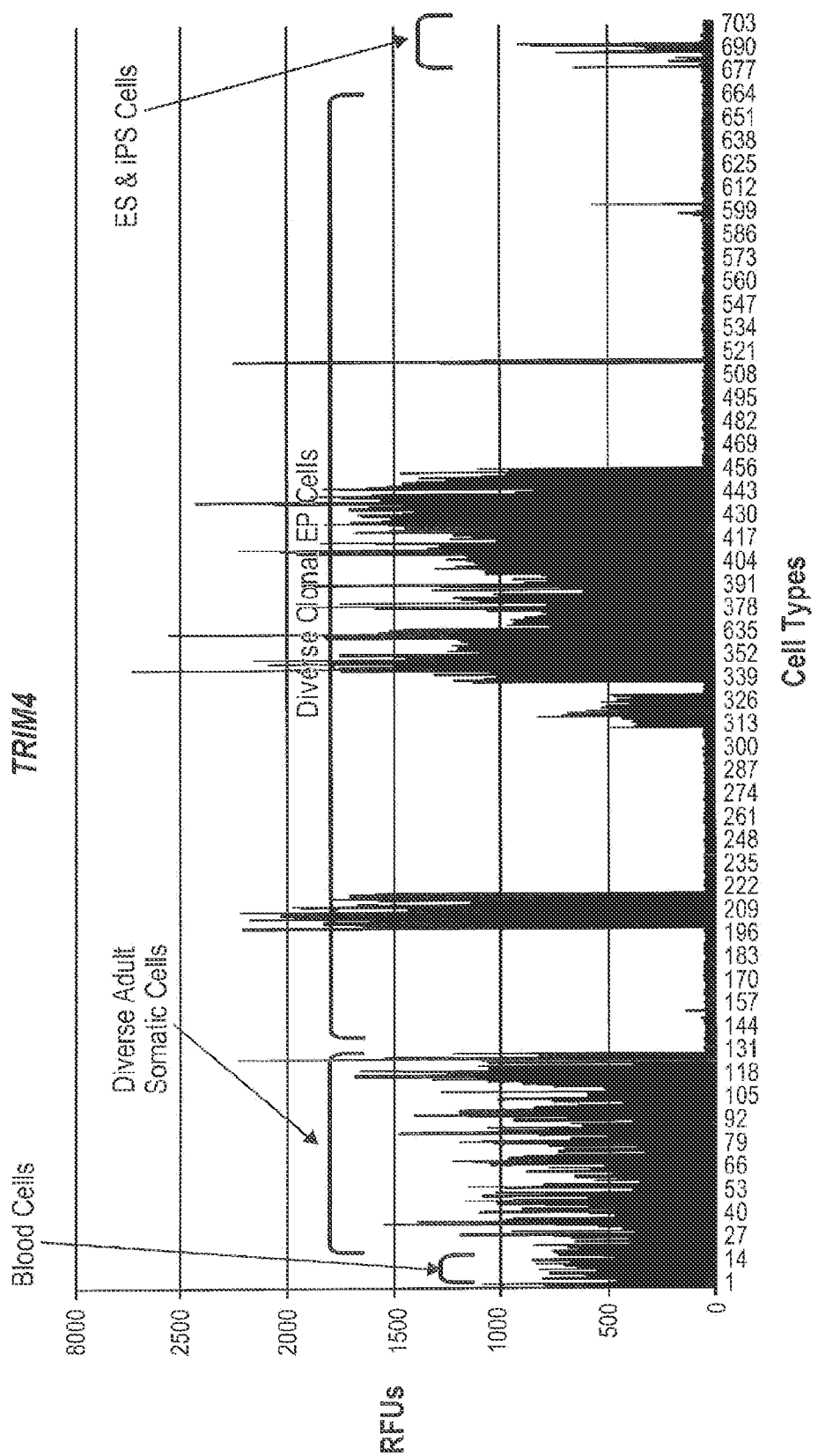

FIG. 9. RFU values for the gene TRIM4 as determined by Illumina gene expression microarray analysis in diverse adult and embryonic cell types. From left to right are 14 diverse blood cell types, 115 diverse somatic cell types from all three germ layers, 545 diverse clonal EP cell lines, 12 hES cell lines and 17 human iPS cell lines.

Figure 10:
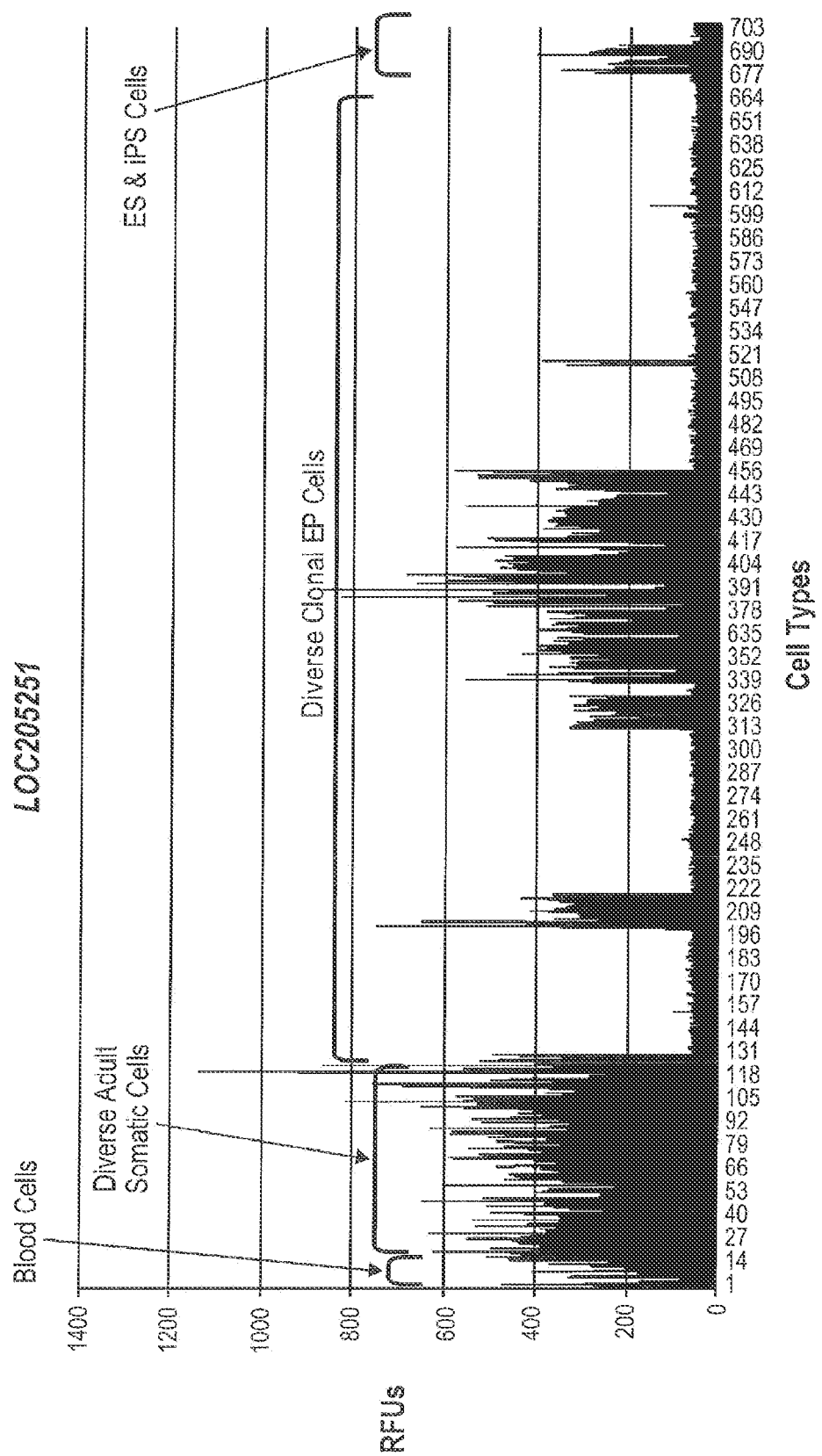

FIG. 10. RFU values for the gene LOC205251 as determined by Illumina gene expression microarray analysis in diverse adult and embryonic cell types. From left to right are 14 diverse blood cell types, 115 diverse somatic cell types from all three germ layers, 545 diverse clonal EP cell lines, 12 hES cell lines and 17 human iPS cell lines.

Figure 11:
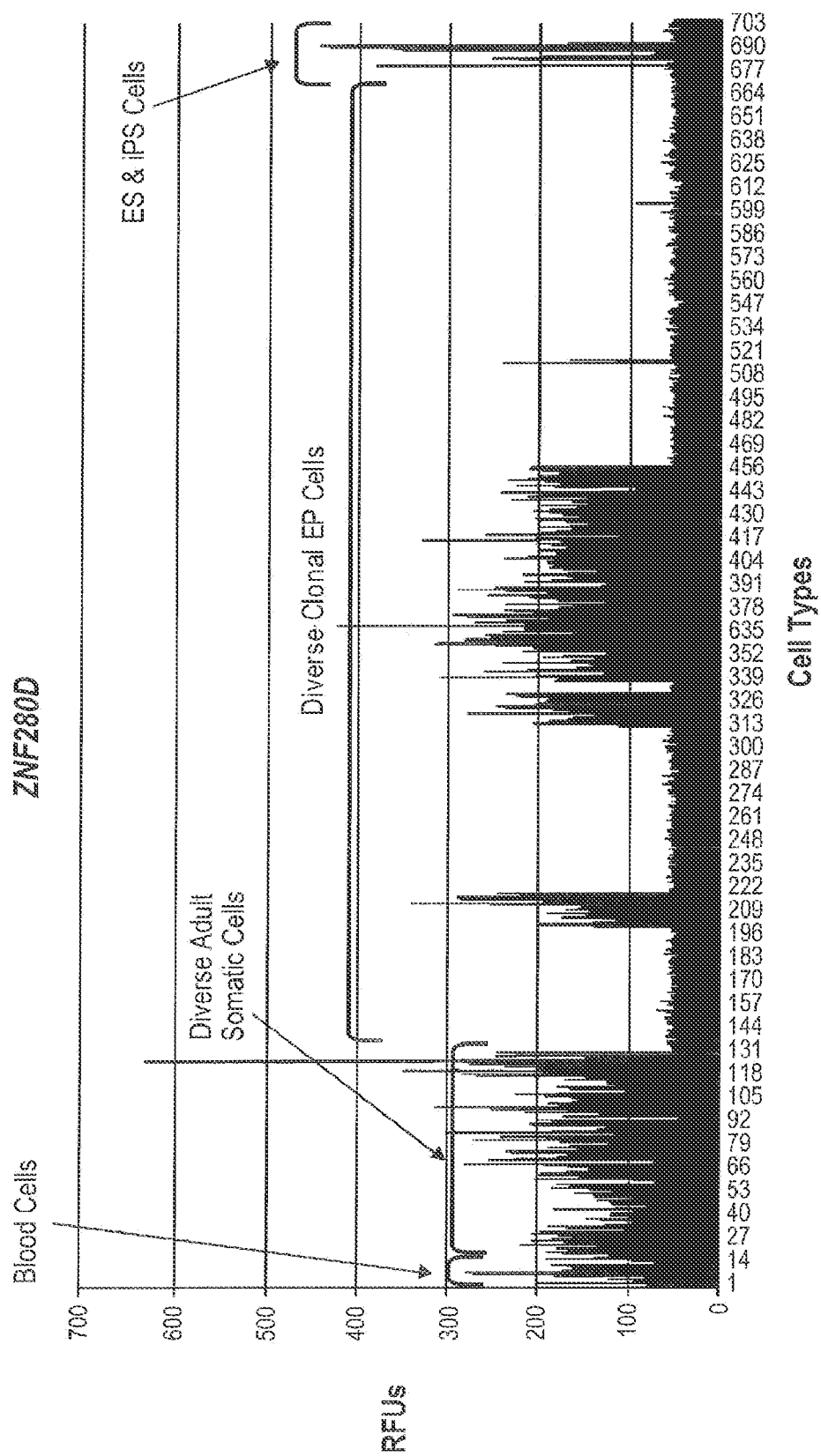

FIG. 11. RFU values for the gene ZNF280D as determined by Illumina gene expression microarray analysis in diverse adult and embryonic cell types. From left to right are 14 diverse blood cell types, 115 diverse somatic cell types from all three germ layers, 545 diverse clonal EP cell lines, 12 hES cell lines and 17 human iPS cell lines.

Figure 12:
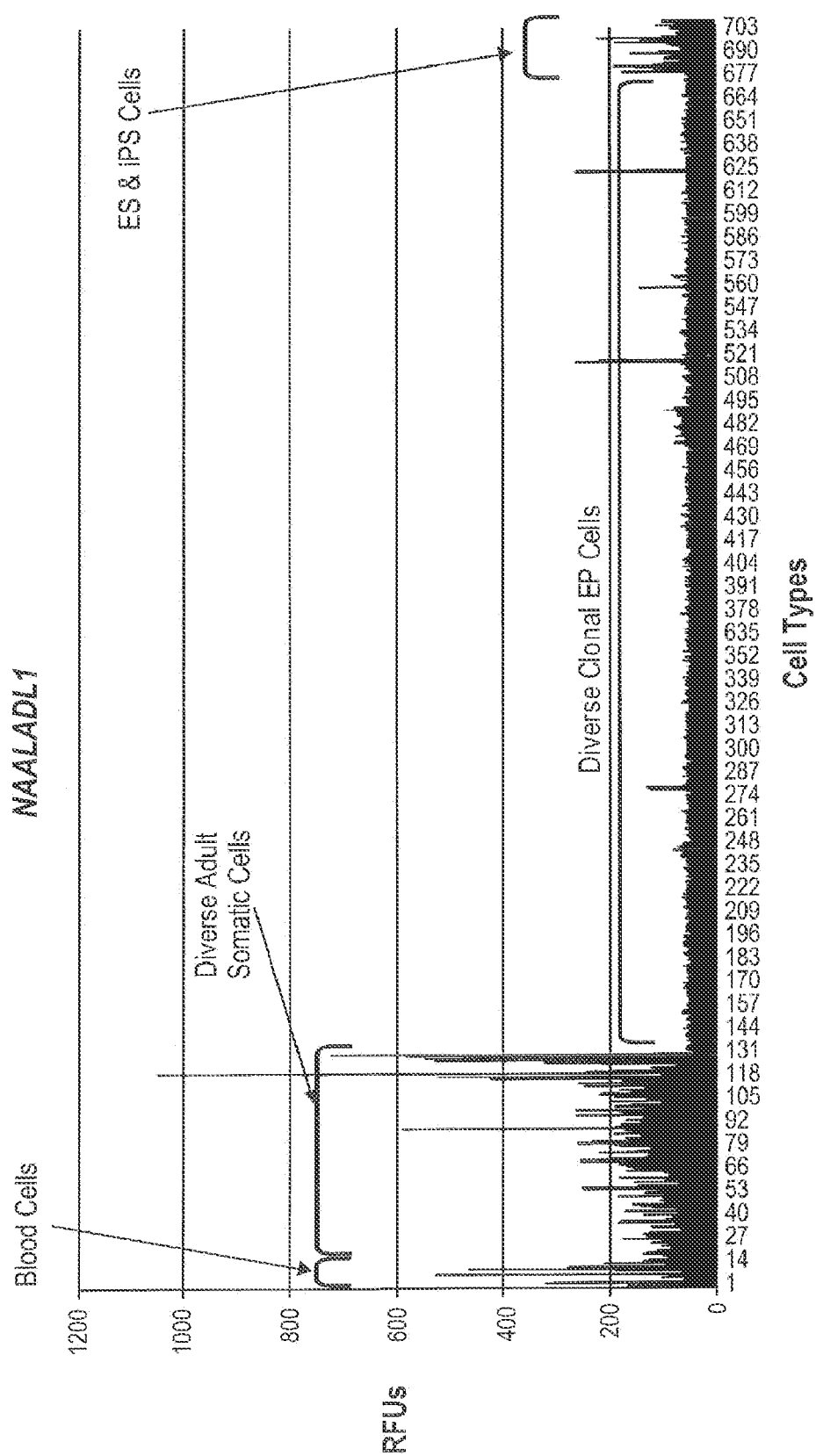

FIG. 12. RFU values for the gene NAALADL1 as determined by Illumina gene expression microarray analysis in diverse adult and embryonic cell types. From left to right are 14 diverse blood cell types, 115 diverse somatic cell types from all three germ layers, 545 diverse clonal EP cell lines, 12 hES cell lines and 17 human iPS cell lines.

Figure 13:
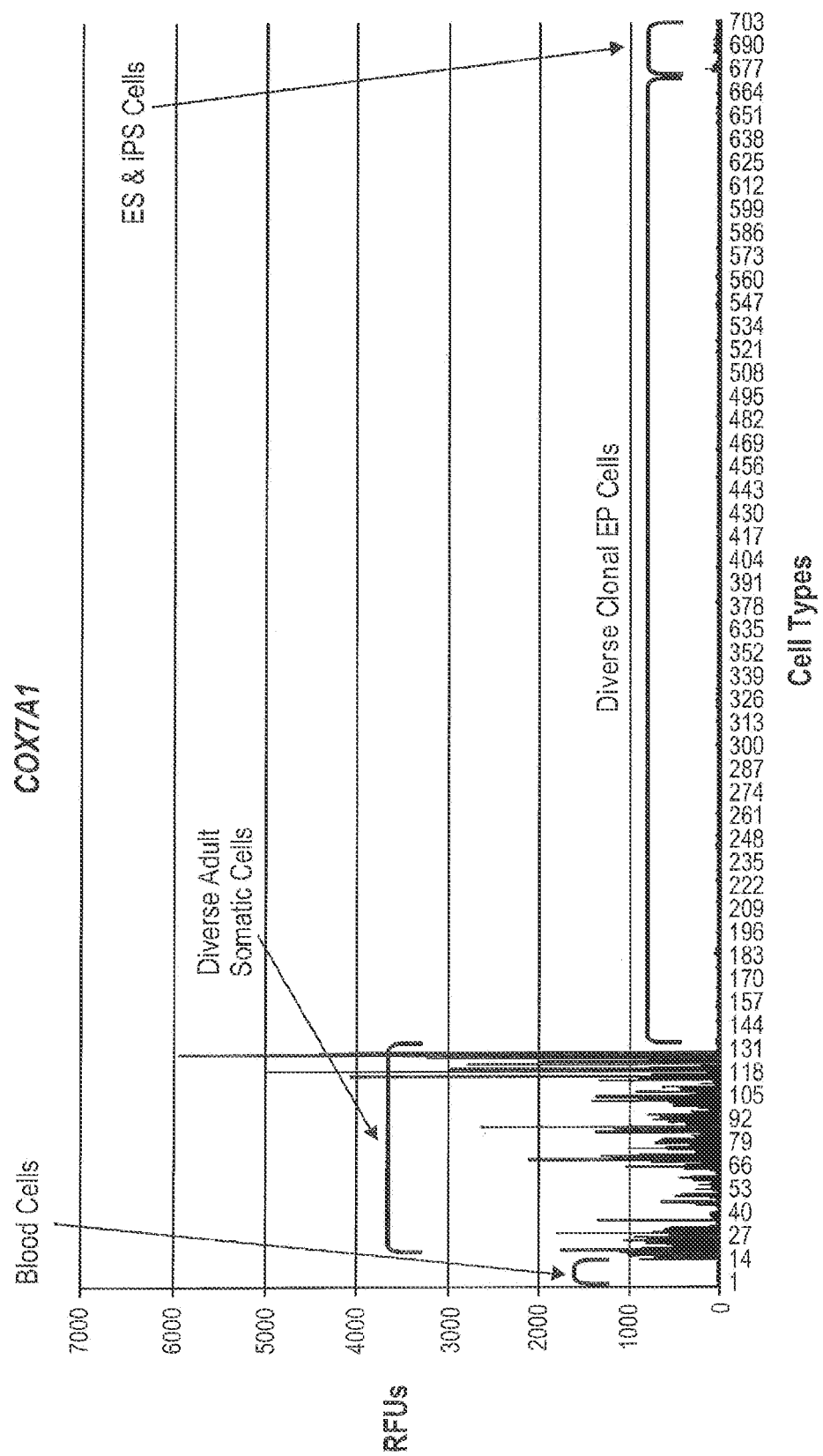

FIG. 13. RFU values for the gene COX7A1 as determined by Illumina gene expression microarray analysis in diverse adult and embryonic cell types. From left to right are 14 diverse blood cell types, 115 diverse somatic cell types from all three germ layers, 545 diverse clonal EP cell lines, 12 hES cell lines and 17 human iPS cell lines.

Figure 14:
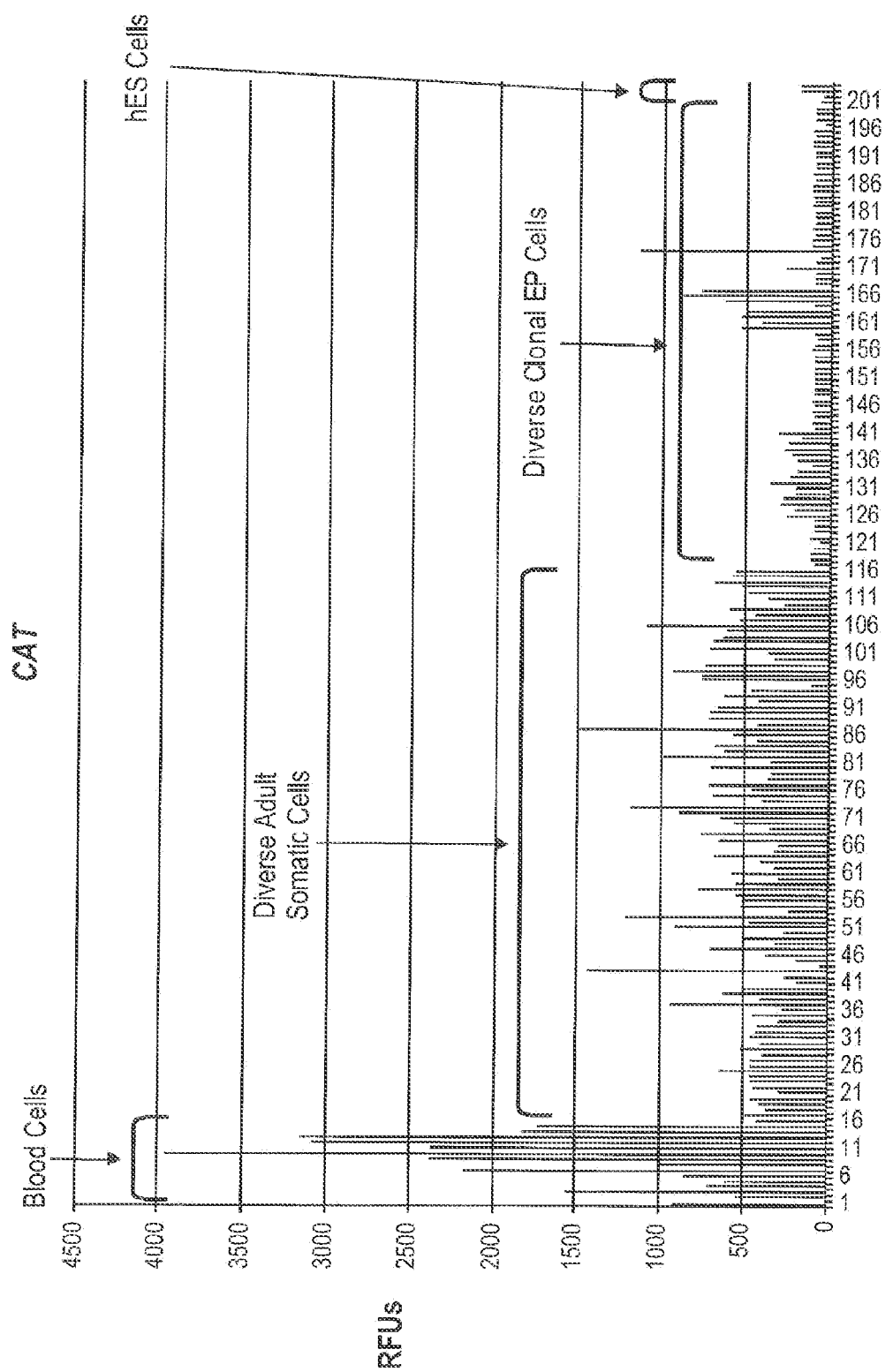

FIG. 14. RFU values for the gene CAT as determined by Illumina gene expression microarray analysis in diverse adult and embryonic cell types. From left to right are 14 diverse blood cell types, 101 diverse somatic cell types from all three germ layers, 84 diverse clonal EP cell lines, and 4 human ES cell lines.

Figure 15:
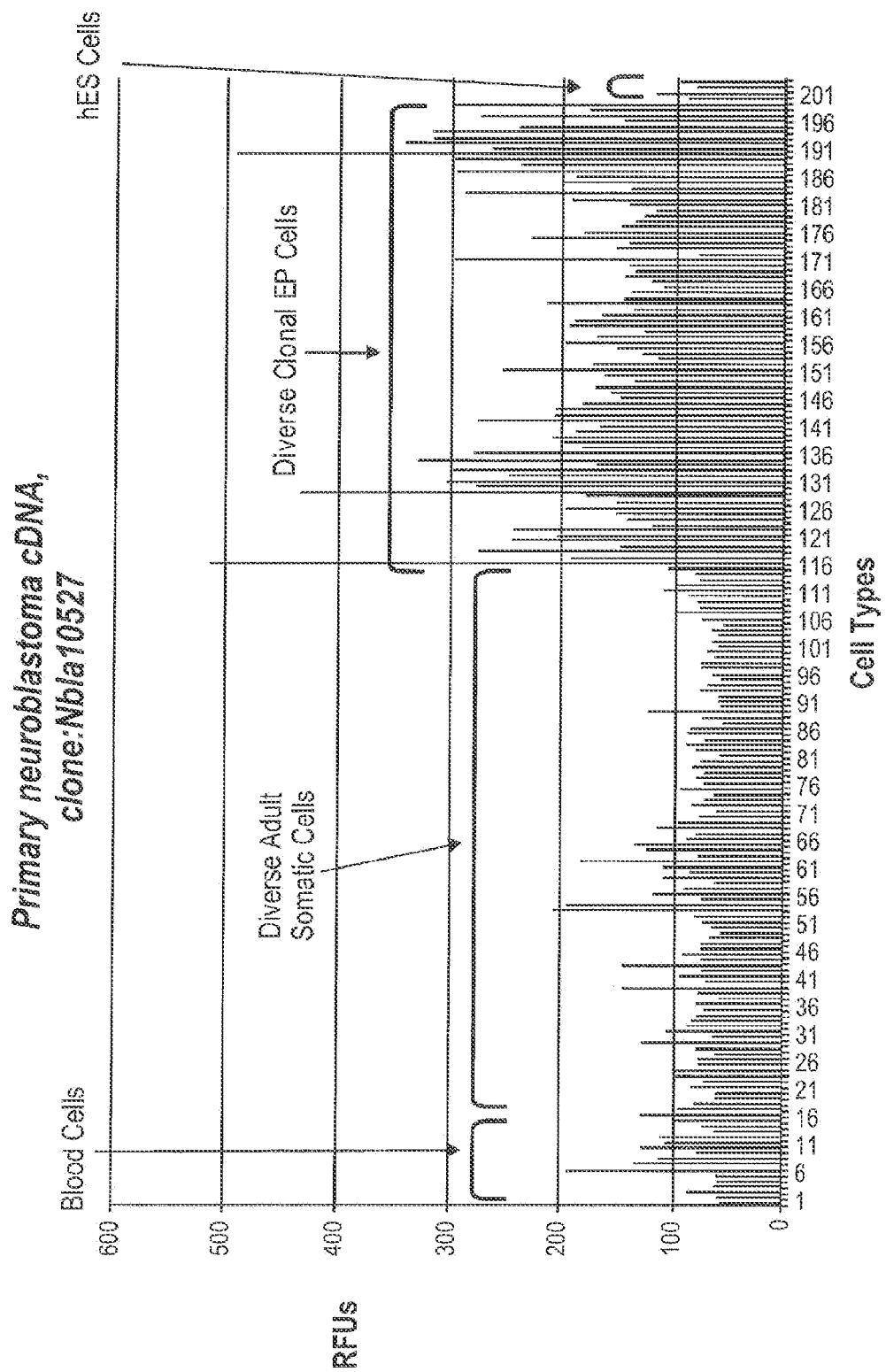

FIG. 15. RFU values for the gene primary neuroblastoma cDNA, clone:Nbla10527 as determined by Illumina gene expression microarray analysis in diverse adult and embryonic cell types. From left to right are 14 diverse blood cell types, 101 diverse somatic cell types from all three germ layers, 84 diverse clonal EP cell lines, and 4 human ES cell lines.

Figure 16:
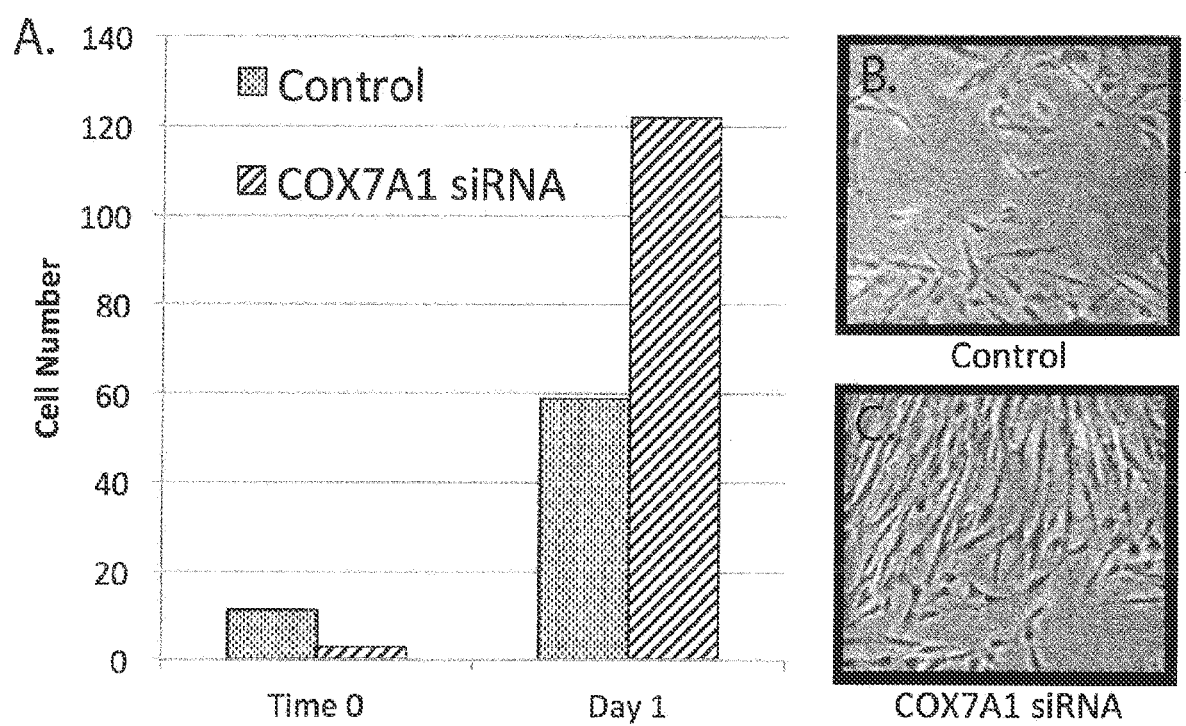

FIG. 16. Neonatal human foreskin fibroblasts that expressed COX7A1 were assayed for in vitro regeneration after silencing of the COX7A1 transcript compared to control using the in vitro wound repair assay described herein. A) Cell numbers were counted in representative fields within the wounded area at day 0 and day 1 for the control sample as well as the sample in which the iTR inhibitory gene COX7A1 transcript was down-regulated. B) Image of a representative field from the control sample. C) Image of a representative field from the COX7A1 siRNA field.

Figure 17:
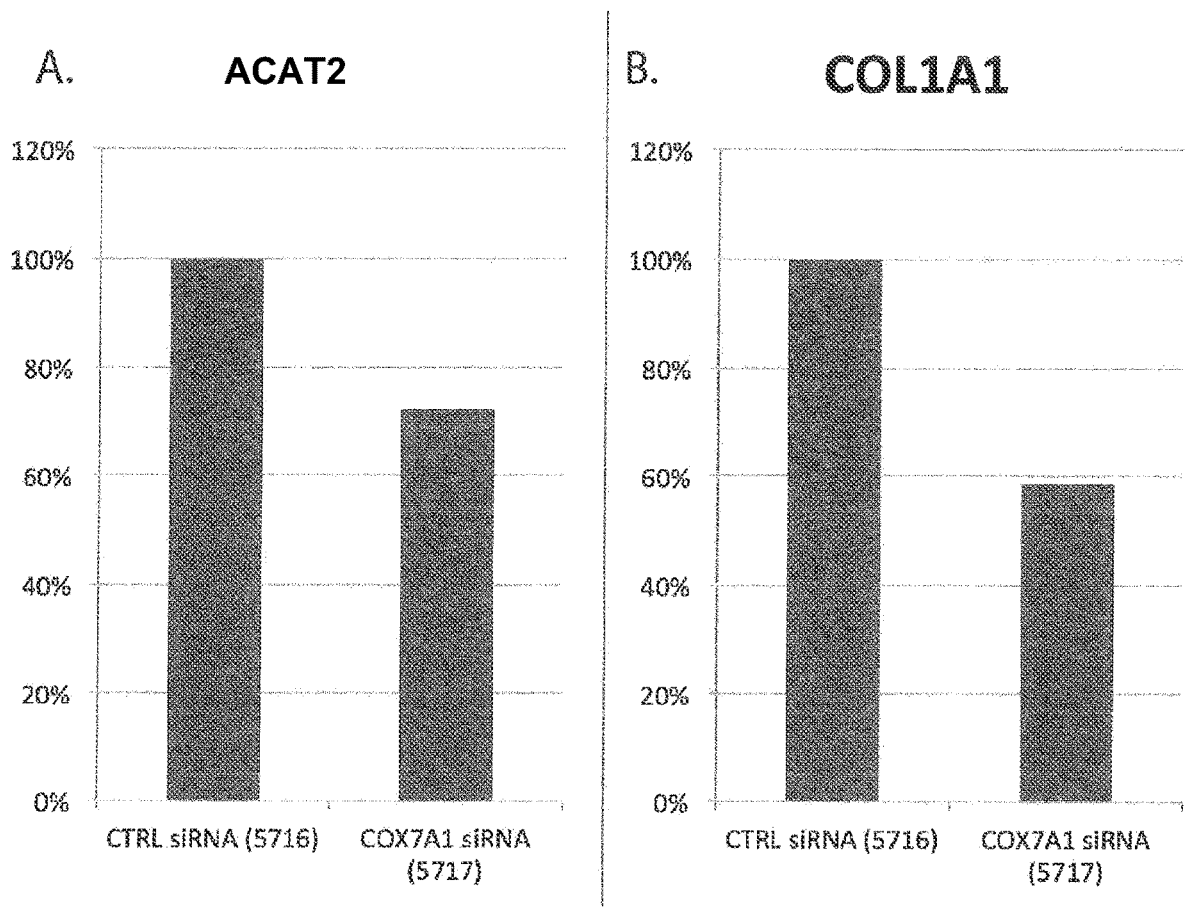

FIG. 17. Neonatal human foreskin fibroblasts that expressed COX7A1 were assayed for in vitro regeneration after silencing of the COX7A1 transcript compared to control using the in vitro wound repair assay described herein. A) Relative ACAT2 expression is shown in the control and COX7A1 down-regulated cells. B) Relative COL1A1 expression is shown in the control and COX7A1 down-regulated cells.

DETAILED DESCRIPTION OF THE INVENTION

Abbreviations
cGMP—Current Good Manufacturing Processes
CNS—Central Nervous System
DMEM—Dulbecco's modified Eagle's medium
DMSO—Dimethyl sulphoxide
DPBS—Dulbecco's Phosphate Buffered Saline
EC—Embryonal carcinoma
EC Cells—Embryonal carcinoma cells; hEC cells are human embryonal carcinoma cells
ECM—Extracellular Matrix
ED Cells—Embryo-derived cells; hED cells are human ED cells
EDTA—Ethylenediamine tetraacetic acid
EG Cells—Embryonic germ cells; hEG cells are human EG cells
ES Cells—Embryonic stem cells; hES cells are human ES cells
FACS—Fluorescence activated cell sorting
FBS—Fetal bovine serum
GMP—Good Manufacturing Practices
hED Cells—Human embryo-derived cells
hEG Cells—Human embryonic germ cells are stem cells derived from the primordial germ cells of fetal tissue.
MPS Cells—Human induced pluripotent stem cells are cells with properties similar to hES cells obtained from somatic cells after exposure to hES-specific transcription factors such as SOX2, KLF4, OCT4, MYC, or NANOG, LIN28, OCT4, and SOX2.

HSE—Human skin equivalents are mixtures of cells and biological or synthetic matrices manufactured for testing purposes or for therapeutic application in promoting wound repair.

ICM—Inner cell mass of the mammalian blastocyst-stage embryo.

iPS Cells—Induced pluripotent stem cells are cells with properties similar to hES cells obtained from somatic cells after exposure to ES-specific transcription factors such as SOX2, KLF4, OCT4, MYC, or NANOG, LIN28, OCT4, and SOX2.

iTR—Induced Tissue Regeneration

LOH—Loss of Heterozygosity

MEM—Minimal essential medium

NT—Nuclear Transfer

PBS—Phosphate buffered saline

PNS—Peripheral Nervous System

PS fibroblasts—Pre-scarring fibroblasts are fibroblasts derived from the skin of early gestational skin or derived from ED cells that display a prenatal pattern of gene expression in that they promote the rapid healing of dermal wounds without scar formation.

RFU—Relative Fluorescence Units

SCNT—Somatic Cell Nuclear Transfer

SFM—Serum-Free Medium

TR—Tissue Regeneration

Definitions

The term "analytical reprogramming technology" refers to a variety of methods to reprogram the pattern of gene expression of a somatic cell to that of a more pluripotent state, such as that of an iPS, ES, ED, EC or EG cell, wherein the reprogramming occurs in multiple and discrete steps and does not rely simply on the transfer of a somatic cell into an oocyte and the activation of that oocyte (see U.S. application No. 60/332,510, filed Nov. 26, 2001; Ser. No. 10/304,020, filed Nov. 26, 2002; PCT application no. PCT/US02/37899, filed Nov. 26, 2003; U.S. application No. 60/705,625, filed Aug. 3, 2005; U.S. application No. 60/729,173, filed Aug. 20, 2005; U.S. application No. 60/818,813, filed Jul. 5, 2006, PCT/US06/30632, filed Aug. 3, 2006, the disclosure of each of which is incorporated by reference herein).

The term "antibody", as used herein, means an immunoglobulin or a part thereof, and encompasses any polypeptide comprising an antigen binding site regardless of the source, method of production, or other characteristics. The term includes for example, polyclonal, monoclonal, monospecific, polyspecific, humanized, single chain, chimeric, synthetic, recombinant, hybrid, mutated, and CDR grafted antibodies. A part of an antibody can include any fragment which can bind antigen, for example, an Fab, F(ab')2, Fv, scFv.

The term "blastomere/morula cells" refers to blastomere or morula cells in a mammalian embryo or blastomere or morula cells cultured in vitro with or without additional cells including differentiated derivatives of those cells.

The term "cell expressing gene X", "gene X is expressed in a cell" (or cell population), or equivalents thereof means that analysis of the cell using a specific assay platform provided a positive result. The converse is also true (i.e., by a cell not expressing gene X, or equivalents, is meant that analysis of the cell using a specific assay platform provided a negative result). Thus, any gene expression result described herein is tied to the specific probe or probes employed in the assay platform (or platforms) for the gene indicated.

The term "cell line" refers to a mortal or immortal population of cells that is capable of propagation and expansion in vitro.

The term "cellular reconstitution" refers to the transfer of a nucleus of chromatin to cellular cytoplasm so as to obtain a functional cell.

The term "clonal" refers to a population of cells obtained from the expansion of a single cell into a population of cells all derived from that original single cells and not containing other cells.

The term "colony in situ differentiation" refers to the differentiation of colonies of cells (e.g., hES, hEG, hiPS, hEC or hED) in situ without removing or disaggregating the colonies from the culture vessel in which the colonies were propagated as undifferentiated stem cell lines. Colony in situ differentiation does not utilize the intermediate step of forming embryoid bodies, though embryoid body formation or other aggregation techniques such as the use of spinner culture may nevertheless follow a period of colony in situ differentiation.

The term "cytoplasmic bleb" refers to the cytoplasm of a cell bound by an intact or permeabilized but otherwise intact plasma membrane, but lacking a nucleus.

The term "differentiated cells" when used in reference to cells made by methods of this invention from pluripotent stem cells refer to cells having reduced potential to differentiate when compared to the parent pluripotent stem cells. The differentiated cells of this invention comprise cells that could differentiate further (i.e., they may not be terminally differentiated).

The term "direct differentiation" refers to process of differentiating using any method known in the art any of the following cell types: blastomere cells, morula cells, ICM cells, ED cells, or somatic cells reprogrammed to an undifferentiated state directly without the intermediate state of isolating and or propagating isolated undifferentiated stem cells, such as hES cells, as undifferentiated cell lines. A nonlimiting example of direct differentiation would be the culture of an intact human blastocyst into culture and the derivation of ED cells without the generation of a human ES cell line as was described (Bongso et al, 1994. Human Reproduction 9:2110).

The term "embryonic stages of development" refers to prenatal stages of development of cells, tissues or animals, specifically, the embryonic phases of development of cells compared to fetal and adult cells. In the case of the human species, the transition from embryonic to fetal development occurs at about 8 weeks of prenatal development, in mouse it occurs at approximately 16 days, and in the rat species, at approximately 17.5 days.

The term "embryonic stem cells" (ES cells) refers to cells derived from the inner cell mass of blastocysts, blastomeres, or morulae that have been serially passaged as cell lines while maintaining an undifferentiated state (e.g. expressing TERT, OCT4, and SSEA and TRA antigens specific for ES cells of the species). The ES cells may be derived from in vitro fertilization of an egg cell with sperm or DNA, nuclear transfer, parthenogenesis, or by means to generate hES cells with hemizygosity or homozygosity in the MHC region as is known in the art. While ES cells have historically been defined as cells capable of differentiating into all of the somatic cell types as well as germ line cells when transplanted into a preimplantation embryo, candidate ES cultures from many species, including human, typically do not contribute to germ line differentiation, and are therefore called "ES-like cells." It is commonly believed that human ES cells are in reality "ES-like", however, in this application we will use the term ES cells to refer to both ES and ES-like cell lines.

The term "human embryo-derived" ("hED") cells refers to blastomere-derived cells, morula-derived cells, blastocyst-derived cells including those of the inner cell mass, embryonic shield, or epiblast, or other totipotent or pluripotent stem cells of the early embryo, including primitive endoderm, ectoderm, mesoderm, and neural crest and their derivatives up to a state of differentiation correlating to the equivalent of the first eight weeks of normal human development, but excluding cells derived from hES cells that have been passaged as cell lines (see, e.g., U.S. Pat. Nos. 7,582,479; 7,217,569; 6,887,706; 6,602,711; 6,280,718; and 5,843,780 to Thomson). The hED cells may be derived from preimplantation embryos produced by fertilization of an egg cell with sperm or DNA, nuclear transfer, or chromatin transfer, an egg cell induced to form a parthenote through parthenogenesis, analytical reprogramming technology, or by means to generate hES cells with hemizygosity or homozygosity in the HLA region.

The term "human embryonic germ cells" (hEG cells) refer to pluripotent stem cells derived from the primordial germ cells of fetal tissue or maturing or mature germ cells such as oocytes and spermatogonial cells, that can differentiate into various tissues in the body. The hEG cells may also be derived from pluripotent stem cells produced by gynogenetic or androgenetic means, i.e., methods wherein the pluripotent cells are derived from oocytes containing only DNA of male or female origin and therefore will comprise all female-derived or male-derived DNA (see U.S. application No. 60/161,987, filed Oct. 28, 1999; Ser. No. 09/697,297, filed Oct. 27, 2000; Ser. No. 09/995,659, filed Nov. 29, 2001; Ser. No. 10/374,512, filed Feb. 27, 2003; PCT application no. PCT/US/00/29551, filed Oct. 27, 2000; the disclosures of which are incorporated herein in their entirety).

The term "human embryonic stem cells" (hES cells) refers to human ES cells (see, e.g., U.S. Pat. Nos. 7,582,479; 7,217,569; 6,887,706; 6,602,711; 6,280,718; and 5,843,780 to Thomson).

The term "human iPS cells" refers to cells with properties similar to hES cells, including the ability to form all three germ layers when transplanted into immunocompromised mice wherein said iPS cells are derived from cells of varied somatic cell lineages following exposure to de-differentiation factors, for example hES cell-specific transcription factor combinations: KLF4, SOX2, MYC, and OCT4 or SOX2, OCT4, NANOG, and LIN28. Any convenient combination of de-differentiation factors may be used to produce iPS cells. Said iPS cells may be produced by the expression of these genes through vectors such as retroviral, lentiviral or adenoviral vectors as is known in the art, or through the introduction of the factors as proteins, e.g., by permeabilization or other technologies. For descriptions of such exemplary methods see: PCT application number PCT/US2006/030632, filed on Aug. 3, 2006; U.S. application Ser. No. 11/989,988; PCT Application PCT/US2000/018063, filed on Jun. 30, 2000; U.S. application Ser. No. 09/736,268 filed on Dec. 15, 2000; U.S. application Ser. No. 10/831,599, filed Apr. 23, 2004; and U.S. Patent Publication 20020142397 (application Ser. No. 10/015,824, entitled "Methods for Altering Cell Fate"); U.S. Patent Publication 20050014258 (application Ser. No. 10/910,156, entitled "Methods for Altering Cell Fate"); U.S. Patent Publication 20030046722 (application Ser. No. 10/032,191, entitled "Methods for cloning mammals using reprogrammed donor chromatin or donor cells"); and U.S. Patent Publication 20060212952 (application Ser. No. 11/439,788, entitled "Methods for cloning mammals using reprogrammed donor chromatin or donor cells") all of which are incorporated herein by reference in their entirety.

The term "ICM cells" refers to the cells of the inner cell mass of a mammalian embryo or the cells of the inner cell mass cultured in vitro with or without the surrounding trophectodermal cells.

The term "induced tissue regeneration" refers to the use of the methods of the present invention to alter the molecular composition of fetal or adult mammalian cells such that said cells are capable or regenerating functional tissue following damage to that tissue wherein said regeneration would not otherwise occur without the intervention of the human hand as described infra.

The term "isolated" refers to a substance that is (i) separated from at least some other substances with which it is normally found in nature, usually by a process involving the hand of man, (ii) artificially produced (e.g., chemically synthesized), and/or (iii) present in an artificial environment or context (i.e., an environment or context in which it is not normally found in nature).

The term "iTR factors" refers to molecules that alter the levels of activators and TR inhibitors in a manner leading to TR in a tissue not naturally capable of TR.

The term "iTR genes" refers to genes that when altered in expression can cause induced tissue regeneration in tissues not normally capable of such regeneration.

The term "nucleic acid" is used interchangeably with "polynucleotide" and encompasses in various embodiments naturally occurring polymers of nucleosides, such as DNA and RNA, and non-naturally occurring polymers of nucleosides or nucleoside analogs. In some embodiments a nucleic acid comprises standard nucleosides (abbreviated A, G, C, T, U). In other embodiments a nucleic acid comprises one or more non-standard nucleosides. In some embodiments, one or more nucleosides are non-naturally occurring nucleosides or nucleotide analogs. A nucleic acid can comprise modified bases (for example, methylated bases), modified sugars (2'-fluoribose, arabinose, or hexose), modified phosphate groups or other linkages between nucleosides or nucleoside analogs (for example, phosphorothioates or 5'-N-phosphoramidite linkages), locked nucleic acids, or morpholinos. In some embodiments, a nucleic acid comprises nucleosides that are linked by phosphodiester bonds, as in DNA and RNA. In some embodiments, at least some nucleosides are linked by non-phosphodiester bond(s). A nucleic acid can be single-stranded, double-stranded, or partially double-stranded. An at least partially double-stranded nucleic acid can have one or more overhangs, e.g., 5' and/or 3' overhang(s). Nucleic acid modifications (e.g., nucleoside and/or backbone modifications, including use of non-standard nucleosides) known in the art as being useful in the context of RNA interference (RNAi), aptamer, or antisense-based molecules for research or therapeutic purposes are contemplated for use in various embodiments of the instant invention. See, e.g., Crooke, S T (ed.) Antisense drug technology: principles, strategies, and applications, Boca Raton: CRC Press, 2008; Kurreck, J. (ed.) Therapeutic oligonucleotides, RSC biomolecular sciences. Cambridge: Royal Society of Chemistry, 2008. In some embodiments, a modification increases half-life and/or stability of a nucleic acid, e.g., in vivo, relative to RNA or DNA of the same length and strandedness. In some embodiments, a modification decreases immunogenicity of a nucleic acid relative to RNA or DNA of the same length and strandedness. In some embodiments, between 5% and 95% of the nucleosides in one or both strands of a nucleic acid is modified. Modifications may be located uniformly or nonuniformly, and the location of the modifications (e.g., near the middle, near or at the ends, alternating, etc.) can be selected to enhance desired properties. A nucleic acid may comprise a detectable label, e.g., a fluorescent dye, radioactive atom, etc. "Oligonucleotide" refers to a relatively short nucleic acid, e.g., typically between about 4 and about 60 nucleotides long. Where reference is made herein to a polynucleotide, it is understood that both DNA, RNA, and in each case both single- and double-stranded forms (and complements of each single-stranded molecule) are provided. "Polynucleotide sequence" as used herein can refer to the polynucleotide material itself and/or to the sequence information (i.e, the succession of letters used as abbreviations for bases) that biochemically characterizes a specific nucleic acid. A polynucleotide sequence presented herein is presented in a 5' to 3' direction unless otherwise indicated.

The term "oligoclonal" refers to a population of cells that originated from a small population of cells, typically 2-1000 cells, that appear to share similar characteristics such as morphology or the presence or absence of markers of differentiation that differ from those of other cells in the same culture. Oligoclonal cells are isolated from cells that do not share these common characteristics, and are allowed to proliferate, generating a population of cells that are essentially entirely derived from the original population of similar cells.

The term "pluripotent stem cells" refers to animal cells capable of differentiating into more than one differentiated cell type. Such cells include hES cells, blastomere/morula cells and their derived hED cells, hiPS cells, hEG cells, hEC cells, and adult-derived cells including mesenchymal stem cells, neuronal stem cells, and bone marrow-derived stem cells. Pluripotent stem cells may be genetically modified or not genetically modified. Genetically modified cells may include markers such as fluorescent proteins to facilitate their identification within the egg.

The term "polypeptide" refers to a polymer of amino acids. The terms "protein" and "polypeptide" are used interchangeably herein. A peptide is a relatively short polypeptide, typically between about 2 and 60 amino acids in length. Polypeptides used herein typically contain the standard amino acids (i.e., the 20 L-amino acids that are most commonly found in proteins). However, a polypeptide can contain one or more non-standard amino acids (which may be naturally occurring or non-naturally occurring) and/or amino acid analogs known in the art in certain embodiments. One or more of the amino acids in a polypeptide may be modified, for example, by the addition of a chemical entity such as a carbohydrate group, a phosphate group, a fatty acid group, a linker for conjugation, functionalization, etc. A polypeptide that has a nonpolypeptide moiety covalently or noncovalently associated therewith is still considered a "polypeptide". Polypeptides may be purified from natural sources, produced using recombinant DNA technology, synthesized through chemical means such as conventional solid phase peptide synthesis, etc. The term "polypeptide sequence" or "amino acid sequence" as used herein can refer to the polypeptide material itself and/or to the sequence information (i.e., the succession of letters or three letter codes used as abbreviations for amino acid names) that biochemically characterizes a polypeptide. A polypeptide sequence presented herein is presented in an N-terminal to C-terminal direction unless otherwise indicated. A polypeptide may be cyclic or contain a cyclic portion. Where a naturally occurring polypeptide is discussed herein, it will be understood that the invention encompasses embodiments that relate to any isoform thereof (e.g., different proteins arising from the same gene as a result of alternative splicing or editing of mRNA or as a result of different alleles of a gene, e.g., alleles differing by one or more single nucleotide polymorphisms (typically such alleles will be at least 95%, 96%, 97%, 98%, 99%, or more identical to a reference or consensus sequence). A polypeptide may comprise a sequence that targets it for secretion or to a particular intracellular compartment (e.g., the nucleus) and/or a sequence targets the polypeptide for post-translational modification or degradation. Certain polypeptides may be synthesized as a precursor that undergoes post-translational cleavage or other processing to become a mature polypeptide. In some instances, such cleavage may only occur upon particular activating events. Where relevant, the invention provides embodiments relating to precursor polypeptides and embodiments relating to mature versions of a polypeptide.

The term "pooled clonal" refers to a population of cells obtained by combining two or more clonal populations to generate a population of cells with a uniformity of markers such as markers of gene expression, similar to a clonal population, but not a population wherein all the cells were derived from the same original clone. Said pooled clonal lines may include cells of a single or mixed genotypes. Pooled clonal lines are especially useful in the cases where clonal lines differentiate relatively early or alter in an undesirable way early in their proliferative lifespan.

The term "prenatal" refers to a stage of embryonic development of a placental mammal prior to which an animal is not capable of viability apart from the uterus.

The term "primordial stem cells" refers collectively to pluripotent stem cells capable of differentiating into cells of all three primary germ layers: endoderm, mesoderm, and ectoderm, as well as neural crest. Therefore, examples of primordial stem cells would include but not be limited by human or non-human mammalian ES cells or cell lines, blastomere/morula cells and their derived ED cells, iPS, and EG cells.

The term "purified" refers to agents or entities (e.g., compounds) that have been separated from most of the components with which they are associated in nature or when originally generated. In general, such purification involves action of the hand of man. Purified agents or entities may be partially purified, substantially purified, or pure. Such agents or entities may be, for example, at least 50%, 60%, 70%, 75%, 80%, 85%, 90%, 95%, 96%, 97%, 98%, 99%, or more than 99% pure. In some embodiments, a nucleic acid or polypeptide is purified such that it constitutes at least 75%, 80%, 855%, 90%, 95%, 96%, 97%, 98%, 99%, or more, of the total nucleic acid or polypeptide material, respectively, present in a preparation. Purity can be based on, e.g., dry weight, size of peaks on a chromatography tracing, molecular abundance, intensity of bands on a gel, or intensity of any signal that correlates with molecular abundance, or any art-accepted quantification method. In some embodiments, water, buffers, ions, and/or small molecules (e.g., precursors such as nucleotides or amino acids), can optionally be present in a purified preparation. A purified molecule may be prepared by separating it from other substances (e.g., other cellular materials), or by producing it in such a trimmer to achieve a desired degree of purity. In some embodiments, a purified molecule or composition refers to a molecule or composition that is prepared using any art-accepted method of purification. In some embodiments "partially purified" means that a molecule produced by a cell is no longer present within the cell, e.g., the cell has been lysed and, optionally, at least some of the cellular material (e.g., cell wall, cell membrane(s), cell organelle(s)) has been removed.

The term "RNA interference" (RNAi) is used to refer to a phenomenon whereby double-stranded RNA (dsRNA) triggers the sequence-specific degradation or translational repression of a corresponding mRNA having complementarity to a strand of the dsRNA. It will be appreciated that the complementarity between the strand of the dsRNA and the mRNA need not be 100% but need only be sufficient to mediate inhibition of gene expression (also referred to as "silencing" or "knockdown"). For example, the degree of complementarity is such that the strand can either (i) guide cleavage of the mRNA in the RNA-induced silencing complex (RISC); or (ii) cause translational repression of the mRNA. In certain embodiments the double-stranded portion of the RNA is less than about 30 nucleotides in length, e.g., between 17 and 29 nucleotides in length. In certain embodiments a first strand of the dsRNA is at least 80%, 85%, 90%, 95%, or 100% complementary to a target mRNA and the other strand of the dsRNA is at least 80%, 85%, 90%, 95%, or 100% complementary to the first strand. In mammalian cells, RNAi may be achieved by introducing an appropriate double-stranded nucleic acid into the cells or expressing a nucleic acid in cells that is then processed intracellularly to yield dsRNA therein. Nucleic acids capable of mediating RNAi are referred to herein as "RNAi agents". Exemplary nucleic acids capable of mediating RNAi are a short hairpin RNA (shRNA), a short interfering RNA (siRNA), and a microRNA precursor. These terms are well known and are used herein consistently with their meaning in the art. siRNAs typically comprise two separate nucleic acid strands that are hybridized to each other to form a duplex. They can be synthesized in vitro, e.g., using standard nucleic acid synthesis techniques. siRNAs are typically double-stranded oligonucleotides having 16-30, e.g., 16, 17, 18, 19, 20, 21, 22, 23, 24, 25, 26, 27, 28, 29, or 30 nucleotides (nt) in each strand, wherein the double-stranded oligonucleotide comprises a double-stranded portion between 15 and 29 nucleotides long and either or both of the strands may comprise a 3' overhang between, e.g., 1-5 nucleotides long, or either or both ends can be blunt. In some embodiments, a siRNA comprises strands between 19 and 25 nt, e.g., between 21 and 23 nucleotides long, wherein one or both strands comprises a 3' overhang of 1-2 nucleotides. One strand of the double-stranded portion of the siRNA (termed the "guide strand" or "antisense strand") is substantially complementary (e.g., at least 80% or more, e.g., 85%, 90%, 95%, or 100%) complementary to (e.g., having 3, 2, 1, or 0 mismatched nucleotide(s)) a target region in the mRNA, and the other double-stranded portion is substantially complementary to the first double-stranded portion. In certain embodiments, the guide strand is 100% complementary to a target region in an mRNA and the other passenger strand is 100% complementary to the first double-stranded portion (it is understood that, in various embodiments, the 3' overhang portion of the guide strand, if present, may or may not be complementary to the mRNA when the guide strand is hybridized to the mRNA). In some embodiments, a shRNA molecule is a nucleic acid molecule comprising a stem-loop, wherein the double-stranded stem is 16-30 nucleotides long and the loop is about 1-10 nucleotides long. siRNA can comprise a wide variety of modified nucleosides, nucleoside analogs and can comprise chemically or biologically modified bases, modified backbones, etc. Without limitation, any modification recognized in the art as being useful for RNAi can be used. Some modifications result in increased stability, cell uptake, potency, etc. Some modifications result in decreased immunogenicity or clearance. In certain embodiments the siRNA comprises a duplex about 19-23 (e.g., 19, 20, 21, 22, or 23) nucleotides in length and, optionally, one or two 3' overhangs of 1-5 nucleotides in length, which may be composed of deoxyribonucleotides. shRNA comprise a single nucleic acid strand that contains two complementary portions separated by a predominantly non-self complementary region. The complementary portions hybridize to form a duplex structure and the non-self complementary region forms a loop connecting the 3' end of one strand of the duplex and the 5' end of the other strand. shRNAs undergo intracellular processing to generate siRNAs. Typically, the loop is between 1 and 8, e.g., 2-6 nucleotides long.

MicroRNAs (miRNAs) are small, naturally occurring, non-coding, single-stranded RNAs of about 21-25 nucleotides (in mammalian systems) that inhibit gene expression in a sequence-specific manner. They are generated intracellularly from precursors (pre-miRNA) having a characteristic secondary structure comprised of a short hairpin (about 70 nucleotides in length) containing a duplex that often includes one or more regions of imperfect complementarity which is in turn generated from a larger precursor (pre-miRNA). Naturally occurring miRNAs are typically only partially complementary to their target mRNA and often act via translational repression. RNAi agents modeled on endogenous miRNA or miRNA precursors are of use in certain embodiments of the invention. For example, an siRNA can be designed so that one strand hybridizes to a target mRNA with one or more mismatches or bulges mimicking the duplex formed by a miRNA and its target mRNA. Such siRNA may be referred to as miRNA mimics or miRNA-like molecules. miRNA mimics may be encoded by precursor nucleic acids whose structure mimics that of naturally occurring miRNA precursors.

In certain embodiments an RNAi agent is a vector (e.g., a plasmid or virus) that comprises a template for transcription of a siRNA (e.g., as two separate strands that can hybridize to each other), shRNA, or microRNA precursor. Typically the template encoding the siRNA, shRNA, or miRNA precursor is operably linked to expression control sequences (e.g., a promoter), as known in the art. Such vectors can be used to introduce the template into vertebrate cells, e.g., mammalian cells, and result in transient or stable expression of the siRNA, shRNA, or miRNA precursor. Precursors (shRNA or miRNA precursors) are processed intracellularly to generate siRNA or miRNA.

In general, small RNAi agents such as siRNA can be chemically synthesized or can be transcribed in vitro or in vivo from a DNA template either as two separate strands that then hybridize, or as a shRNA which is then processed to generate a siRNA. Often RNAi agents, especially those comprising modifications, are chemically synthesized. Chemical synthesis methods for oligonucleotides are well known in the art.

The term "small molecule" as used herein, is an organic molecule that is less than about 2 kilodaltons (KDa) in mass. In some embodiments, the small molecule is less than about 1.5 KDa, or less than about 1 KDa. In some embodiments, the small molecule is less than about 800 daltons (Da), 600 Da, 500 Da, 400 Da, 300 Da, 200 Da, or 100 Da. Often, a small molecule has a mass of at least 50 Da. In some embodiments, a small molecule contains multiple carbon-carbon bonds and can comprise one or more heteroatoms and/or one or more functional groups important for structural interaction with proteins (e.g., hydrogen bonding), e.g., an amine, carbonyl, hydroxyl, or carboxyl group, and in some embodiments at least two functional groups. Small molecules often comprise one or more cyclic carbon or heterocyclic structures and/or aromatic or polyaromatic structures, optionally substituted with one or more of the above functional groups. In some embodiments, a small molecule is non-polymeric. In some embodiments, a small molecule is not an amino acid. In some embodiments, a small molecule is not a nucleotide. In some embodiments, a small molecule is not a saccharide.

The term "subject" can be any multicellular animal. A subject may be a vertebrate, e.g., a mammal or avian. Exemplary mammals include, e.g., humans, nonhuman primates, rodents (e.g., mouse, rat, rabbit), ungulates (e.g., ovine, bovine, equine, caprine species), canines, and felines. A subject may be an individual to whom a compound is to be delivered, e.g., for experimental, diagnostic, and/or therapeutic purposes or from whom a sample is obtained or on whom a diagnostic procedure is performed (e.g., a sample or procedure that will be used to assess tissue damage and/or to assess the effect of a compound of the invention).

The term "tissue damage" is used herein to refer to any type of damage or injury to cells, tissues, organs, or other body structures. The term encompasses, in various embodiments, degeneration due to disease, damage due to physical trauma or surgery, damage caused by exposure to deleterious substance, and other disruptions in the structure and/or functionality of cells, tissues, organs, or other body structures.

The term "tissue regeneration" or "TR" refers to at least partial regeneration, replacement, restoration, or regrowth of a tissue, organ, or other body structure, or portion thereof, following loss, damage, or degeneration, where said tissue regeneration but for the methods described in the present invention would not take place. Examples of tissue regeneration include the regrowth of severed digits or limbs including the regrowth of cartilage, bone, muscle, tendons, and ligaments, the regrowth (which may be scarless or not) of bone, cartilage, skin, or muscle that has been lost due to injury or disease, with an increase in size and cell number of an injured or diseased organ such that the tissue or organ approximates the normal size of the tissue or organ or its size prior to injury or disease. Depending on the tissue type, tissue regeneration can occur via a variety of different mechanisms such as, for example, the rearrangement of pre-existing cells and/or tissue (e.g., through cell migration), the division of adult somatic stem cells or other progenitor cells and differentiation of at least some of their descendants, and/or the dedifferentiation, transdifferentiation, and/or proliferation of cells.

The term "TR activator genes" refers to genes whose lack of expression in fetal and adult cells but whose expression in embryonic phases of development facilitate TR.

The term "TR inhibitor genes" refers to genes whose expression in fetal and adult animals inhibit TR.

The term "treat", "treating", "treatment," "therapy", "therapeutic" and similar terms in regard to a subject refer to providing medical and/or surgical management of the subject. Treatment can include, but is not limited to, administering a compound or composition (e.g., a pharmaceutical composition such as a cellular composition) to a subject. Treatment of a subject according to the instant invention is typically undertaken in an effort to promote regeneration, e.g., in a subject who has suffered tissue damage or is expected to suffer tissue damage (e.g., a subject who will undergo surgery). Treatment as used herein includes prophylaxis, and the reduction of one or more symptoms associated with a disease or condition. The effect of treatment can generally include increased regeneration, reduced scarring, and/or improved structural or functional outcome following tissue damage (as compared with the outcome in the absence of treatment), and/or can include reversal or reduction in severity or progression of a degenerative disease.

The term "variant" as applied to a particular polypeptide refers to a polypeptide that differs from such polypeptide (sometimes referred to as the "original polypeptide") by one or more amino acid alterations, e.g., addition(s), deletion(s), and/or substitution(s). Sometimes an original polypeptide is a naturally occurring polypeptide (e.g., from human or non-human animal) or a polypeptide identical thereto. Variants may be naturally occurring or created using, e.g., recombinant DNA techniques or chemical synthesis. An addition can be an insertion within the polypeptide or an addition at the N- or C-terminus. In some embodiments, the number of amino acids substituted, deleted, or added can be for example, about 1 to 30, e.g., about 1 to 20, e.g., about 1 to 10, e.g., about 1 to 5, e.g., 1, 2, 3, 4, or 5. In some embodiments, a variant comprises a polypeptide whose sequence is homologous to the sequence of the original polypeptide over at least 50 amino acids, at least 100 amino acids, at least 150 amino acids, or more, up to the full length of the original polypeptide (but is not identical in sequence to the original polypeptide), e.g., the sequence of the variant polypeptide is at least 50%, 60%, 70%, 75%, 80%, 85%, 90%, 95%, 96%, 97%, 98%, 99%, or more identical to the sequence of the original polypeptide over at least 50 amino acids, at least 100 amino acids, at least 150 amino acids, or more, up to the full length of the original polypeptide. In some embodiments, a variant comprises a polypeptide at least 50%, 60%, 70%, 75%, 80%, 85%, 90%, 91%, 92%, 93%, 94%, 95%, 96%, 97%, 98%, 99%, 99.5% or more identical to an original polypeptide over at least 50%, 60%, 70%, 80%, 85%, 90%, 91%, 92%, 93%, 94%, 95%, 96%, 97%, 98%, 99%, or 100% of the length of the original polypeptide. In some embodiments a variant comprises at least one functional or structural domain, e.g., a domain identified as such in the Conserved Domain Database (CDD) of the National Center for Biotechnology Information (www.ncbi.nib.gov), e.g., an NCBI-curated domain.

In some embodiments one, more than one, or all biological functions or activities of a variant or fragment is substantially similar to that of the corresponding biological function or activity of the original molecule. In some embodiments, a functional variant retains at least 10%, 20%, 30%, 40%, 50%, 60%, 70%, 80%, 90%, 95%, 96%, 97%, 98%, 99%, or more of the activity of the original polypeptide, e.g., about equal activity. In some embodiments, the activity of a variant is up to approximately 100%, approximately 125%, or approximately 150% of the activity of the original molecule. In other nonlimiting embodiments an activity of a variant or fragment is considered substantially similar to the activity of the original molecule if the amount or concentration of the variant needed to produce a particular effect is within 0.5 to 5-fold of the amount or concentration of the original molecule needed to produce that effect.

In some embodiments amino acid "substitutions" in a variant are the result of replacing one amino acid with another amino acid having similar structural and/or chemical properties, i.e., conservative amino acid replacements. "Conservative" amino acid substitutions be made on the basis of similarity in any of a variety or properties such as side chain size, polarity, charge, solubility, hydrophobicity, hydrophilicity, and/or amphipathicity of the residues involved. For example, the non-polar (hydrophobic) amino acids include alanine, leucine, isoleucine, valine, glycine, proline, phenylalanine, tryptophan and methionine. The polar (hydrophilic), neutral amino acids include serine, threonine, cysteine, tyrosine, asparagine, and glutamine. The positively charged (basic) amino acids include arginine, lysine and histidine. The negatively charged (acidic) amino acids include aspartic acid and glutamic acid. Within a particular group, certain substitutions may be of particular interest, e.g., replacements of leucine by isoleucine (or vice versa), serine by threonine (or vice versa), or alanine by glycine (or vice versa). Of course non-conservative substitutions are often compatible with retaining function as well. In some embodiments, a substitution or deletion does not alter or delete an amino acid important for activity. Insertions or deletions may range in size from about 1 to 20 amino acids, e.g., 1 to 10 amino acids. In some instances larger domains may be removed without substantially affecting function. In certain embodiments of the invention the sequence of a variant can be obtained by making no more than a total of 5, 10, 15, or 20 amino acid additions, deletions, or substitutions to the sequence of a naturally occurring enzyme. In some embodiments no more than 1%, 5%, 10%, or 20% of the amino acids in a polypeptide are insertions, deletions, or substitutions relative to the original polypeptide. Guidance in determining which amino acid residues may be replaced, added, or deleted without eliminating or substantially reducing activities of interest, may be obtained by comparing the sequence of the particular polypeptide with that of homologous polypeptides (e.g., from other organisms) and minimizing the number of amino acid sequence changes made in regions of high homology (conserved regions) or by replacing amino acids with those found in homologous sequences since amino acid residues that are conserved among various species are more likely to be important for activity than amino acids that are not conserved.

In some embodiments, a variant of a polypeptide comprises a heterologous polypeptide portion. The heterologous portion often has a sequence that is not present in or homologous to the original polypeptide. A heterologous portion may be, e.g., between 5 and about 5,000 amino acids long, or longer. In some embodiments it is between 5 and about 1,000 amino acids long. In some embodiments, a heterologous portion comprises a sequence that is found in a different polypeptide, e.g., a functional domain. In some embodiments, a heterologous portion comprises a sequence useful for purifying, expressing, solubilizing, and/or detecting the polypeptide. In some embodiments, a heterologous portion comprises a polypeptide "tag", e.g., an affinity tag or epitope tag. For example, the tag can be an affinity tag (e.g., HA, TAP, Myc, 6× His, Flag, GST), fluorescent or luminescent protein (e.g., EGFP, ECFP, FYFP, Cerulean, DsRed, mCherry), solubility-enhancing tag (e.g., a SUMO tag, NUS A tag, SNUT tag, or a monomeric mutant of the Ocr protein of bacteriophage T7). See, e.g., Esposito D and Chatterjee D K. *Curr Opin Biotechnol.;* 17(4):353-8 (2006). In some embodiments, a tag can serve multiple functions. A tag is often relatively small, e.g., ranging from a few amino acids up to about 100 amino acids long. In some embodiments a tag is more than 100 amino acids long, e.g., up to about 500 amino acids long, or more. In some embodiments, a polypeptide has a tag located at the N- or C-terminus, e.g., as an N- or C-terminal fusion. The polypeptide could comprise multiple tags. In some embodiments, a 6.times. His tag and a NUS tag are present, e.g., at the N-terminus. In some embodiments, a tag is cleavable, so that it can be removed from the polypeptide, e.g., by a protease. In some embodiments, this is achieved by including a sequence encoding a protease cleavage site between the sequence encoding the portion homologous to the original polypeptide and the tag. Exemplary proteases include, e.g., thrombin, TEV protease, Factor Xa, PreScission protease, etc. In some embodiments, a "self-cleaving" tag is used. See, e.g., PCT/US05/05763. Sequences encoding a tag can be located 5' or 3' with respect to a polynucleotide encoding the polypeptide (or both). In some embodiments a tag or other heterologous sequence is separated from the rest of the polypeptide by a polypeptide linker. For example, a linker can be a short polypeptide (e.g., 15-25 amino acids). Often a linker is composed of small amino acid residues such as serine, glycine, and/or alanine. A heterologous domain could comprise a transmembrane domain, a secretion signal domain, etc.

In certain embodiments of the invention a fragment or variant, optionally excluding a heterologous portion, if present, possesses sufficient structural similarity to the original polypeptide so that when its 3-dimensional structure (either actual or predicted structure) is superimposed on the structure of the original polypeptide, the volume of overlap is at least 70%, preferably at least 80%, more preferably at least 90% of the total volume of the structure of the original polypeptide. A partial or complete 3-dimensional structure of the fragment or variant may be determined by crystallizing the protein, which can be done using standard methods. Alternately, an NMR solution structure can be generated, also using standard methods. A modeling program such as MODELER (Sali, A. and Blundell, T L, *J. Mol. Biol.,* 234, 779-815, 1993), or any other modeling program, can be used to generate a predicted structure. If a structure or predicted structure of a related polypeptide is available, the model can be based on that structure. The PROSPECT-PSPP suite of programs can be used (Guo, J T, et al., *Nucleic Acids Res.* 32 (Web Server issue): W522-5, Jul. 1, 2004). Where embodiments of the invention relate to variants of a polypeptide, it will be understood that polynucleotides encoding the variant are provided.

The term "vector" is used herein to refer to a nucleic acid or a virus or portion thereof (e.g., a viral capsid or genome) capable of mediating entry of, e.g., transferring, transporting, etc., a nucleic acid molecule into a cell. Where the vector is a nucleic acid, the nucleic acid molecule to be transferred is generally linked to, e.g., inserted into, the vector nucleic acid molecule. A nucleic acid vector may include sequences that direct autonomous replication (e.g., an origin of replication), or may include sequences sufficient to allow integration of part or all of the nucleic acid into host cell DNA. Useful nucleic acid vectors include, for example, DNA or RNA plasmids, cosmids, and naturally occurring or modified viral genomes or portions thereof or nucleic acids (DNA or RNA) that can be packaged into viral) capsids. Plasmid vectors typically include an origin of replication and one or more selectable markers. Plasmids may include part or all of a viral genome (e.g., a viral promoter, enhancer, processing or packaging signals, etc.). Viruses or portions thereof that can be used to introduce nucleic acid molecules into cells are referred to as viral vectors. Useful viral vectors include adenoviruses, adeno-associated viruses, retroviruses, lentiviruses, vaccinia virus and other poxviruses, herpesviruses (e.g., herpes simplex virus), and others. Viral vectors may or may not contain sufficient viral genetic information for production of infectious virus when introduced into host cells, i.e., viral vectors may be replication-defective, and such replication-defective viral vectors may be preferable for therapeutic use. Where sufficient information is lacking it may, but need not be, supplied by a host cell or by another vector introduced into the cell. The nucleic acid to be transferred may be incorporated into a naturally occurring or modified viral genome or a portion thereof or may be present within the virus or viral capsid as a separate nucleic acid molecule. It will be appreciated that certain plasmid vectors that include part or all of a viral genome, typically including viral genetic information sufficient to direct transcription of a nucleic acid that can be packaged into a viral capsid and/or sufficient to give rise to a nucleic acid that can be integrated into the host cell genome and/or to give rise to infectious virus, are also sometimes referred to in the art as viral vectors. Vectors may contain one or more nucleic acids encoding a marker suitable for use in the identifying and/or selecting cells that have or have not been transformed or transfected with the vector. Markers include, for example, proteins that increase or decrease either resistance or sensitivity to antibiotics (e.g., an antibiotic-resistance gene encoding a protein that confers resistance to an antibiotic such as puromycin, hygromycin or blasticidin) or other compounds, enzymes whose activities are detectable by assays known in the art (e.g., beta.-galactosidase or alkaline phosphatase), and proteins or RNAs that detectably affect the phenotype of transformed or transfected cells (e.g., fluorescent proteins). Expression vectors are vectors that include regulatory sequence(s), e.g., expression control sequences such as a promoter, sufficient to direct transcription of an operably linked nucleic acid. Regulatory sequences may also include enhancer sequences or upstream activator sequences. Vectors may optionally include 5' leader or signal sequences. Vectors may optionally include cleavage and/or polyadenylations signals and/or a 3' untranslated regions. Vectors often include one or more appropriately positioned sites for restriction enzymes, to facilitate introduction into the vector of the nucleic acid to be expressed. An expression vector comprises sufficient cis-acting elements for expression; other elements required or helpful for expression can be supplied by the host cell or in vitro expression system.

Various techniques may be employed for introducing nucleic acid molecules into cells. Such techniques include chemical-facilitated transfection using compounds such as calcium phosphate, cationic lipids, cationic polymers, liposome-mediated transfection, non-chemical methods such as electroporation, particle bombardment, or microinjection, and infection with a virus that contains the nucleic acid molecule of interest (sometimes termed "transduction"). Markers can be used for the identification and/or selection of cells that have taken up the vector and, typically, express the nucleic acid. Cells can be cultured in appropriate media to select such cells and, optionally, establish a stable cell line.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The present invention provides compounds, compositions, and methods useful for performing somatic iTR in the fetal, neonatal, infant, or adult phases of development in mammalian species, such as humans, where the patterns of gene expression that impart TR in the embryonic phases have been lost. In one aspect, the invention provides a method of identifying the genes regulating TR in mammalian species, including primate species, more specifically, the human species, wherein said genes are identified by comparing the expression of genes that encode mRNAs and noncoding RNAs or splice variants in said RNAs that are differentially expressed in the embryonic stages of development compared to fetal and adult stages of development. More specifically, said methods identify genes encoding mRNAs and noncoding RNAs differentially expressed in multiple diverse somatic cell types in prenatal stages of development, specifically, the embryonic phases of development (before the transition point from embryonic to fetal development) compared to fetal and adult cells (subsequent to the transition point from embryonic to fetal development). In the case of the human species, the transition from embryonic to fetal development occurs at about 8 weeks of prenatal development, in mouse it occurs at approximately 16 days, and in the rat species, at approximately 17.5 days.

In another aspect of the present invention, pluripotent stem cell-derived clonal, oligoclonal, pooled clonal, or pooled oligoclonal embryonic progenitor cell lines displaying gene expression patterns specific to the embryonic phase of mammalian development are utilized as a source of coding and noncoding RNAs and compared to the coding and noncoding RNAs in cells and tissues from fetal or adult-derived sources to identify genes encoding mRNAs and noncoding RNAs or splice variants in said genes regulating TR and the repression of TR in fetal and adult tissues compared to cells in the embryonic phases of development.

In another aspect of the invention, transcriptional regulatory genes differentially expressed in diverse types of somatic cells in the embryonic phases of development are compared to diverse types of somatic cells in phases of development after the embryonic phases such as adult cell types incapable of participating in TR, to identify those genes whose altered expression of alterations in splice variants is causative in the repression of tissue regeneration capacity in adult mammals. In some embodiments, methods of identifying genes whose expression or repression are capable of iTR comprises comparing the transcriptome of clonal, oligoclonal, or pooled clonal or pooled oligoclonal hPS cell-derived embryonic progenitor cell lines with the transcriptome of adult-derived cells or tissues of diverse types to identify genes commonly expressed in the embryonic progenitors or with RNA splice variants in the embryonic progenitors but not expressed or expressed at markedly lower levels in adult-derived cells, or alternatively, genes expressed in adult-derived cells or RNAs with splice variants, but not expressed or expressed at markedly lower levels in clonal, oligoclonal, or pooled clonal or pooled oligoclonal hPS cell-derived embryonic progenitor cell lines. In another embodiment, candidate iTR genes that are both expressed at higher levels in embryonic progenitor cells compared to adult-derived cells and which are also implicated in oncogenesis, or genes that are both expressed at lower levels in embryonic progenitor cells compared to adult-derived cells and which are also implicated in tumor suppression, are identified as candidate iTR genes.

In another aspect, the invention provides methods of screening combinations of iTR genes in diverse cell and tissue types to identify combinations of factors and/or repressors optimized for regeneration of particular cell and tissue types.

In another aspect, the invention provides methods of modifying the expression of iTR genes in cultured cells to restore them to a state wherein they are capable of participating in iTR when transplanted into a tissue otherwise incapable of undergoing sufficient TR.

In another aspect of the invention, the telomerase catalytic component, including but not limited to the human gene TERT, is transiently expressed in the target cells or tissues in which TR is to be induced, to extend the proliferative capacity of the somatic cells thereby facilitating TR. In another aspect of the invention, the telomerase catalytic component, including the human gene TERT is transiently expressed (as opposed to constitutively expressed) in the target cells or tissues to extend the proliferative capacity of the somatic cells without immortalizing the cells.

In another aspect, the invention provides methods of modifying the expression of iTR genes in cells in vivo to restore them to a state wherein they are capable of participating in iTR. In some embodiments iTR gene expression is modified in vitro.

In another aspect, the invention provides a method of identifying a candidate modulator of TR activity comprising: (i) providing a composition comprising: (a) the candidate modulator of TR activity in a purified state or in a mixture with other molecules; (b) somatic cells not capable of TR wherein said cells express a fetal or adult pattern of gene expression as opposed to an embryonic pattern of gene expression; (c) a reporter construct present within the somatic cells or within extracts of said cells incapable of TR wherein the promoter of a gene differentially regulated in somatic cells in the embryonic phases of development compared to fetal and adult stages drives the expression of a reporter gene; and (ii) determining whether the candidate modulator affects expression of the reporter gene, wherein altered expression of the reporter gene as compared with expression of the gene in the absence of the candidate modulator indicates that the compound modulates iTR activity.

In some embodiments, a method of identifying a candidate modulator of TR further comprises administering a candidate compound identified as a modulator of TR to a subject. Suitable subjects include any animal, including, for example, a mammal such as a human, a non-human primate, ungulates and other farm animals such as a cow, a sheep, a horse, a goat, a pig, domesticated mammals such as a cat or dog and a rodent such as a mouse, a rat, a rabbit, a guinea pig.

In some embodiments, a method of identifying a compound further comprises administering the compound to a subject. In some embodiments, the subject is a non-human animal, e.g., a non-human animal that serves as a model for TR or wound healing. In some embodiments, the subject is a human.

In another aspect, the invention provides a pharmaceutical composition comprising: (a) a modulator of iTR; and (b) a pharmaceutically acceptable carrier.

Certain conventional techniques of cell biology, cell culture, molecular biology, microbiology, recombinant nucleic acid (e.g., DNA) technology, immunology, etc., which are within the skill of the art, may be of use in aspects of the invention. Non-limiting descriptions of certain of these techniques are found in the following publications: Ausubel, F., et al., (eds.), Current Protocols in Molecular Biology, Current Protocols in Immunology, Current Protocols in Protein Science, and Current Protocols in Cell Biology, all John Wiley & Sons, N.Y., editions as of 2008; Sambrook, Russell, and Sambrook, Molecular Cloning: A Laboratory Manual, 3.sup.rd ed., Cold Spring Harbor Laboratory Press, Cold Spring Harbor, 2001; Harlow, E. and Lane, D., Antibodies—A Laboratory Manual, Cold Spring Harbor Laboratory Press, Cold Spring Harbor, 1988; Burns, R., Immunochemical Protocols (Methods in Molecular Biology) Humana Press; 3rd ed., 2005, Monoclonal antibodies: a practical approach (P. Shepherd and C Dean, eds., Oxford University Press, 2000); Freshney, R. L, "Culture of Animal Cells, A Manual of Basic Technique", 5th ed., John Wiley & Sons, Hoboken, NJ, 2005).

TR Modulation and iTR Modulators

The present invention provides iTR modulators and methods of use thereof. The invention further provides compositions and methods useful for identifying iTR modulators. In some aspects, the invention provides methods of enhancing regeneration comprising administering an agent that alters the concentration of said iTR modulators to a multicellular organism in need thereof.

Primitive animals that display the potential for profound TR such as the regeneration of amputated limbs in axolotis, or the regeneration of whole body segments in planaria do so by simply recapitulating normal embryonic development. The inability of said TR-resistant in mammals such as mice and humans is caused by alterations in certain embryonic gene transcription making them resistant to transition from fetal development back to an embryonic state. Provided herein are methods for the restoration of certain of these embryo-specific genes in TR-resistant animals thereby inducing competency for regeneration in any tissue, including responsiveness to organizing center factors, leading to complex tissue regeneration and a concomitant reduction in scar formation.

While certain genes have been found to be differentially-expressed in normal and regenerating tissue in these species, and some genes have been identified as being necessary to the regeneration of such a tissue, no genes have been reported to be, either in isolation or in combination with other genes, sufficient to reprogram the cells of an animal in the tissue of an animal otherwise incapable of TR (such as the tissue of a mammal) back to a state wherein the tissue can regenerate itself. There is therefore a need in the art for compositions and methods to identify genes that when expressed or alternatively repressed are sufficient to cause induced tissue regeneration (iTR) in mammalian cells and tissues, and compositions and methods to induce or repress such regeneration in the tissues of mammalian species in vivo, particularly in the species Homo sapiens.

Genes whose expression in fetal and adult animals inhibit TR are herein designated "TR inhibitors", and genes whose lack of expression in fetal and adult cells but whose expression in embryonic phases of development facilitate TR are herein designated "TR activators." Collectively, TR inhibitor genes and TR activator genes are herein designated iTR genes. Molecules that alter the levels of TR activators and TR inhibitors in a manner leading to TR are herein designated "iTR factors". iTR genes and, the protein products of iTR genes, are often conserved in animals ranging from sea anemones to mammals. iTR gene-encoded protein sequences, and sequences of nucleic acids (e.g., mRNA) encoding iTR genes, from a number of different animals are known in the art and can be found, e.g., in publicly available databases such as those available at the National Center for Biotechnology Information (NCBI).

The TR inhibitory gene COX7A1 was observed to be expressed primarily in stromal as opposed to epithelial cells in normal tissue. However, in the case of neoplasms the gene was observed to be down regulated in most stromal cancers such as osteosarcoma and chondrosarcoma. This is consistent with the observation of increased glycolysis in cancer known as the Warburg effect. Because TR genes are altered in the transition from embryonic to fetal development in part to prevent cancer in the adult, the repression of COX7A1 in stromal tumors would revert a stromal cell to an embryonic state which could facilitate oncogenesis. The exogenous expression of COX7A1 in stromal tumors would therefore have a therapeutic effect.

The invention provides a number of different methods of modulating iTR genes and a variety of different compounds useful for modulating iTR genes. In general, an iTR factor can be, e.g., a small molecule, nucleic acid, oligonucleotide, polypeptide, peptide, lipid, carbohydrate, etc. In some embodiments of the invention, iTR factors inhibit by decreasing the amount of TR inhibitor RNA produced by cells and/or by decreasing the level of activity of TR inhibitor genes. In the case of targeting TR inhibitors, factors are identified and used in research and therapy that reduce the levels of the product of the TR inhibitor gene. Said TR inhibitor gene can be any one or combination of TR inhibitor genes listed in FIG. 1A. The amount of IR inhibitor gene RNA can be decreased by inhibiting synthesis of TR inhibitor RNA synthesis by cells (also referred to as "inhibiting TR inhibitor gene expression"), e.g., by reducing the amount of mRNA encoding TR inhibitor genes or by reducing translation of mRNA encoding TR inhibitor genes. Said factor can be by way of nonlimiting example, RNAi targeting a sequence within the TR inhibitor genes listed in FIG. 1A.

In some embodiments of the invention, TR inhibitor gene expression is inhibited by RNA interference (RNAi). As known in the art, RNAi is a process in which the presence in a cell of double-stranded RNA that has sequence correspondence to a gene leads to sequence-specific inhibition of the expression of the gene, typically as a result of cleavage or translational repression of the mRNA transcribed from the gene. Compounds useful for causing inhibition of expression by RNAi ("RNAi agents") include short interfering RNAs (siRNAs), short hairpin RNAs (shRNAs), microRNAs (miRNAs), and miRNA-like molecules.

Exemplary sequences of siRNAs that inhibit human and marine TR inhibitor gene expression are provided in the Examples. One of skill in the art can readily design sequences for RNAi agents, e.g., siRNAs, useful for inhibiting expression of mammalian TR inhibitor genes, e.g., human TR inhibitor genes once one has identified said TR inhibitor genes. In some embodiments, such sequences are selected to minimize "off-target" effects. For example, a sequence that is complementary to a sequence present in TR inhibitor gene mRNA and not present in other mRNAs expressed in a species of interest (or not present in the genome of the species of interest) may be used. Position-specific chemical modifications may be used to reduce potential off-target effects. In some embodiments, at least two different RNAi agents, e.g., siRNAs, targeted to TR inhibitor gene snRNA are used in combination. In some embodiments, a microRNA (which may be an artificially designed microRNA) is used to inhibit TR inhibitor gene expression.

In some embodiments of the invention, TR inhibitor gene expression is inhibited using an antisense molecule comprising a single-stranded oligonucleotide that is perfectly or substantially complementary to mRNA encoding TR inhibitor genes. The oligonucleotide hybridizes to TR inhibitor gene mRNA leading, e.g., to degradation of the mRNA by RNase H or blocking of translation by steric hindrance. In other embodiments of the invention, TR inhibitor gene expression is inhibited using a ribozyme or triplex nucleic acid.

In some embodiments, of the invention, a TR inhibitor inhibits at least one activity of a TR inhibitor protein. TR inhibitor activity can be decreased by contacting the TR inhibitor protein with a compound that physically interacts with the TR inhibitor protein. Such a compound may, for example, alter the structure of the TR inhibitor protein (e.g., by covalently modifying it) and/or block the interaction of the TR inhibitor protein with one or more other molecule(s) such as cofactors or substrates. In some embodiments, inhibition or reduction may be a decrease of at least about 5%, 10%, 15%, 20%, 25%, 30%, 35%, 40%, 45%, 50%, 55%, 60%, 65%, 70%, 75%, 80%, 85%, 90%, 95%, or 99% of a reference level (e.g., a control level). A control level may be the level of the TR inhibitor that occurs in the absence of the factor. For example, an TR factor may reduce the level of the TR inhibitor protein to no more than 95%, 90%, 85%, 80%, 75%, 70%, 65%, 60%, 55%, 50%, 40%, 30%, 25%, 20%, 10%, or 5% of the level that occurs in the absence of the factor under the conditions tested. In some embodiments, levels of the TR inhibitor are reduced to 75% or less of the level that occurs in the absence of the factor, under the conditions tested. In some embodiments, levels of the TR inhibitor are reduced to 50% or less of the level that occurs in the absence of the TR factor, under the conditions tested. In some embodiments, levels of the TR inhibitor are reduced to 25% or less of the level that occurs in the absence of the iTR factor, under the conditions tested. In some embodiments, levels of the TR inhibitor are reduced to 10% or less of the level that occurs in the absence of the iTR factor, under the conditions tested. In some cases the level of modulation (e.g., inhibition or reduction) as compared with a control level is statistically significant. As used herein, "statistically significant" refers to a p-value of less than 0.05, e.g., a p-value of less than 0.025 or a p-value of less than 0.01, using an appropriate statistical test (e.g., ANOVA, t-test, etc.).

In some embodiments of the invention, a compound directly inhibits TR inhibitor proteins, i.e., the compound inhibits TR inhibitor proteins by a mechanism that involves a physical interaction (binding) between the TR inhibitor and the iTR factor. For example, binding of a TR inhibitor to an iTR factor can interfere with the TR inhibitor's ability to catalyze a reaction and/or can occlude the TR inhibitors active site. A variety of compounds can be used to directly inhibit TR inhibitors. Exemplary compounds that directly inhibit TR inhibitors can be, e.g., small molecules, antibodies, or aptamers.

In some embodiments of the invention, an iTR factor binds covalently to the TR inhibitor. For example, the compound may modify amino acid residue(s) that are needed for enzymatic activity. In some embodiments, an iTR factor comprises one or more reactive functional groups such as an aldehyde, haloalkane, alkene, fluorophosphonate (e.g., alkyl fluorophosphonate), Michael acceptor, phenyl sulfonate, methylketone, e.g., a halogenated methylketone or diazomethylketone, fluorophosphonate, vinyl ester, vinyl sulfone, or vinyl sulfonamide, that reacts with an amino acid side chain of TR inhibitors. In some embodiments, an iTR factor inhibitor comprises a compound that physically interacts with a TR inhibitor, wherein the compound comprises a reactive functional group. In some embodiments, the structure of a compound that physically interacts with the TR inhibitor is modified to incorporate a reactive functional group. In some embodiments, the compound comprises a TR inhibitor substrate analog or transition state analog. In some embodiments, the compound interacts with the TR inhibitor in or near the TR inhibitor active site.

In other embodiments, an iTR factor binds non-covalently to a TR inhibitor and/or to a complex containing the TR inhibitor and a TR inhibitor substrate. In some embodiments, an iTR factor binds non-covalently to the active site of a TR inhibitor and/or competes with substrate(s) for access to the TR inhibitor active site. In some embodiments, an iTR factor binds to the TR inhibitor with a $K_d$ of approximately $10^{-3}$ M or less, e.g., $10^{-4}$ M or less, e.g., $10^{-5}$ M or less, e.g., $10^{-6}$ M or less, $10^{-7}$ M or less, $10^{-8}$ M or less, or 1CT*M or less under the conditions tested, e.g., in a physiologically acceptable solution such as phosphate buffered saline. Binding affinity can be measured, e.g., using surface plasmon resonance (e.g., with a Biacore system), isothermal titration calorimetry, or a competitive binding assay, as known in the art. In some embodiments, the inhibitor comprises a TR inhibitor substrate analog or transition state analog.

In the case of increasing the activity of TR activators, any one of combination of the TR activator genes listed in FIG. 1B may be used. The levels of the products of these genes may be introduced using the vectors described herein.

Reporter-Based Screening Assays for TR Factors

The invention provides methods for identifying iTR factors using (a) a reporter molecule comprising a markers such as GFP whose expression is driven by one of the TR activator genes described herein such as COX7A1. The invention provides screening assays that involve determining whether a test compound affects the expression of TR activator genes and/or inhibits the expression of TR inhibitory genes. The invention further provides reporter molecules and compositions useful for practicing the methods. In general, compounds identified using the inventive methods can act by any of mechanism that results in increased or decreased TR activator or inhibitor genes respectively.

Reporter Molecules, Cells, and Membranes

In general, detectable moieties useful in the reporter molecules of the invention include light-emitting or light-absorbing compounds that generate or quench a detectable fluorescent, chemiluminescent, or bioluminescent signal. In some embodiments, activation of TR activator genes or inhibition of TR inhibitory genes causes release of the detectable moiety into a liquid medium, and the signal generated or quenched by the released detectable moiety present in the medium (or a sample thereof) is detected. In some embodiments, the resulting signal causes an alteration in a property of the detectable moiety, and such alteration can be detected, e.g., as an optical signal. For example, the signal may alter the emission or absorption of electromagnetic radiation (e.g., radiation having a wavelength within the infrared, visible or UV portion of the spectrum) by the detectable moiety. In some embodiments, a reporter molecule comprises a fluorescent or luminescent moiety, and a second molecule serves as quencher that quenches the fluorescent or luminescent moiety. Such alteration can be detected using apparatus and methods known in the art.

In some embodiments of the invention, the reporter molecule is a genetically encodable molecule that can be expressed by a cell, and the detectable moiety comprises, e.g., a detectable polypeptide. Thus in some embodiments, the reporter molecule is a polypeptide comprising a fluorescent polypeptides such as green, blue, sapphire, yellow, red, orange, and cyan fluorescent proteins and derivatives thereof (e.g., enhanced GFP); monomeric red fluorescent protein and derivatives such as those known as "mFruits", e.g., mCherry, mStrawberry, mTomato, etc., and luminescent proteins such as aequorin. (It will be understood that in some embodiments, the fluorescence or luminescence occurs in the presence of one or more additional molecules, e.g., an ion such as a calcium ion and/or a prosthetic group such as coelenterazine.) In some embodiments, the detectable moiety comprises an enzyme that acts on a substrate to produce a fluorescent, luminescent, colored, or otherwise detectable product. Examples of enzymes that may serve as detectable moieties include luciferase; beta.-galactosidase; horseradish peroxidase; alkaline phosphatase; etc. (It will be appreciated that the enzyme is detected by detecting the product of the reaction.) In some embodiments, the detectable moiety comprises a polypeptide tag that can be readily detected using a second agent such as a labeled (e.g., fluorescently labeled) antibody. For example, fluorescently labeled antibodies that bind to the HA, Myc, or a variety of other peptide tags are available. Thus the invention encompasses embodiments in which a detectable moiety can be detected directly (i.e., it generates a detectable signal without requiring interaction with a second agent) and embodiments in which a detectable moiety interacts (e.g., binds and/or reacts) with a second agent and such interaction renders the detectable moiety detectable, e.g., by resulting in generation of a detectable signal or because the second agent is directly detectable. In embodiments in which a detectable moiety interacts with a second agent to produce a detectable signal, the detectable moiety may react with the second agent is acted on by a second agent to produce a detectable signal. In many embodiments, the intensity of the signal provides an indication of the amount of detectable moiety present, e.g., in a sample being assessed or in area being imaged. In some embodiments, the amount of detectable moiety is optionally quantified, e.g., on a relative or absolute basis, based on the signal intensity.

The invention provides nucleic acids comprising a sequence that encodes a reporter polypeptide of the invention. In some embodiments, a nucleic acid encodes a precursor polypeptide of a reporter polypeptide of the invention. In some embodiments, the sequence encoding the polypeptide is operably linked to expression control elements (e.g., a promoter or promoter/enhancer sequence) appropriate to direct transcription of mRNA encoding the polypeptide. The invention further provides expression vectors comprising the nucleic acids. Selection of appropriate expression control elements may be based, e.g., on the cell type and species in which the nucleic acid is to be expressed. One of ordinary skill in the art can readily select appropriate expression control elements and/or expression vectors. In some embodiments, expression control element(s) are regulatable, e.g., inducible or repressible. Exemplary promoters suitable for use in bacterial cells include, e.g., Lac, Trp, Tac, araBAD (e.g., in a pBAD vectors), phage promoters such as T7 or T3. Exemplary expression control sequences useful for directing expression in mammalian cells include, e.g., the early and late promoters of SV40, adenovirus or cytomegalovirus immediate early promoter, or viral promoter/enhancer sequences, retroviral LTRs, promoters or promoter/enhancers from mammalian genes, e.g., actin, EF-1 alpha, phosphoglycerate kinase, etc. Regulatable (e.g., inducible or repressible) expression systems such as the Tet-On and Tet-Off systems (regulatable by tetracycline and analogs such as doxycycline) and others that can be regulated by small molecules such as hormones receptor ligands (e.g., steroid receptor ligands, which may or may not be steroids), metal-regulated systems (e.g., metallothionein promoter), etc.

The invention further provides cells and cell lines that comprise such nucleic acids and/or vectors. In some embodiments, the cells are eukaryotic cells, e.g., fungal, plant, or animal cells. In some embodiments, the cell is a vertebrate cell, e.g., a mammalian cell, e.g., a human cell, non-human primate cell, or rodent cell. The cell may be any cell described infra. In certain embodiments the cell may be a clonal cell or an oligoclonal cell. In some embodiments the cell may be a progenitor cell that has been obtained from a pluripotent stem cell, such as an ES cell or an iPS cell. In some embodiments a cell is a member of a cell line, e.g., an established or immortalized cell line that has acquired the ability to proliferate indefinitely in culture (e.g., as a result of mutation or genetic manipulation such as the constitutive expression of the catalytic component of telomerase). Numerous cell lines are known in the art and can be used in the instant invention. Mammalian cell lines include, e.g., HEK-293 (e.g., HEK-293T), CHO, NIH-3T3, COS, and HeLa cell lines. In some embodiments, a cell line is a tumor cell line. In other embodiments, a cell is non-tumorigenic and/or is not derived from a tumor. In some embodiments, the cells are adherent cells. In some embodiments, non-adherent cells are used. In some embodiments, a cell is of a cell type or cell line is used that has been shown to naturally have a subset of TR activator genes expressed or TR inhibitor genes not expressed. If a cell lacks one or more TR activator or inhibitor genes, the cell can be genetically engineered to express such protein(s). In some embodiments, a cell line of the invention is descended from a single cell. For example, a population of cells can be transfected with a nucleic acid encoding the reporter polypeptide and a colony derived from a single cell can be selected and expanded in culture. In some embodiments, cells are transiently transfected with an expression vector that encodes the reporter molecule. Cells can be co-transfected with a control plasmid, optionally expressing a different detectable polypeptide, to control for transfection efficiency (e.g., across multiple runs of an assay).

TR Activator and TR Inhibitor Polypeptides and Nucleic Adds

TR activator and TR inhibitor genes are listed in FIG. 1. TR activator and TR inhibitor polypeptides useful in the inventive methods may be obtained by a variety of methods. In some embodiments, the polypeptides are produced using recombinant DNA techniques. Standard methods for recombinant protein expression can be used. A nucleic acid encoding a TR activator or TR inhibitor gene can readily be obtained, e.g., from cells that express the genes (e.g., by PCR or other amplification methods or by cloning) or by chemical synthesis or in vitro transcription based on the cDNA sequence polypeptide sequence. One of ordinary skill in the art would know that due to the degeneracy of the genetic code, the genes can be encoded by many different nucleic acid sequences. Optionally, a sequence is codon-optimized for expression in a host cell of choice. The genes could be expressed in bacterial, fungal, animal, or plant cells or organisms. The genes could be isolated from cells that naturally express it or from cells into which a nucleic acid encoding the protein has been transiently or stably introduced, e.g., cells that contain an expression vector encoding the genes. In some embodiments, the gene is secreted by cells in culture and isolated from the culture medium.

In some embodiments of the invention, the sequence of a TR activator or TR inhibitor polypeptide is used in the inventive screening methods. A naturally occurring TR activator or TR inhibitor polypeptide can be from any species whose genome encodes a TR activator or TR inhibitor polypeptide, e.g., human, non-human primate, rodent, etc. A polypeptide whose sequence is identical to naturally occurring TR activator or TR inhibitor is sometimes referred to herein as "native TR activator/inhibitor". A TR activator or TR inhibitor polypeptide of use in the invention may or may not comprise a secretion signal sequence or a portion thereof. For example, mature TR activator or TR inhibitor comprising or consisting of amino acids 20-496 of human TR activator or TR inhibitor (or corresponding amino acids of TR activator or TR inhibitor of a different species) may be used.

In some embodiments, a polypeptide comprising or consisting of a variant or fragment of TR activator or TR inhibitor is used. TR activator or TR inhibitor variants include polypeptides that differ by one or more amino acid substitutions, additions, or deletions, relative to TR activator or TR inhibitor. In some embodiments, a TR activator or TR inhibitor variant comprises a polypeptide at least 70%, 75%, 80%, 85%, 90%, 95%, 96%, 97%, 98%, 99%, or more identical to at least amino acids 20-496 of TR activator or TR inhibitor (e.g., from human or mouse) over at least 50%, 60%, 70%, 80%, 85%, 90%, 95%, 96%, 97%, 98%, 99%, or 100% of at least amino acids 20-496 of human TR activator or TR inhibitor or amino acids 20-503 of mouse TR activator or TR inhibitor. In some embodiments, a TR activator or TR inhibitor variant comprises a polypeptide at least 80%, 85%, 90%, 95%, 96%, 97%, 98%, 99%, or more identical to at least amino acids 20-496 of human TR activator or TR inhibitor or amino acids 20-503 of mouse TR activator or TR inhibitor. In some embodiments, a TR activator or TR inhibitor polypeptide comprises a polypeptide at least 80%, 85%, 90%, 95%, 96%, 97%, 98%, 99%, or more identical to at least amino acids 20-496 of human TR activator or TR inhibitor or amino acids 20503 of mouse TR activator or TR inhibitor. A nucleic acid that encodes a TR activator or TR inhibitor variant or fragment can readily be generated, e.g., by modifying the DNA that encodes native TR activator or TR inhibitor using, e.g., site-directed mutagenesis, or by other standard methods, and used to produce the TR activator or TR inhibitor variant or fragment. For example, a fusion protein can be produced by cloning sequences that encode TR activator or TR inhibitor into a vector that provides the sequence encoding the heterologous portion. In some embodiments a tagged TR activator or TR inhibitor is used. For example, in some embodiments a TR activator or TR inhibitor polypeptide comprising a 6× His tag, e.g., at its C terminus, is used.

Test Compounds

A wide variety of test compounds can be used in the inventive methods for identifying iTR factors. For example, a test compound can be a small molecule, polypeptide, peptide, nucleic acid, oligonucleotide, lipid, carbohydrate, antibody, or hybrid molecule. Compounds can be obtained from natural sources or produced synthetically. Compounds can be at least partially pure or may be present in extracts or other types of mixtures whose components are at least in part unknown or uncharacterized. Extracts or fractions thereof can be produced from, e.g., plants, animals, microorganisms, marine organisms, fermentation broths (e.g., soil, bacterial or fungal fermentation broths), etc. In some embodiments, a compound collection ("library") is tested. The library may comprise, e.g., between 100 and 500,000 compounds, or more. Compounds are often arrayed in multiwell plates (e.g., 384 well plates, 1596 well plates, etc.). They can be dissolved in a solvent (e.g., DMSO) or provided in dry form, e.g., as a powder or solid. Collections of synthetic, semi-synthetic, and/or naturally occurring compounds can be tested. Compound libraries can comprise structurally related, structurally diverse, or structurally unrelated compounds. Compounds may be artificial (having a structure invented by man and not found in nature) or naturally occurring. In some embodiments, a library comprises at least some compounds that have been identified as "hits" or "leads" in other drug discovery programs and/or derivatives thereof. A compound library can comprise natural products and/or compounds generated using non-directed or directed synthetic organic chemistry. Often a compound library is a small molecule library. Other libraries of interest include peptide or peptoid libraries, cDNA libraries, antibody libraries, and oligonucleotide libraries. A library can be focused (e.g., composed primarily of compounds having the same core structure, derived from the same precursor, or having at least one biochemical activity in common).

Compound libraries are available from a number of commercial vendors such as Tocris Bioscience, Nanosyn, BioFocus, and from government entities. For example, the Molecular Libraries Small Molecule Repository (MLSMR), a component of the U.S. National Institutes of Health (NIH) Molecular Libraries Program is designed to identify, acquire, maintain, and distribute a collection of >300,000 chemically diverse compounds with known and unknown biological activities for use, e.g., in high-throughput screening (HTS) assays. The NIH Clinical Collection (NCC) is a plated array of approximately 450 small molecules that have a history of use in human clinical trials. These compounds are drug-like with known safety profiles. In some embodiments, a collection of compounds comprising "approved human drugs" is tested. An "approved human drug" is a compound that has been approved for use in treating humans by a government regulatory agency such as the US Food and Drug Administration, European Medicines Evaluation Agency, or a similar agency responsible for evaluating at least the safety of therapeutic agents prior to allowing them to be marketed. The test compound may be, e.g., an antineoplastic, antibacterial, antiviral, antifungal, antiprotozoal, antiparasitic, antidepressant, antipsychotic, anesthetic, antianginal, antihypertensive, antiarrhythmic, anti-inflammatory, analgesic, antithrombotic, antiemetic, immunomodulator, antidiabetic, lipid- or cholesterol-lowering (e.g., statin), anticonvulsant, anticoagulant, antianxiety, hypnotic (sleep-inducing), hormonal, or anti-hormonal drug, etc. In some embodiments, a compound is one that has undergone at least some preclinical or clinical development or has been determined or predicted to have "drug-like" properties. For example, the test compound may have completed a Phase I trial or at least a preclinical study in non-human animals and shown evidence of safety and tolerability.

In some embodiments, a test compound is substantially non-toxic to cells of an organism to which the compound may be administered and/or to cells with which the compound may be tested, at the concentration to be used or, in some embodiments, at concentrations up to 10-fold, 100-fold, or 1,000-fold higher than the concentration to be used. For example, there may be no statistically significant effect on cell viability and/or proliferation, or the reduction in viability or proliferation can be no more than 1%, 5%, or 10% in various embodiments. Cytotoxicity and/or effect on cell proliferation can be assessed using any of a variety of assays. For example, a cellular metabolism assay such as AlamarBlue, MTT, MTS, STT, and CellTitre Glo assays, a cell membrane integrity assay, a cellular ATP-based viability assay, a mitochondrial reductase activity assay, a BrdU, EdU, or H3-Thymidine incorporation assay could be used. In some embodiments, a test compound is not a compound that is found in a cell culture medium known or used in the art, e.g., culture medium suitable for culturing vertebrate, e.g., mammalian cells or, if the test compound is a compound that is found in a cell culture medium known or used in the art, the test compound is used at a different, e.g., higher, concentration when used in a method of the present invention.

Aspects of Assay Implementation and Controls

Various inventive screening assays described above involve determining whether a test compound inhibits the levels of active TR inhibitors or increases the levels of active TR activators. Suitable cells for expression of a reporter molecule are described above.

In performing an inventive assay, assay components (e.g., cells, TR activator or TR inhibitor polypeptide, and test compounds) are typically dispensed into multiple vessels or other containers. Any type of vessel or article capable of containing cells can be used. In many embodiments of the invention, the vessels are wells of a multi-well plate (also called a "microwell plate", "microtiter plate", etc. For purposes of description, the term "well" will be used to refer to any type of vessel or article that can be used to perform an inventive screen, e.g., any vessel or article that can contain the assay components. It should be understood that the invention is not limited to use of wells or to use of multi-well plates. In some embodiments, any article of manufacture in which multiple physically separated cavities (or other confining features) are present in or on a substrate can be used. For example, assay components can be confined in fluid droplets, which may optionally be arrayed on a surface and, optionally, separated by a water-resistant substance that confines the droplets to discrete locations, in channels of a microfluidic device, etc.

In general, assay components can be added to wells in any order. For example, cells can be added first and maintained in culture for a selected time period (e.g., between 6 and 48 hours) prior to addition of a test compound and target TR activator or TR inhibitor polypeptides or cells with express constructs to a well. In some embodiments, compounds are added to wells prior to addition of polypeptides of cells. In some embodiments, expression of a reporter polypeptide is induced after plating the cells, optionally after addition of a test compound to a well. In some embodiments, expression of the reporter molecule is achieved by transfecting the cells with an expression vector that encodes the reporter polypeptide. In some embodiments, the cells have previously been genetically engineered to express the reporter polypeptide. In some embodiments, expression of the reporter molecule is under control of regulatable expression control elements, and induction of expression of the reporter molecule is achieved by contacting the cells with an agent that induces (or derepresses) expression.

The assay composition comprising cells, test compound, or polypeptide is maintained for a suitable time period during which test compound may (in the absence of a test compound that inhibits its activity) cause an increase or decrease of the level or activity of the target TR activator or TR inhibitor. The number of cells, amount of TR activator or TR inhibitor polypeptide, and amount of test compound to be added will depend, e.g., on factors such as the size of the vessel, cell type, and can be determined by one of ordinary skill in the art. In some embodiments, the ratio of the molar concentration of TR activator or TR inhibitor polypeptide to test compound is between 1:10 and 10:1. In some embodiments, the number of cells, amount of test compound, and length of time for which the composition is maintained can be selected so that a readily detectable level signal after a selected time period in the absence of a test compound. In some embodiments, cells are at a confluence of about 25%-75%, e.g., about 50%, at the time of addition of compounds. In some embodiments, between 1,000 and 10,000 cells/well (e.g., about 5,000 cells/well) are plated in about 100 pi medium per well in 96-well plates. In other exemplary embodiments, cells are seeded in about 30 pl-50 pi of medium at between 500 and 2,000 (e.g., about 1000) cells per well into 384-well plates. In some embodiments, compounds are tested at multiple concentrations (e.g., 2-10 different concentrations) and/or in multiple replicates (e.g., 2-10 replicates). Multiple replicates of some or all different concentrations can be performed. In some embodiments, candidate TR factors are used at a concentration between 0.1 μg/ml and 100 μg/ml, e.g., 1 μg/ml and 10 μg/ml. In some embodiments, candidate TR factors are used at multiple concentrations. In some embodiments, compounds are added to cells between 6 hours and one day (24 hr) after seeding.

In some aspects of any of the inventive compound screening and/or characterization methods, a test compound is added to an assay composition in an amount sufficient to achieve a predetermined concentration. In some embodiments the concentration is up to about 1 nM. In some embodiments the concentration is between about 1 nM and about 100 nM. In some embodiments the concentration is between about 100 nM and about 10 μM. In some embodiments the concentration is at least 10 μM, e.g., between 10 μM and 100 μM. The assay composition can be maintained for various periods of time following addition of the last component thereof. In certain embodiments the assay composition is maintained for between about 10 minutes and about 4 days, e.g., between 1 hour and 3 days, e.g., between 2 hours and 2 days, or any intervening range or particular value, e.g., about 4-8 hours, after addition of all components. Multiple different time points can be tested. Additional aliquots of test compound can be added to the assay composition within such time period. In some embodiments, cells are maintained in cell culture medium appropriate for culturing cells of that type. In some embodiments, a serum-free medium is used. In some embodiments, the assay composition comprises a physiologically acceptable liquid that is compatible with maintaining integrity of the cell membrane and, optionally, cell viability, instead of cell culture medium. Any suitable liquid could be used provided it has the proper osmolarity and is otherwise compatible with maintaining reasonable integrity of the cell membrane and, optionally, cell viability, for at least a sufficient period of time to perform an assay. One or more measurements indicative of an increase in the level of active TR activator or decrease in TR inhibitor can be made during or following the incubation period.

In some embodiments, individual compounds, each typically of known identity (e.g., structure and/or sequence), are added to each of a multiplicity of wells. In some embodiments, two or more compounds may be added to one or more wells. In some embodiments, one or more compounds of unknown identity may be tested. The identity may be determined subsequently using methods known in the art.

In various embodiments, foregoing assay methods of the invention are amenable to high-throughput screening (HTS) implementations. In some embodiments, the screening assays of the invention are high throughput or ultra high throughput (see, e.g., Fernandes, P. B., Curr Opin Chem. Biol. 1998, 2:597; Sundberg, S A, Curr Opin Biotechnol. 2000, 11:47). High throughput screens often involve testing large numbers of compounds with high efficiency, e.g., in parallel. For example, tens or hundreds of thousands of compounds can be routinely screened in short periods of time, e.g., hours to days. In some embodiments, HTS refers to testing of between 1,000 and 100,000 compounds per day. In some embodiments, ultrahigh throughput refers to screening in excess of 100,000 compounds per day, e.g., up to 1 million or more compounds per day. The screening assays of the invention may be carried out in a multi-well format, for example, a 96-well, 384-well format, 1,536-well format, or 3,456-well format and are suitable for automation. In some embodiments, each well of a microwell plate can be used to run a separate assay against a different test compound, or, if concentration or incubation time effects are to be observed, a plurality of wells can contain test samples of a single compound, with at least some wells optionally being left empty or used as controls or replicates. Typically, HTS implementations of the assays disclosed herein involve the use of automation. In some embodiments, an integrated robot system including one or more robots transports assay microwell plates between multiple assay stations for compound, cell and/or reagent addition, mixing, incubation, and readout or detection. In some aspects, an HTS system of the invention may prepare, incubate, and analyze many plates simultaneously. Suitable data processing and control software may be employed. High throughput screening implementations are well known in the art. Without limiting the invention in any way, certain general principles and techniques that may be applied in embodiments of a HTS of the present invention are described in Macarron R & Hertzberg R P. Design and implementation of high-throughput screening assays. *Methods Mol Biol.*, 565:1-32, 2009 and/or An W F & Tolliday N J., Introduction: cell-based assays for high-throughput screening. *Methods Mol Biol.* 486:1-12, 2009, and/or references in either of these. Exemplary methods are also disclosed in High Throughput Screening: Methods and Protocols (Methods in Molecular Biology) by William P. Janzen (2002) and High-Throughput Screening in Drug Discovery (Methods and Principles in Medicinal Chemistry) (2006).

An additional compound may, for example, have one or more improved pharmacokinetic and/or pharmacodynamic properties as compared with an initial hit or may simply have a different structure. An "improved property" may, for example, render a compound more effective or more suitable for one or more purposes described herein. In some embodiments, for example, a compound may have higher affinity for the molecular target of interest (e.g., TR activator or TR inhibitor gene products), lower affinity for a non-target molecule, greater solubility (e.g., increased aqueous solubility), increased stability (e.g., in blood, plasma, and/or in the gastrointestinal tract), increased half-life in the body, increased bioavailability, and/or reduced side effect(s), etc. Optimization can be accomplished through empirical modification of the hit structure (e.g., synthesizing compounds with related structures and testing them in cell-free or cell-based assays or in non-human animals) and/or using computational approaches. Such modification can in some embodiments make use of established principles of medicinal chemistry to predictably alter one or more properties. In some embodiments, one or more compounds that are "hit" are identified and subjected to systematic structural alteration to create a second library of compounds (e.g., refined lead compounds) structurally related to the hit. The second library can then be screened using any of the methods described herein.

In some embodiments, an iTR factor is modified or incorporates a moiety that enhances stability (e.g., in serum), increases half-life, reduces toxicity or immunogenicity, or otherwise confers a desirable property on the compound.

Uses of iTR Factors
Pharmaceutical Compositions iTR factors have a variety of different uses. Non-limiting examples of such uses are discussed herein. In some embodiments, an iTR factor is used to enhance regeneration of an organ or tissue. Exemplary organs and tissues suitable for enhanced regeneration include limb, digit, cartilage, heart, blood vessel, bone, esophagus, stomach, liver, gallbladder, pancreas, intestines, rectum, anus, endocrine gland (e.g., thyroid, parathyroid, adrenal, endocrine portion of pancreas), skin, hair follicle, thymus, spleen, skeletal muscle, focal damaged cardiac muscle, smooth muscle, brain, spinal cord, peripheral nerve, ovary, fallopian tube, uterus, vagina, mammary gland, testes, vas deferens, seminal vesicle, prostate, penis, pharynx, larynx, trachea, bronchi, lungs, kidney, ureter, bladder, urethra, eye (e.g., retina, cornea), or ear (e.g., organ of *Corti*). In some embodiments, an iTR factor is used to enhance regeneration of a stromal layer, e.g., a connective tissue supporting the parenchyma of a tissue. In some embodiments, an iTR factor is used to enhance regeneration following surgery, e.g., surgery that entails removal of at least a portion of a diseased or damaged tissue, organ, or other structure such as a limb, digit, etc. For example, such surgery might remove at least a portion of a liver, lung, kidney, stomach, pancreas, intestine, mammary gland, ovary, testis, bone, limb, digit, muscle, skin, etc. In some embodiments, the surgery is to remove a tumor. In some embodiments, an iTR factor is used to promote scarless regeneration of skin following trauma, surgery, disease, and burns.

Enhancing regeneration can include any one or more of the following, in various embodiments: (a) increasing the rate of regeneration; (b) increasing the extent of regeneration; (c) promoting establishment of appropriate structure (e.g., shape, pattern, tissue architecture, tissue polarity) in a regenerating tissue or organ or other body structure; (d) promoting growth of new tissue in a manner that retains and/or restores function. While use of an iTR factor to enhance regeneration is of particular interest, the invention encompasses use of an iTR factor to enhance repair or wound healing in general, without necessarily producing a detectable enhancement of regeneration. Thus, the invention provides methods of enhancing repair or wound healing, wherein an iTR factor is administered to a subject in need thereof according to any of the methods described herein. In some embodiments aniTR factor is used to heal a wound or enhance the natural wound healing ability of a subject. For example the iTR factor could be used to heal a wound faster or could be used to heal a wound without forming a scar.

In some embodiments, the invention provides a method of enhancing regeneration in a subject in need thereof, the method comprising administering an effective amount of an iTR factor to the subject. In some embodiments, an effective amount of a compound (e.g., an iTR factor) is an amount that results in an increased rate or extent of regeneration of damaged tissue as compared with a reference value (e.g., a suitable control value). In some embodiments, the reference value is the expected (e.g., average or typical) rate or extent of regeneration in the absence of the compound (optionally with administration of a placebo). In some embodiments, an effective amount of an iTR factor is an amount that results in an improved structural and/or functional outcome as compared with the expected (e.g., average or typical) structural or functional outcome in the absence of the compound. In some embodiments, an effective amount of a compound, e.g., an iTR factor, results in enhanced blastema formation and/or reduced scarring. Extent or rate of regeneration can be assessed based on dimension(s) or volume of regenerated tissue, for example. Structural and/or functional outcome can be assessed based on, e.g., visual examination (optionally including use of microscopy or imaging techniques such as X-rays, CT scans, MRI scans, PET scans) and/or by evaluating the ability of the tissue, organ, or other body part to perform one or more physiological processes or task(s) normally performed by such tissue, organ, or body part. Typically, an improved structural outcome is one that more closely resembles normal structure (e.g., structure that existed prior to tissue damage or structure as it exists in a normal, healthy individual) as compared with the structural outcome that would be expected (e.g., average or typical outcome) in the absence of treatment with an iTR factor. One of ordinary skill in the art can select an appropriate assay or test for function. In some embodiments, an increase in the rate or extent of regeneration as compared with a control value is statistically significant (e.g., with a p value of <0.05, or with a p value of <0.01) and/or clinically significant. In some embodiments, an improvement in structural and/or functional outcome as compared with a control value is statistically significant and/or clinically significant.

"Clinically significant improvement" refers to an improvement that, within the sound judgment of a medical or surgical practitioner, confers a meaningful benefit on a subject (e.g., a benefit sufficient to make the treatment worthwhile). It will be appreciated that in many embodiments an iTR modulator, e.g., an iTR factor, administered to a subject of a particular species (e.g., for therapeutic purposes) is a compound that modulates, e.g., inhibits, the endogenous TR genes expressed in subjects of that species. For example, if a subject is human, a compound that inhibits the activity of human TR inhibitor gene products and activates the activity of human TR activator gene products would typically be administered.

In some embodiments, the iTR factor is used to enhance skin regeneration, e.g., after a burn (thermal or chemical), scrape injury, or other situations involving skin loss, e.g., infections such as necrotizing fasciitis or purpura fulminans. In some embodiments, a burn is a second or third degree burn. In some embodiments a region of skin loss has an area of at least 10 $cm^2$. In one aspect, an iTR factor enhances regeneration of grafted skin. In one aspect, an iTR factor reduces excessive and/or pathological wound contraction or scarring.

In some embodiments, an iTR factor is used to enhance bone regeneration, e.g., in a situation such as non-union fracture, implant fixation, periodontal or alveolar ridge augmentation, craniofacial surgery, or other conditions in which generation of new bone is considered appropriate. In some embodiments, an iTR factor is applied to a site where bone regeneration is desired. In some embodiments, an iTR factor is incorporated into or used in combination with a bone graft material. Bone graft materials include a variety of ceramic and proteinaceous materials. Bone graft materials include autologous bone (e.g., bone harvested from the iliac crest, fibula, ribs, etc.), allogeneic bone from cadavers, and xenogeneic bone. Synthetic bone graft materials include a variety of ceramics such as calcium phosphates (e.g. hydroxyapatite and tricalcium phosphate), bioglass, and calcium sulphate, and proteinaceous materials such as demineralized bone matrix (DBM). DBM can be prepared by grinding cortical bone tissues (generally to 100-500 pm sieved particle size), then treating the ground tissues with hydrochloric acid (generally 0.5 to 1 N). In some embodiments, an iTR factor is administered to a subject together with one or more bone graft materials. The iTR factor may be combined with the bone graft material (in a composition comprising an iTR factor and a bone graft material) or administered separately, e.g., after placement of the graft. In some embodiments, the invention provides a bone paste comprising an iTR factor. Bone pastes are products that have a suitable consistency and composition such that they can be introduced into bone defects, such as voids, gaps, cavities, cracks etc., and used to patch or fill such defects, or applied to existing bony structures. Bone pastes typically have sufficient malleability to permit them to be manipulated and molded by the user into various shapes. The desired outcome of such treatments is that bone formation will occur to replace the paste, e.g., retaining the shape in which the paste was applied. The bone paste provides a supporting structure for new bone formation and may contain substance(s) that promote bone formation. Bone pastes often contain one or more components that impart a paste or putty-like consistency to the material, e.g., hyaluronic acid, chitosan, starch components such as amylopectin, in addition to one or more of the ceramic or proteinaceous bone graft materials (e.g., DBM, hydroxyapatite) mentioned above.

In some embodiments, an iTR factor enhances the formation and/or recruitment of osteoprogenitor cells from undifferentiated mesechymal cells and/or enhances the differentiation of osteoprogenitor cells into cells that form new bone (osteoblasts).

In some embodiments, an iTR factor is administered to a subject with osteopenia or osteoporosis, e.g., to enhance bone regeneration in the subject.

In some embodiments, an iTR factor is used to enhance regeneration of a joint (e.g., a fibrous, cartilaginous, or synovial joint). In some embodiments, the joint is an intervertebral disc. In some embodiments, a joint is a hip, knee, elbow, or shoulder joint. In some embodiments, an iTR factor is used to enhance regeneration of dental and/or periodontal tissues or structures (e.g., pulp, periodontal ligament, teeth, periodontal bone).

In some embodiments, an iTR factor is administered to a subject in combination with cells. The iTR factor and the cells may be administered separately or in the same composition. If administered separately, they may be administered at the same or different locations. The cells can be autologous, allogeneic, or xenogeneic in various embodiments. The cells can comprise progenitor cells or stem cells, e.g., adult stem cells. As used herein, a stem cell is a cell that possesses at least the following properties: (i) self-renewal, i.e., the ability to go through numerous cycles of cell division while still maintaining an undifferentiated state; and (ii) multipotency or multidifferentiative potential, i.e., the ability to generate progeny of several distinct cell types (e.g., many, most, or all of the distinct cell types of a particular tissue or organ). An adult stem cell is a stein cell originating from non-embryonic tissues (e.g., fetal, post-natal, or adult tissues). As used herein, the term "progenitor cell" encompasses cells that are multipotent and cells that are more differentiated than pluripotent stem cells but not fully differentiated. Such more differentiated cells (which may arise from embryonic progenitor cells) have reduced capacity for self-renewal as compared with embryonic progenitor cells. In some embodiments, an iTR factor is administered in combination with mesenchymal progenitor cells, neural progenitor cells, endothelial progenitor cells, hair follicle progenitor cells, neural crest progenitor cells, mammary stem cells, lung progenitor cells (e.g., bronchioalveolar stem cells), muscle progenitor cells (e.g., satellite cells), adipose-derived progenitor cells, epithelial progenitor cells (e.g., keratinocyte stein cells), and/or hematopoietic progenitor cells (e.g., hematopoietic stem cells). In some embodiments, the cells comprise induced pluripotent stem cells (iPS cells), or cells that have been at least partly differentiated from iPS cells. In some embodiments, the progenitor cells comprise adult stem cells. In some embodiments, at least some of the cells are differentiated cells, e.g., chondrocytes, osteoblasts, keratinocytes, hepatocytes. In some embodiments, the cells comprise myoblasts.

In some embodiments, an factor is administered in a composition (e.g., a solution) comprising one or more compounds that polymerizes or becomes cross-linked or undergoes a phase transition in situ following administration to a subject, typically forming a hydrogel. The composition may comprise monomers, polymers, initiating agents, cross-linking agents, etc. The composition may be applied (e.g., using a syringe) to an area where regeneration is needed, where it forms a gel in situ, from which an iTR factor is released over time. Gelation may be triggered, e.g., by contact with ions in body fluids or by change in temperature or pH, or by light, or by combining reactive precursors (e.g., using a multi-barreled syringe). See, e.g., U.S. Pat. No. 6,129,761; Yu L, Ding J. Injectable hydrogels as unique biomedical materials. Chem Soc Rev. 37(8): 1473-81 (2008)). In some embodiments the hydrogel is a hyaluronic acid or hyaluronic acid and collagen I-containing hydrogel such as HyStem-C described herein. In some embodiments, the composition further comprises cells.

In some embodiments, an iTR factor is administered to a subject in combination with vectors expressing the catalytic component of telomerase. The vector may be administered separately or in the same composition. If administered separately, they may be administered at the same or different locations. The vector may express the telomerase catalytic component from the same species as the treated tissue or from another species. Said co-administration of the iTR factor with the telomerase catalytic component is particularly useful wherein the target tissue is from an aged subject and the subject is human.

Other inventive methods comprise use of an iTR factor in the ex vivo production of living, functional tissues, organs, or cell-containing compositions to repair or replace a tissue or organ lost due to damage. For example, cells or tissues removed from an individual (either the future recipient, an individual of the same species, or an individual of a different species) may be cultured in vitro, optionally with an matrix, scaffold (e.g., a three dimensional scaffold) or mold (e.g., comprising a biocompatible, optionally biodegradable, material, e.g., a polymer such as HyStem-C), and their development into a functional tissue or organ can be promoted by contacting an iTR factor. The scaffold, matrix, or mold may be composed at least in part of naturally occurring proteins such as collagen, hyaluronic acid, or alginate (or chemically modified derivatives of any of these), or synthetic polymers or copolymers of lactic acid, caprolactone, glycolic acid, etc., or self-assembling peptides, or decellularized matrices derived from tissues such as heart valves, intestinal mucosa, blood vessels, and trachea. In some embodiments, the scaffold comprises a hydrogel. The scaffold may, in certain embodiments, be coated or impregnated with an iTR factor, which may diffuse out from the scaffold over time. After production ex vivo, the tissue or organ is grafted into or onto a subject. For example, the tissue or organ can be implanted or, in the case of certain tissues such as skin, placed on a body surface. The tissue or organ may continue to develop in vivo. In some embodiments, the tissue or organ to be produced at least in part ex vivo may be a bladder, blood vessel, bone, fascia, liver, muscle, skin patch, etc. Suitable scaffolds may, for example, mimic the extracellular matrix (ECM). Optionally an iTR factor is administered to the subject prior to, during, and/or following grafting of the ex vivo generated tissue or organ. In some aspects, a biocompatible material is a material that is substantially non-toxic to cells in vitro at the concentration used or, in the case of a material that is administered to a living subject, is substantially nontoxic to the subject's cells in the quantities and at the location used and does not elicit or cause a significant deleterious or untoward effect on the subject, e.g., an immunological or inflammatory reaction, unacceptable scar tissue formation, etc. It will be understood that certain biocompatible materials may elicit such adverse reactions in a small percentage of subjects, typically less than about 5%, 1%, 0.5%, or 0.1%.

In some embodiments, a matrix or scaffold coated or impregnated with an iTR factor is implanted, optionally in combination with cells, into a subject in need of regeneration. The matrix or scaffold may be in the shape of a tissue or organ whose regeneration is desired. The cells may be any cell described infra, e.g., stem cells of one or more type(s) that gives rise to such tissue or organ and/or of type(s) found in such tissue or organ.

In some embodiments, an iTR factor is administered directly to or near a site of tissue damage. "Directly to a site of tissue damage" encompasses injecting a compound or composition into a site of tissue damage or spreading, pouring, or otherwise directly contacting the site of tissue damage with the compound or composition. In some embodiments, administration is considered "near a site of tissue damage" if administration occurs within up to about 10 cm away from a visible or otherwise evident edge of a site of tissue damage or to a blood vessel (e.g., an artery) that is located at least in part within the damaged tissue or organ. Administration "near a site of tissue damage" is sometimes administration within a damaged organ, but at a location where damage is not evident. In some embodiments, following damage or loss of a tissue, organ, or other structure, an iTR factor is applied to the remaining portion of the tissue, organ, or other structure. In some embodiments, an iTR factor is applied to the end of a severed digit or limb) that remains attached to the body, to enhance regeneration of the portion that has been lost. In some embodiments, the severed portion is reattached surgically, and an iTR factor is applied to either or both faces of the wound. In some embodiments, an iTR factor is administered to enhance engraftment or healing or regeneration of a transplanted organ or portion thereof. In some embodiments, an iTR factor is used to enhance nerve regeneration. For example, an iTR factor may be infused into a severed nerve, e.g., near the proximal and/or distal stump. In some embodiments, an iTR factor is placed within an artificial nerve conduit, a tube composed of biological or synthetic materials within which the nerve ends and intervening gap are enclosed.

In some embodiments, an iTR factor is used to promote production of hair follicles and/or growth of hair. In some embodiments an iTR factor triggers regeneration of hair follicles from epithelial cells that do not normally form hair. In some embodiments, an iTR factor is used to treat hair loss, hair sparseness, and partial or complete baldness in a male or female. In some embodiments, baldness is the state of having no or essentially no hair or lacking hair where it often grows, such as on the top, back, and/or sides of the head. In some embodiments, hair sparseness is the state of having less hair than normal or average or, in some embodiments, less hair than an individual had in the past or, in some embodiments, less hair than an individual considers desirable. In some embodiments, an iTR factor is used to promote growth of eyebrows or eyelashes. In some embodiments, an iTR factor is used to treat androgenic alopecia or "male pattern baldness" (which can affect males and females). In some embodiments, an iTR factor is used to treat alopecia areata, which involves patchy hair loss on the scalp, alopecia totalis, which involves the loss of all head hair, or alopecia universalis, which involves the loss of all hair from the head and the body. In some embodiments, an iTR factor is applied to a site where hair growth is desired, e.g., the scalp or eyebrow region. In some embodiments, an iTR factor is applied to or near the edge of the eyelid, to promote eyelash growth. In some embodiments, an iTR factor is applied in a liquid formulation. In some embodiments an iTR factor is applied in a cream, ointment, paste, or gel. In some embodiments, an iTR factor is used to enhance hair growth after a burn, surgery, chemotherapy, or other event causing loss of hair or hear-bearing skin.

In some embodiments, an iTR factor or factors are administered to tissues afflicted with age-related degenerative changes to regenerate youthful function. Said age-related degenerative changes includes by way of nonlimiting example, age-related macular degeneration, coronary disease, osteoporosis, osteonecrosis, heart failure, emphysema, peripheral artery disease, vocal cord atrophy, hearing loss, Alzheimer's disease, Parkinson's disease, skin ulcers, and other age-related degenerative diseases. In some embodiments, said iTR factors are co-administered with a vector expressing the catalytic component of telomerase to extend cell lifespan.

In some embodiments, an iTR factor or factors are administered to enhance replacement of cells that have been lost or damaged due to insults such as chemotherapy, radiation, or toxins. In some embodiments such cells are stromal cells of solid organs and tissues.

Inventive methods of treatment can include a step of identifying or providing a subject suffering from or at risk of a disease or condition in which in which enhancing regeneration would be of benefit to the subject. In some embodiments, the subject has experienced injury (e.g., physical trauma) or damage to a tissue or organ. In some embodiments the damage is to a limb or digit. In some embodiments, a subject suffers from a disease affecting the cardiovascular, digestive, endocrine, musculoskeletal, gastrointestinal, hepatic, integumentary, nervous, respiratory, or urinary system. In some embodiments, tissue damage is to a tissue, organ, or structure such as cartilage, bone, heart, blood vessel, esophagus, stomach, liver, gallbladder, pancreas, intestines, rectum, anus, endocrine gland, skin, hair follicle, tooth, gum, lip, nose, mouth, thymus, spleen, skeletal muscle, smooth muscle, joint, brain, spinal cord, peripheral nerve, ovary, fallopian tube, uterus, vagina, mammary gland, testes, vas deferens, seminal vesicle, prostate, penis, pharynx, larynx, trachea, bronchi, lungs, kidney, ureter, bladder, urethra, eye (e.g., retina, cornea), or ear (e.g., organ of *Corti*).

In some embodiments a compound or composition is administered to a subject at least once within approximately 2, 4, 8, 12, 24, 48, 72, or 96 hours after a subject has suffered tissue damage (e.g., an injury or an acute disease-related event such as a myocardial infarction or stroke) and, optionally, at least once thereafter. In some embodiments a compound or composition is administered to a subject at least once within approximately 1-2 weeks, 2-6 weeks, or 6-12 weeks, after a subject has suffered tissue damage and, optionally, at least once thereafter.

In some embodiments of the invention, it may useful to stimulate or facilitate regeneration or de novo development of a missing or hypoplastic tissue, organ, or structure by, for example, removing the skin, removing at least some tissue at a site where regeneration or de novo development is desired, abrading a joint or bone surface where regeneration or de novo development is desired, and/or inflicting another type of wound on a subject. In the case of regeneration after tissue damage, it may be desirable to remove (e.g., by surgical excision or debridement) at least some of the damaged tissue. In some embodiments, an iTR factor is administered at or near the site of such removal or abrasion.

In some embodiments, an iTR factor is used to enhance generation of a tissue or organ in a subject in whom such tissue or organ is at least partially absent as a result of a congenital disorder, e.g., a genetic disease. Many congenital malformations result in hypoplasia or absence of a variety of tissues, organs, or body structures such as limbs or digits. In other instances a developmental disorder resulting in hypoplasia of a tissue, organ, or other body structure becomes evident after birth. In some embodiments, an iTR factor is administered to a subject suffering from hypoplasia or absence of a tissue, organ, or other body structure, in order to stimulate growth or development of such tissue, organ, or other body structure. In some aspects, the invention provides a method of enhancing generation of a tissue, organ, or other body structure in a subject suffering from hypoplasia or congenital absence of such tissue, organ, or other body structure, the method comprising administering an iTR factor to the subject. In some embodiments, an iTR factor is administered to the subject prior to birth, i.e., in utero. The various aspects and embodiments of the invention described herein with respect to regeneration are applicable to such de novo generation of a tissue, organ, or other body structure and are encompassed within the invention.

In some aspects, an iTR factor is used to enhance generation of tissue in any of a variety of situations in which new tissue growth is useful at locations where such tissue did not previously exist. For example, generating bone tissue between joints is frequently useful in the context of fusion of spinal or other joints. iTR factors may be tested in a variety of animal models of regeneration. In one aspect, a modulator of iTR is tested in murine species. For example, mice can be wounded (e.g., by incision, amputation, transection, or removal of a tissue fragment). An ITR factor is applied to the site of the wound and/or to a removed tissue fragment and its effect on regeneration is assessed. The effect of a modulator of vertebrate TR can be tested in a variety of vertebrate models for tissue or organ regeneration. For example, fin regeneration can be assessed in zebra fish, e.g., as described in (Mathew L K, Unraveling tissue regeneration pathways using chemical genetics. *J Biol Chem.* 282(48):35202-10 (2007)), and can serve as a model for limb regeneration. Rodent, canine, equine, caprine, fish, amphibian, and other animal models useful for testing the effects of treatment on regeneration of tissues and organs such as heart, lung, limbs, skeletal muscle, bone, etc., are widely available. For example, various animal models for musculoskeletal regeneration are discussed in *Tissue Eng Part B Rev.* 16(1) (2010). A commonly used animal model for the study of liver regeneration involves surgical removal of a larger portion of the rodent liver. Other models for liver regeneration include acute or chronic liver injurer or liver failure caused by toxins such as carbon tetrachloride. In some embodiments, a model for hair regeneration or healing of skin wounds involves excising a patch of skin, e.g., from a mouse. Regeneration of hair follicles, hair growth, re-epithelialization, gland formation, etc., can be assessed.

The compounds and compositions disclosed herein and/or identified using a method and/or assay system described herein may be administered by any suitable means such as orally, intranasally, subcutaneously, intramuscularly, intravenously, intra-arterially, parenterally, intraperitoneally, intrathecally, intratracheally, ocularly, sublingually, vaginally, rectally, dermally, or by inhalation, e.g., as an aerosol. The particular mode selected will depend, of course, upon the particular compound selected, the particular condition being treated and the dosage required for therapeutic efficacy. The methods of this invention, generally speaking, may be practiced using any mode of administration that is medically or veterinarily acceptable, meaning any mode that produces acceptable levels of efficacy without causing clinically unacceptable (e.g., medically or veterinarily unacceptable) adverse effects. Suitable preparations, e.g., substantially pure preparations, of one or more compound(s) may be combined with one or more pharmaceutically acceptable carriers or excipients, etc., to produce an appropriate pharmaceutical composition suitable for administration to a subject. Such pharmaceutically acceptable compositions are an aspect of the invention. The term "pharmaceutically acceptable carrier or excipient" refers to a carrier (which term encompasses carriers, media, diluents, solvents, vehicles, etc.) or excipient which does not significantly interfere with the biological activity or effectiveness of the active ingredient(s) of a composition and which is not excessively toxic to the host at the concentrations at which it is used or administered. Other pharmaceutically acceptable ingredients can be present in the composition as well. Suitable substances and their use for the formulation of pharmaceutically active compounds are well-known in the art (see, for example, "Remington's Pharmaceutical Sciences", E. W. Martin, 19th Ed., 1995, Mack Publishing Co.: Easton, Pa., and more recent editions or versions thereof, such as Remington: The Science and Practice of Pharmacy. 21st Edition. Philadelphia, Pa. Lippincott Williams & Wilkins, 2005, for additional discussion of pharmaceutically acceptable substances and methods of preparing pharmaceutical compositions of various types). Furthermore, compounds and compositions of the invention may be used in combination with any compound or composition used in the art for treatment of a particular disease or condition of interest.

A pharmaceutical composition is typically formulated to be compatible with its intended route of administration. For example, preparations for parenteral administration include sterile aqueous or non-aqueous solutions, suspensions, and emulsions. Aqueous carriers include water, alcoholic/aqueous solutions, emulsions or suspensions, including saline and buffered media, e.g., sodium chloride solution, Ringer's dextrose, dextrose and sodium chloride, lactated Ringer's. Examples of non-aqueous solvents are propylene glycol, polyethylene glycol, vegetable oils such as olive oil, and injectable organic esters such as ethyl oleate, fixed oils, polyethylene glycols, glycerine, propylene glycol or other synthetic solvents; preservatives, e.g., antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. pH can be adjusted with acids or bases, such as hydrochloric acid or sodium hydroxide. Such parenteral preparations can be enclosed in ampoules, disposable syringes or multiple dose vials made of glass or plastic.

For oral administration, compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like. Suitable excipients for oral dosage forms are, e.g., fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP).

For administration by inhalation, inventive compositions may be delivered in the form of an aerosol spray from a pressured container or dispenser which contains a suitable propellant, e.g., a gas such as carbon dioxide, a fluorocarbon, or a nebulizer. Liquid or dry aerosol (e.g., dry powders, large porous particles, etc.) can be used. The present invention also contemplates delivery of compositions using a nasal spray or other forms of nasal administration.

For topical applications, pharmaceutical compositions may be formulated in a suitable ointment, lotion, gel, or cream containing the active components suspended or dissolved in one or more pharmaceutically acceptable carriers suitable for use in such composition.

For local delivery to the eye, the pharmaceutically acceptable compositions may be formulated as solutions or micronized suspensions in isotonic, pH adjusted sterile saline, e.g., for use in eye drops, or in an ointment, or for intra-ocularly administration, e.g., by injection.

Pharmaceutical compositions may be formulated for transmucosal or transdermal delivery. For transmucosal or transdermal administration, penetrants appropriate to the barrier to be permeated may be used in the formulation. Such penetrants are generally known in the art. Inventive pharmaceutical compositions may be formulated as suppositories (e.g., with conventional suppository bases such as cocoa butter and other glycerides) or as retention enemas for rectal delivery.

In some embodiments, a composition includes one or more agents intended to protect the active agent(s) against rapid elimination from the body, such as a controlled release formulation, implants, microencapsulated delivery system, etc. Compositions may incorporate agents to improve stability (e.g., in the gastrointestinal tract or bloodstream) and/or to enhance absorption. Compounds may be encapsulated or incorporated into particles, e.g., microparticles or nanoparticles. Biodegradable, biocompatible polymers can be used, such as ethylene vinyl acetate, polyanhydrides, polyglycolic acid, PLGA, collagen, polyorthoesters, polyethers, and polylactic acid. Methods for preparation of such formulations will be apparent to those skilled in the art. For example, and without limitation, a number of particle, lipid, and/or polymer-based delivery systems are known in the art for delivery of siRNA. The invention contemplates use of such compositions. Liposomes or other lipid-based particles can also be used as pharmaceutically acceptable carriers.

Pharmaceutical compositions and compounds for use in such compositions may be manufactured under conditions that meet standards, criteria, or guidelines prescribed by a regulatory agency. For example, such compositions and compounds may be manufactured according to Good Manufacturing Practices (GMP) and/or subjected to quality control procedures appropriate for pharmaceutical agents to be administered to humans and can be provided with a label approved by a government regulatory agency responsible for regulating pharmaceutical, surgical, or other therapeutically useful products.

Pharmaceutical compositions of the invention, when administered to a subject for treatment purposes, are preferably administered for a time and in an amount sufficient to treat the disease or condition for which they are administered. Therapeutic efficacy and toxicity of active agents can be assessed by standard pharmaceutical procedures in cell cultures or experimental animals. The data obtained from cell culture assays and animal studies can be used in formulating a range of dosages suitable for use in humans or other subjects. Different doses for human administration can be further tested in clinical trials in humans as known in the art. The dose used may be the maximum tolerated dose or a lower dose. A therapeutically effective dose of an active agent in a pharmaceutical composition may be within a range of about 0.001 mg/kg to about 100 mg/kg body weight, about 0.01 to about 25 mg/kg body weight, about 0.1 to about 20 mg/kg body weight, about 1 to about 10 mg/kg. Other exemplary doses include, for example, about 1 µg/kg to about 500 mg/kg, about 100 µg/kg to about 5 mg/kg. In some embodiments a single dose is administered while in other embodiments multiple doses are administered. Those of ordinary skill in the art will appreciate that appropriate doses in any particular circumstance depend upon the potency of the agent(s) utilized, and may optionally be tailored to the particular recipient. The specific dose level for a subject may depend upon a variety of factors including the activity of the specific agent(s) employed, the particular disease or condition and its severity, the age, body weight, general health of the subject, etc. It may be desirable to formulate pharmaceutical compositions, particularly those for oral or parenteral compositions, in unit dosage form for ease of administration and uniformity of dosage. Unit dosage form, as that term is used herein, refers to physically discrete units suited as unitary dosages for the subject to be treated; each unit containing a predetermined quantity of active agent(s) calculated to produce the desired therapeutic effect in association with an appropriate pharmaceutically acceptable carrier. It will be understood that a therapeutic regimen may include administration of multiple doses, unit dosage forms, over a period of time, which can extend over days, weeks, months, or years. A subject may receive one or more doses a day, or may receive doses every other day or less frequently, within a treatment period. For example, administration may be biweekly, weekly, etc. Administration may continue, for example, until appropriate structure and/or function of a tissue or organ has been at least partially restored and/or until continued administration of the compound does not appear to promote further regeneration or improvement. In some embodiments, a subject administers one or more doses of a composition of the invention to him or herself.

In some embodiments, two or more compounds or compositions are administered in combination, e.g., for purposes of enhancing regeneration. Compounds or compositions administered in combination may be administered together in the same composition, or separately. In some embodiments, administration "in combination" means, with respect to administration of first and second compounds or compositions, administration performed such that (i) a dose of the second compound is administered before more than 90% of the most recently administered dose of the first agent has been metabolized to an inactive form or excreted from the body; or (ii) doses of the first and second compound are administered within 48, 72, 96, 120, or 168 hours of each other, or (iii) the agents are administered during overlapping time periods (e.g., by continuous or intermittent infusion); or (iv) any combination of the foregoing. In some embodiments, two or more iTR factors, or vectors expressing the catalytic component of telomerase and an iTR factor, are administered. In some embodiments an iTR factor is administered in combination with a combination with one or more growth factors, growth factor receptor ligands (e.g., agonists), hormones (e.g., steroid or peptide hormones), or signaling molecules, useful to promote regeneration and polarity. Of particular utility are organizing center molecules useful in organizing regeneration competent cells such as those produced using the methods of the present invention. In some embodiments, a growth factor is an epidermal growth factor family member (e.g., EGF, a neuregulin), a fibroblast growth factor (e.g., any of FGF1-FGF23), a hepatocyte growth factor (HGF), a nerve growth factor, a bone morphogenetic protein (e.g., any of BMP1-BMP7), a vascular endothelial growth factor (VEGF), a wnt ligand, a wnt antagonist, retinoic acid, NOTUM, follistatin, sonic hedgehog, or other organizing center factors.

Those skilled in the art will recognize, or be able to ascertain using no more than routine experimentation, many equivalents to the specific embodiments of the invention described herein. The scope of the present invention is not intended to be limited to the Description or the details set forth therein. Articles such as "a", "an" and "the" may mean one or more than one unless indicated to the contrary or otherwise evident from the context. Certain of the inventive methods are often practiced using populations of cells, e.g., in vitro or in vivo. Thus references to "a cell" should be understood as including embodiments in which the cell is a member of a population of cells, e.g., a population comprising or consisting of cells that are substantially genetically identical. However, the invention encompasses embodiments in which inventive methods is/are applied to an individual cell. Thus, references to "cells" should be understood as including embodiments applicable to individual cells within a population of cells and embodiments applicable to individual isolated cells.

Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. It is contemplated that all embodiments described herein are applicable to all different aspects of the invention. It is also contemplated that any of the embodiments can be freely combined with one or more other such embodiments whenever appropriate. Furthermore, it is to be understood that the invention encompasses all variations, combinations, and permutations in which one or more limitations, elements, clauses, descriptive terms, etc., from one or more of the claims (whether original or subsequently added claims) is introduced into another claim (whether original or subsequently added). For example, any claim that is dependent on another claim can be modified to include one or more elements or limitations found in any other claim that is dependent on the same base claim, and any claim that refers to an element present in a different claim can be modified to include one or more elements or limitations found in any other claim that is dependent on the same base claim as such claim. Furthermore, where the claims recite a composition, the invention provides methods of making the composition, e.g., according to methods disclosed herein, and methods of using the composition, e.g., for purposes disclosed herein. Where the claims recite a method, the invention provides compositions suitable for performing the method, and methods of making the composition. Also, where the claims recite a method of making a composition, the invention provides compositions made according to the inventive methods and methods of using the composition, unless otherwise indicated or unless one of ordinary skill in the art would recognize that a contradiction or inconsistency would arise. Where elements are presented as lists, e.g., in Markush group format, each subgroup of the elements is also disclosed, and any element(s) can be removed from the group. For purposes of conciseness only some of these embodiments have been specifically recited herein, but the invention includes all such embodiments. It should also be understood that, in general, where the invention, or aspects of the invention, is/are referred to as comprising particular elements, features, etc., certain embodiments of the invention or aspects of the invention consist, or consist essentially of, such elements, features, etc.

Where numerical ranges are mentioned herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. Where phrases such as "less than X", "greater than X", or "at least X" is used (where X is a number or percentage), it should be understood that any reasonable value can be selected as the lower or upper limit of the range. It is also understood that where a list of numerical values is stated herein (whether or not prefaced by "at least"), the invention includes embodiments that relate to any intervening value or range defined by any two values in the list, and that the lowest value may be taken as a minimum and the greatest value may be taken as a maximum. Furthermore, where a list of numbers, e.g., percentages, is prefaced by "at least", the term applies to each number in the list. For any embodiment of the invention in which a numerical value is prefaced by "about" or "approximately", the invention includes an embodiment in which the exact value is recited. For any embodiment of the invention in which a numerical value is not prefaced by "about" or "approximately", the invention includes an embodiment in which the value is prefaced by "about" or "approximately". "Approximately" or "about" generally includes numbers that fall within a range of 1% or in some embodiments 5% or in some embodiments 10% of a number in either direction (greater than or less than the number) unless otherwise stated or otherwise evident from the context (e.g., where such number would impermissibly exceed 100% of a possible value). A "composition" as used herein, can include one or more than one component unless otherwise indicated. For example, a "composition comprising an activator or a TR activator" can consist or consist essentially of an activator of a TR activator or can contain one or more additional components. It should be understood that, unless otherwise indicated, an inhibitor or a TR inhibitor (or other compound referred to herein) in any embodiment of the invention may be used or administered in a composition that comprises one or more additional components including the presence of an activator of a TR activator.

Kits

Certain embodiments of the invention provide a kit comprising one or more genes in FIG. 1 or one or more gene products encoded by genes in FIG. 1. In one embodiment the kit comprises a gene or gene product encoded by one or more genes chosen from PCDHB2, PCDHB17, Nbla10527, RAB3IP, DLX1, DRD11P, FOXD1, AFF3, F2RL2, MN1, CBCAQH03 5, LOC791120, SIX1, OXTR, and WSB1. In other embodiments the kit comprises a gene or gene product encoded by one or more genes chosen from COMT, TRIM4, CAT, PSMD, SHMT, LOC205251, ZNF280D, S100A6, MGMT, ZNF280D, DYNLT3, NAALADL1, COX7A1, TSPYL5, IAH1, C18orf56, RPS7, FDPS, ELOVL6, ACAT2, and MAOA. In still other embodiments the kit comprises a gene or gene product encoded by a plurality of genes chosen from PCDHB2, PCDHB17, Nbla10527, RAB3IP, DLX1, DRD11P, FOXD1, LOC728755, AFF3, F2RL2, MN1, CBCAQH03 5, LOC791120, SIX1, OXTR, and WSB1. In yet further embodiments the kit comprises a gene or gene product encoded by a plurality of genes chosen from COMT, TRIM4, CAT, PSMD, SHMT, LOC205251, ZNF280D, S100A6, MGMT, ZNF280D, DYNLT3, NAALADL1, COX7A1, TSPYL5, IAH1, C18orf56, RPS7, FDPS, ELOVL6, INSIG1, ACAT2, and MAOA.

In some embodiments the kit may comprise one or more agents that inhibits expression of one or more genes chosen from PCDHB2, PCDHB17, Nbla10527, RAB3IP, DLX1, DRD11P, FOXD1, LOC728755, AFF3, F2RL2, MN1, CBCAQH03 5, LOC791120, SIX1, OXTR, and WSB1. In other embodiments the kit may comprise one or more agents that inhibits expression of one or more genes chosen from COMT, TRIM4, CAT, PSMD, SHMT, LOC205251, ZNF280D, S100A6, MGMT, ZNF280D, DYNLT3, NAALADL1, COX7A1, TSPYL5, IAH1, C18orf56, RPS7, FDPS, ELOVL6, INSIG1, ACAT2, and MAOA. In still other embodiments the kit may comprise a plurality of agents that inhibits expression of a plurality of genes chosen from PCDHB2, PCDHB17, Nbla10527, RAB3IP, DLX1, DRD11P, FOXD1, LOC728755, AFF3, F2RL2, MN1, CBCAQH03 5, LOC791120, SIX1, OXTR, and WSB1. In other embodiments the kit may comprise a plurality of agents that inhibits expression of a plurality of genes chosen from COMT, TRIM4, CAT, PSMD, SHMT, LOC20525L ZNF280D, S100A6, ZNF280D, DYNLT3, NAALADL1, COX7A1, TSPYL5, IAH1, C18orf56, RPS7, FDPS, ELOVL6, INSIG1, ACAT2, and MAOA.

In some embodiments the kit provides an agent that binds to one or more genes or gene products encoded for by one or more genes chosen from PCDHB2, PCDHB17, Nbla10527, RAB3IP, DLX1, DRD11P, FOXD1, LOC728755, AFF3, F2RL2, MN1, CBCAQH03 5, LOC791120, SIX1, OXTR, and WSB1. In other embodiments the kit provides an agent that binds to one or more genes or gene products encoded for by one or more genes chosen from COMT, TRIM4, CAT, PSMD, SHMT, LOC205251, ZNF280D, S100A6, MGMT, ZNF280D, DYNLT3, NAALADL1, COX7A1, TSPYL5, IAH1, C18orf56, RPS7, FDPS, ELOVL6, INSIG1, ACAT2, and MAOA. The agent that binds to one or more genes may inhibit expression of the gene or a gene product encoded by the gene. The agent may be a protein, e.g. antibody. The agent may be a nucleic acid such as a DNA molecule, an RNA molecule such as an mRNA molecule, a siRNA molecule, a dsRNA molecule.

The contents of the kit may be provided in one or more containers. The contents of the kit may be provided in solution, e.g. in a suitable buffer such as PBS or deionized water. Alternatively the contents of the kit may be provided in dry form, e.g. lyophilized.

Methods

In addition to the methods described below, methods that find use in the production and use of cells with an embryonic pattern of gene expression corresponding with scarless regenerative potential can be found in the following: PCT application Ser. No. PCT/US2006/013519 filed on Apr. 11, 2006 and titled "Novel Uses of Cells With Prenatal Patterns of Gene Expression"; U.S. patent application Ser. No. 11/604,047 filed on Nov. 21, 2006 and titled "Methods to Accelerate the Isolation of Novel Cell Strains from Pluripotent Stein Cells and Cells Obtained Thereby"; and U.S. patent application Ser. No. 12/504,630 filed on Jul. 16, 2009 and titled "Methods to Accelerate the isolation of Novel Cell Strains from Pluripotent Stem Cells and Cells Obtained Thereby", each of which is incorporated by reference herein in its entirety.

Preparation of Hyaluronate and Collagen Hydrogel.

HyStem-C (BioTime, Alameda, CA, USA) is reconstituted following the manufacturer's instructions. Briefly, the HyStem component (thiol modified hyaluronan, 10 mg) is dissolved in 1.0 ml degassed deionized water for about 20 minutes to prepare a 1% w/v solution. The Gelin-S component (thiol modified gelatin, 10 mg) is dissolved in 1 ml degassed deionized water to prepare a 1% w/v solution, and PEGDA (PEG diacrylate, 10 mg) is dissolved in 0.5 ml degassed deionized water to prepare a 2% w/v solution. Then, HyStem (1 ml, 1% w/v) is mixed with Gelin-S (1 ml, 1% w/v) immediately before use. Pelleted cells are resuspended in recently prepared HyStem:Gelin-S (1:1 v/v) mix described above. Upon the addition of cross linker PEGDA, the cell suspension, at a final concentration of $2.0 \times 10^7$ cells/ml, the cell/matrix combination is injected into the target tissue. RNAi By way of nonlimiting example, dsRNA is prepared from in vitro transcription reactions (Promega) using PCR-generated templates with flanking T7 promoters, purified by phenol extraction and ethanol precipitation, and annealed after resuspension in water. Intact experimental animals are injected with 4.times.30 nL dsRNA on three consecutive days following induced tissue injury beginning with the first injection two hours after surgery.

EXAMPLES

Example 1

Identification of iTR Genes by Comparing Gene Expression in hES, iPS, and Clonal EP Cell Lines to Diverse Fetal and Adult-Derived Somatic Cell Types Illumina gene expression microarray analysis was performed in diverse adult and embryonic cell types including 14 diverse blood cell types, 115 diverse fetal and adult-derived somatic cell types from all three germ layers, 545 diverse clonal hES-derived and iPS-derived EP cell lines, 12 hES cell lines and 17 human iPS cell lines. The average RFU values for each probe in the fetal/adult-derived cells was compared to the corresponding average in the clonal EP cell lines and probes with relatively uniformly higher expression in one of the two sets were identified. As shown in FIG. 1, and FIGS. 2-15, these genes represent factors with known roles in oxidative phosphorylation (COX7A1), transcription factors with as SIX1 and DLX1, and other diverse activities within the cell. RFU values below a value of 100 are considered background signal (i.e. no expression detectable).

Example 2

Modification of iTR genes in transgenic mice and assays for iTR in adult animals. The embryonic patterns of expression of the genes: CAT, COMT, COX7A1, DLX1, DRD11P, LOC205251 NAALADL1, PCDHB2, PCDHB17, Primary neuroblastoma cDNA, clone:Nbla10527, RAB3IP, SIX1, TRIM4, and ZNF280D are induced individually or in combination to document their effects on increasing tissue regeneration in incised ear lobes and other somatic tissues.

Example 3

In vitro assay of human stromal tissue regeneration through modulation of iTR genes. The regenerative potential of up-regulating iTR inducing genes or down-regulating iTR inhibitory genes can be assayed using the in vitro wound repair assay described herein. In brief, a scratch test was utilized as described (*Nature Protocols* 2, 329-333 (2007) Liang C C et al "In vitro scratch assay: a convenient and inexpensive method for analysis of cell migration in vitro"). The assay utilized neonatal human foreskin fibroblasts (Xgene Corp, Sausalito CA) that expressed COX7A1 at levels comparable to other fetal and adult-derived stromal cells described herein. Fibroblasts were grown to confluence using DMEM medium supplemented with 10% FBS cultured in 6 well plates previously coated with 0.1% gelatin then cultured in a humidified incubator with 5% $O_2$ and 10% $CO_2$.

The reagents below were used on day 0 to alter the expression of the iTR inhibitory gene COX7A1:
SMARTpool: ON-TARGETplus COX7A1 siRNA, 5 nmole (Dharmacon, cat #L-013152-02-0005)
ON-TARGETplus Non-targeting Pool, 5 nmole (Dharmacon, cat #D-001810-10-05)
DharmaFECT 1 Transfection Reagent, 0.75 mL (Dharmacon, cat #T-2001-02)
Serum-free, antibiotic free, base medium
Antibiotic-free complete medium Stock solutions (100 uM) of both non-targeting pool siRNA and on-target (COX7A1) siRNA pool were prepared by the addition of 50 ul of sterile water to the 5 nmoles. Then, 5 uM solutions of non-targeting and on-target siRNA were prepared upon dilution using sterile water. 50 ul of each 50 µM siRNA solution was added to 2 respective labeled microfuge tubes containing 450 ul of serum free medium (DMEM medium+glutamax 2 mM) for a total of 500 ul each.

The Transfection reagent was prepared upon the addition of 11.0 ul in 2090 ul of serum-free medium (DMEM+glutamax 2 mM). After vortexing, spinning and letting sit 5 minutes, 500 ul of the transfection mix was added to 500 ul of (a) non-targeting siRNA mix (control) and (b) on-target siRNA mix. The reagents (1 ml each) were mixed by pipetting up and down.

Transfection was initiated when after the growth medium of cultured Xgene foreskin fibroblasts was removed by aspiration, washed with PBS, and then 1.6 ml of antibiotic free growth medium was fed to each well of a 6 well plate. Then 400 ul of the (a) transfection agent non-targeting siRNA control. (b) on-targeting transfection agent mix was added to yield 2 ml/treated well. Final concentration of siRNA was 50 nM. The plate was swirled to assure even distribution and placed in a humidified incubator at 5% $CO_2$ and 10% $CO_2$ for 6 hours.

After 6 hours the plate was removed from the incubator and a "scratch" was made using a 200 ul pipet tip in the center of each well. The plate was then washed twice with PBS, fed fresh growth medium (3 ml/well) and placed back into the incubator. Photographs were taken at 4× to observe cell mobility, proliferation, and morphology on DO (shortly after "scratch"), D1 and D2. RNA was extracted at days 2 and 4 for subsequent qPCR analysis.

As shown in FIG. 16, the down-regulation of the iTR inhibitory gene COX7A1 caused a markedly improved regeneration of three-dimensional tissue architecture in that the regeneration occurred at an accelerated rate compared to control somatic cells. RNA from the samples was extracted and assayed by PCR for relative levels of the transcripts for ACAT2 and COL1A1, genes implicated in the myofibroblastic contractile response of stromal cells in a scarring wound bed, and a fibrotic scarring response respectively. As shown in FIG. 17, neonatal foreskin fibroblasts responded to the down-regulation of the iTR inhibitory gene COX7A1 by decreasing the expression of ACAT2 and COL1A1 consistent with the downregulation of COX7A1 leading to increased regeneration of three dimensional human tissue and simultaneously leading to a regeneration with decreased scar-forming response.

In addition to COX7A1, other iTR modulators as described herein used singly or in combination are substituted for COX7A1 to assay in vitro for regeneration of three dimensional tissue structure and decreased fibrotic, scarring response to tissue damage.

What is claimed is:

1. A method of increasing regenerative potential of mammalian connective tissue comprising administering to the one or more cells of the connective tissue a composition comprising a de-differentiation gene of OXTR and one or more de-differentiation genes selected from the group consisting of PCDHB2, PCDHB17, Nbla10527, RAB3IP, DLX1, DRD11P, FOXD1, LOC728755, AFF3, F2RL2, MN1, CBCAQH03 5', LOC791120, SIX1, and WSB1,
wherein the administering the composition to the one or more cells of the connective tissue is ex vivo or in vitro, and
wherein one or more viral vectors comprise the OXTR gene and the one or more de-differentiation genes.

2. The method of claim 1, wherein the connective tissue is from human.

3. The method of claim 1, wherein the connective tissue is from an ear.

4. The method of claim 1, wherein the connective tissue is from an endocrine gland, wherein the endocrine gland is selected from the group consisting of thyroid, parathyroid, adrenal, and endocrine portion of pancreas.

5. The method of claim 1, wherein the connective tissue is from a bone, a skeletal muscle, a limb or a digit.

6. The method of claim 1, wherein the connective tissue involves a hair follicle or an epithelial cell.

7. The method of claim 1, wherein the one or more de-differentiation genes is SIX1.

8. The method of claim 1, wherein the one or more viral vectors are a retroviral vector, a lentiviral vector, or an adenoviral vector.

9. The method of claim 1, wherein the connective tissue is skin.

10. A kit for enhancing regenerative potential of mammalian connective tissue, wherein the kit comprises a composition comprising a de-differentiation gene of OXTR and one or more de-differentiation genes selected from the group consisting of PCDHB2, PCDHB17, Nbla10527, RAB3IP, DLX1, DRD11P, FOXD1, LOC728755, AFF3, F2RL2, MN1, CBCAQH03 5', LOC791120, SIX1, and WSB1, one or more viral vectors comprise the OXTR gene and the one or more de-differentiation genes.

11. The kit of claim 10, further comprising one or more compounds that form a hydrogel.

12. The kit of claim 11, wherein the one or more compounds that form the hydrogel comprises a monomer, polymer, initiating agent, cross-linking agent or any combination thereof.

* * * * *